United States Patent
Martin et al.

(10) Patent No.: US 9,254,371 B2
(45) Date of Patent: Feb. 9, 2016

(54) RETRIEVAL SYSTEMS AND METHODS FOR USE THEREOF

(75) Inventors: Brian B. Martin, Felton, CA (US); David I. Levy, San Diego, CA (US)

(73) Assignee: Lazarus Effect, Inc., Campbell, CA (US)

( * ) Notice: Subject to any disclaimer, the term of this patent is extended or adjusted under 35 U.S.C. 154(b) by 676 days.

(21) Appl. No.: 13/226,222

(22) Filed: Sep. 6, 2011

(65) Prior Publication Data

US 2012/0197285 A1 Aug. 2, 2012

Related U.S. Application Data

(63) Continuation of application No. PCT/US2010/026571, filed on Mar. 8, 2010.

(60) Provisional application No. 61/158,324, filed on Mar. 6, 2009, provisional application No. 61/171,419, filed on Apr. 21, 2009.

(51) Int. Cl.
| | |
|---|---|
| *A61B 17/221* | (2006.01) |
| *A61M 25/00* | (2006.01) |
| *A61F 2/01* | (2006.01) |
| *A61M 25/10* | (2013.01) |
| *A61B 17/22* | (2006.01) |
| *A61M 25/01* | (2006.01) |
| *A61M 25/06* | (2006.01) |

(52) U.S. Cl.
CPC .............. *A61M 25/00* (2013.01); *A61B 17/221* (2013.01); *A61F 2/013* (2013.01); *A61M 25/10* (2013.01); *A61B 2017/2217* (2013.01); *A61B 2017/22084* (2013.01); *A61B 2017/22094* (2013.01); *A61F 2002/011* (2013.01); *A61F 2002/016* (2013.01); *A61F 2002/018* (2013.01); *A61F 2230/0006* (2013.01); *A61F 2230/0067* (2013.01); *A61F 2230/0069* (2013.01); *A61F 2230/0093* (2013.01); *A61F 2230/0097* (2013.01); *A61M 25/01* (2013.01); *A61M 2025/0042* (2013.01); *A61M 2025/0063* (2013.01); *A61M 2025/0681* (2013.01)

(58) Field of Classification Search
CPC .............. A61B 17/22; A61B 17/22031; A61B 17/221; A61B 2017/22081; A61B 2017/22094; A61B 2017/2212; A61F 2/013; A61F 2/86; A61F 2/90; A61F 2002/016
USPC ......... 606/127, 128, 159, 191, 192, 194, 195, 606/198, 200
See application file for complete search history.

(56) References Cited

U.S. PATENT DOCUMENTS

| | | | |
|---|---|---|---|
| 2,918,919 | A | 12/1959 | Wallace |
| 2,943,626 | A | 7/1960 | Dormia |
| 3,996,938 | A | 12/1976 | Clark |

(Continued)

FOREIGN PATENT DOCUMENTS

| | | |
|---|---|---|
| CN | 1640505 A | 7/2005 |
| DE | 3501707 | 7/1986 |

(Continued)

*Primary Examiner* — Ryan Severson
(74) *Attorney, Agent, or Firm* — Mark J. Kertz, Esq.

(57) ABSTRACT

The devices and methods described herein relate to improved structures for removing obstructions from body lumens. Such devices have applicability in through-out the body, including clearing of blockages within the vasculature, by recanalizing or removing the obstruction within the body lumen.

18 Claims, 36 Drawing Sheets

(56) References Cited

U.S. PATENT DOCUMENTS

| | | |
|---|---|---|
| 4,347,846 A | 9/1982 | Dormia |
| 4,611,594 A | 9/1986 | Grayhack et al. |
| 4,699,147 A | 10/1987 | Chilson et al. |
| 4,790,812 A | 12/1988 | Hawkins, Jr. et al. |
| 4,807,626 A | 2/1989 | McGirr |
| 4,832,055 A | 5/1989 | Palestrant |
| 4,873,978 A | 10/1989 | Ginsburg |
| 4,969,891 A | 11/1990 | Gewertz |
| 5,057,114 A | 10/1991 | Wittich et al. |
| 5,059,178 A | 10/1991 | Ya |
| 5,102,415 A | 4/1992 | Guenther et al. |
| 5,147,400 A | 9/1992 | Kaplan et al. |
| 5,152,777 A | 10/1992 | Goldberg et al. |
| 5,192,286 A | 3/1993 | Phan et al. |
| 5,300,086 A | 4/1994 | Gory et al. |
| 5,443,478 A | 8/1995 | Purdy |
| 5,458,375 A | 10/1995 | Anspach et al. |
| 5,496,330 A | 3/1996 | Bates et al. |
| 5,509,900 A | 4/1996 | Kirkman |
| 5,653,684 A | 8/1997 | Laptewicz et al. |
| 5,658,296 A | 8/1997 | Bates et al. |
| 5,709,704 A | 1/1998 | Nott et al. |
| 5,733,302 A | 3/1998 | Myler et al. |
| 5,741,325 A | 4/1998 | Chaikof et al. |
| 5,792,156 A | 8/1998 | Perouse |
| 5,827,324 A | 10/1998 | Cassell et al. |
| 5,846,251 A | 12/1998 | Hart |
| 5,895,398 A | 4/1999 | Wensel et al. |
| 5,947,995 A | 9/1999 | Samuels |
| 5,968,090 A | 10/1999 | Ratcliff et al. |
| 5,971,938 A | 10/1999 | Hart et al. |
| 5,972,019 A | 10/1999 | Engelson et al. |
| 6,001,118 A | 12/1999 | Daniel et al. |
| 6,033,394 A | 3/2000 | Vidlund et al. |
| 6,053,932 A | 4/2000 | Daniel et al. |
| 6,066,149 A | 5/2000 | Samson et al. |
| 6,066,158 A | 5/2000 | Engelson et al. |
| 6,096,053 A | 8/2000 | Bates |
| 6,099,534 A | 8/2000 | Bates et al. |
| 6,159,220 A | 12/2000 | Gobron et al. |
| 6,165,200 A | 12/2000 | Tsugita et al. |
| 6,168,603 B1 | 1/2001 | Leslie et al. |
| 6,174,318 B1 | 1/2001 | Bates et al. |
| 6,190,394 B1 | 2/2001 | Lind et al. |
| 6,217,609 B1 | 4/2001 | Haverkost |
| 6,221,006 B1 | 4/2001 | Dubrul et al. |
| 6,245,089 B1 | 6/2001 | Daniel et al. |
| 6,248,113 B1 | 6/2001 | Fina |
| 6,264,664 B1 | 7/2001 | Avellanet |
| 6,302,895 B1 | 10/2001 | Gobron et al. |
| 6,309,399 B1 | 10/2001 | Barbut et al. |
| 6,348,056 B1 | 2/2002 | Bates et al. |
| 6,350,266 B1 | 2/2002 | White et al. |
| 6,364,895 B1 | 4/2002 | Greenhalgh |
| 6,371,971 B1 | 4/2002 | Tsugita et al. |
| 6,383,195 B1 | 5/2002 | Richard |
| 6,383,196 B1 | 5/2002 | Leslie et al. |
| 6,402,771 B1 | 6/2002 | Palmer et al. |
| 6,409,750 B1 | 6/2002 | Hyodoh et al. |
| 6,416,505 B1 | 7/2002 | Fleischman et al. |
| 6,425,909 B1 | 7/2002 | Dieck et al. |
| 6,436,112 B2 | 8/2002 | Wensel et al. |
| 6,443,972 B1 | 9/2002 | Bosma et al. |
| 6,458,139 B1 | 10/2002 | Palmer et al. |
| 6,485,497 B2 | 11/2002 | Wensel et al. |
| 6,494,884 B2 | 12/2002 | Gifford, III et al. |
| 6,506,204 B2 | 1/2003 | Mazzocchi |
| 6,514,273 B1 | 2/2003 | Voss et al. |
| 6,530,935 B2 | 3/2003 | Wensel et al. |
| 6,540,657 B2 | 4/2003 | Cross, III et al. |
| 6,551,342 B1 | 4/2003 | Shen et al. |
| 6,575,997 B1 | 6/2003 | Palmer et al. |
| 6,585,753 B2 | 7/2003 | Eder et al. |
| 6,592,605 B2 | 7/2003 | Lenker et al. |
| 6,592,607 B1 | 7/2003 | Palmer et al. |
| 6,602,271 B2 | 8/2003 | Adams et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,620,148 B1 | 9/2003 | Tsugita |
| 6,635,068 B1 | 10/2003 | Dubrul et al. |
| 6,636,758 B2 | 10/2003 | Sanchez et al. |
| 6,638,245 B2 | 10/2003 | Miller et al. |
| 6,641,590 B1 | 11/2003 | Palmer et al. |
| 6,645,199 B1 | 11/2003 | Jenkins et al. |
| 6,652,505 B1 | 11/2003 | Tsugita |
| 6,652,548 B2 | 11/2003 | Evans et al. |
| 6,660,021 B1 | 12/2003 | Palmer et al. |
| 6,663,650 B2 | 12/2003 | Sepetka et al. |
| 6,673,042 B1 | 1/2004 | Samson et al. |
| 6,679,893 B1 | 1/2004 | Tran |
| 6,685,738 B2 | 2/2004 | Chouinard et al. |
| 6,692,508 B2 | 2/2004 | Wensel et al. |
| 6,692,509 B2 | 2/2004 | Wensel et al. |
| 6,695,858 B1 | 2/2004 | Dubrul et al. |
| 6,702,782 B2 | 3/2004 | Miller et al. |
| 6,730,104 B1 | 5/2004 | Sepetka et al. |
| 6,745,080 B2 | 6/2004 | Koblish |
| 6,746,468 B1 | 6/2004 | Sepetka et al. |
| 6,749,619 B2 | 6/2004 | Ouriel et al. |
| 6,755,813 B2 | 6/2004 | Ouriel et al. |
| 6,800,080 B1 | 10/2004 | Bates |
| 6,824,545 B2 | 11/2004 | Sepetka et al. |
| 6,872,211 B2 | 3/2005 | White et al. |
| 6,872,216 B2 | 3/2005 | Daniel et al. |
| 6,890,341 B2 | 5/2005 | Dieck et al. |
| 6,893,431 B2 | 5/2005 | Naimark et al. |
| 6,905,503 B2 | 6/2005 | Gifford, III et al. |
| 6,913,612 B2 | 7/2005 | Palmer et al. |
| 6,936,059 B2 | 8/2005 | Belef |
| 6,939,362 B2 | 9/2005 | Boyle et al. |
| 6,945,977 B2 | 9/2005 | Demarais et al. |
| 6,953,465 B2 | 10/2005 | Dieck et al. |
| 6,964,672 B2 | 11/2005 | Brady et al. |
| 7,004,955 B2 | 2/2006 | Shen et al. |
| 7,004,956 B2 | 2/2006 | Palmer et al. |
| 7,037,320 B2 | 5/2006 | Brady et al. |
| 7,058,456 B2 | 6/2006 | Pierce |
| 7,097,653 B2 | 8/2006 | Freudenthal et al. |
| 7,101,380 B2 | 9/2006 | Khachin et al. |
| 7,169,165 B2 | 1/2007 | Belef et al. |
| 7,179,273 B1 | 2/2007 | Palmer et al. |
| 7,182,771 B1 | 2/2007 | Houser et al. |
| 7,235,061 B2 | 6/2007 | Tsugita |
| 7,534,252 B2 | 5/2009 | Sepetka et al. |
| 8,105,333 B2 | 1/2012 | Sepetka et al. |
| 2001/0041909 A1 | 11/2001 | Tsugita et al. |
| 2001/0044634 A1 | 11/2001 | Don et al. |
| 2001/0051810 A1 | 12/2001 | Dubrul et al. |
| 2002/0002396 A1 | 1/2002 | Fulkerson |
| 2002/0004667 A1 | 1/2002 | Adams et al. |
| 2002/0026211 A1 | 2/2002 | Khosravi et al. |
| 2002/0058904 A1 | 5/2002 | Boock et al. |
| 2002/0062135 A1 | 5/2002 | Mazzocchi et al. |
| 2002/0072764 A1 | 6/2002 | Sepetka et al. |
| 2002/0082558 A1 | 6/2002 | Samson et al. |
| 2002/0123765 A1 | 9/2002 | Sepetka et al. |
| 2002/0151928 A1 | 10/2002 | Leslie et al. |
| 2002/0188314 A1 | 12/2002 | Anderson et al. |
| 2002/0193825 A1 | 12/2002 | McGuckin et al. |
| 2003/0004542 A1 | 1/2003 | Wensel et al. |
| 2003/0023265 A1 | 1/2003 | Forber |
| 2003/0040771 A1 | 2/2003 | Hyodoh et al. |
| 2003/0050663 A1 | 3/2003 | Khachin et al. |
| 2003/0060782 A1 | 3/2003 | Bose et al. |
| 2003/0093087 A1 | 5/2003 | Jones et al. |
| 2003/0144687 A1 | 7/2003 | Brady et al. |
| 2003/0153935 A1 | 8/2003 | Mialhe |
| 2003/0195556 A1 | 10/2003 | Stack et al. |
| 2004/0068288 A1 | 4/2004 | Palmer et al. |
| 2004/0073243 A1 | 4/2004 | Sepetka et al. |
| 2004/0079429 A1 | 4/2004 | Miller et al. |
| 2004/0133232 A1 | 7/2004 | Rosenbluth et al. |
| 2004/0138692 A1 | 7/2004 | Phung et al. |

(56) References Cited

U.S. PATENT DOCUMENTS

| | | |
|---|---|---|
| 2004/0153025 A1 | 8/2004 | Seifert et al. |
| 2004/0153118 A1 | 8/2004 | Clubb et al. |
| 2004/0172056 A1 | 9/2004 | Guterman et al. |
| 2004/0199201 A1 | 10/2004 | Kellett et al. |
| 2004/0199243 A1 | 10/2004 | Yodfat |
| 2004/0210116 A1 | 10/2004 | Nakao |
| 2004/0267301 A1 | 12/2004 | Boylan et al. |
| 2005/0004594 A1 | 1/2005 | Nool et al. |
| 2005/0033348 A1 | 2/2005 | Sepetka et al. |
| 2005/0038447 A1 | 2/2005 | Huffmaster |
| 2005/0043680 A1 | 2/2005 | Segal et al. |
| 2005/0043756 A1 | 2/2005 | Lavelle et al. |
| 2005/0049619 A1 | 3/2005 | Sepetka et al. |
| 2005/0055033 A1 | 3/2005 | Leslie et al. |
| 2005/0055047 A1 | 3/2005 | Greenhalgh |
| 2005/0059995 A1 | 3/2005 | Sepetka et al. |
| 2005/0080356 A1 | 4/2005 | Dapolito et al. |
| 2005/0085826 A1 | 4/2005 | Nair et al. |
| 2005/0085847 A1 | 4/2005 | Galdonik et al. |
| 2005/0085849 A1 | 4/2005 | Sepetka et al. |
| 2005/0090857 A1 | 4/2005 | Kusleika et al. |
| 2005/0090858 A1 | 4/2005 | Pavlovic |
| 2005/0125024 A1 | 6/2005 | Sepetka et al. |
| 2005/0131450 A1 | 6/2005 | Nicholson et al. |
| 2005/0137680 A1* | 6/2005 | Ortiz et al. .................. 623/1.16 |
| 2005/0171566 A1 | 8/2005 | Kanamaru |
| 2005/0203571 A1 | 9/2005 | Mazzocchi et al. |
| 2005/0209609 A1 | 9/2005 | Wallace |
| 2005/0216030 A1 | 9/2005 | Sepetka et al. |
| 2005/0216050 A1 | 9/2005 | Sepetka et al. |
| 2005/0234501 A1 | 10/2005 | Barone |
| 2005/0234505 A1 | 10/2005 | Diaz et al. |
| 2005/0277978 A1 | 12/2005 | Greenhalgh |
| 2005/0283166 A1 | 12/2005 | Greenhalgh |
| 2005/0283186 A1 | 12/2005 | Berrada et al. |
| 2006/0004404 A1 | 1/2006 | Khachin et al. |
| 2006/0009784 A1 | 1/2006 | Behl et al. |
| 2006/0047286 A1 | 3/2006 | West |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0095070 A1 | 5/2006 | Gilson et al. |
| 2006/0129166 A1 | 6/2006 | Lavelle |
| 2006/0129180 A1 | 6/2006 | Tsugita et al. |
| 2006/0155305 A1 | 7/2006 | Freudenthal et al. |
| 2006/0190070 A1 | 8/2006 | Dieck et al. |
| 2006/0195137 A1 | 8/2006 | Sepetka et al. |
| 2006/0229638 A1 | 10/2006 | Abrams et al. |
| 2006/0253145 A1 | 11/2006 | Lucas |
| 2006/0276805 A1 | 12/2006 | Yu |
| 2006/0282111 A1 | 12/2006 | Morsi |
| 2007/0112374 A1 | 5/2007 | Paul et al. |
| 2007/0118165 A1 | 5/2007 | DeMello et al. |
| 2007/0185500 A1 | 8/2007 | Martin et al. |
| 2007/0185501 A1 | 8/2007 | Martin et al. |
| 2007/0197103 A1 | 8/2007 | Martin et al. |
| 2007/0198029 A1 | 8/2007 | Martin et al. |
| 2007/0198030 A1 | 8/2007 | Martin et al. |
| 2007/0225749 A1 | 9/2007 | Martin et al. |
| 2007/0265656 A1 | 11/2007 | Amplatz et al. |
| 2008/0109031 A1 | 5/2008 | Sepetka et al. |
| 2008/0183198 A1 | 7/2008 | Sepetka et al. |
| 2008/0188885 A1 | 8/2008 | Sepetka et al. |
| 2008/0262528 A1 | 10/2008 | Martin |
| 2008/0262532 A1 | 10/2008 | Martin |
| 2009/0069828 A1 | 3/2009 | Martin et al. |
| 2009/0192518 A1 | 7/2009 | Golden et al. |
| 2009/0287291 A1 | 11/2009 | Becking et al. |
| 2009/0299393 A1 | 12/2009 | Martin et al. |
| 2010/0076452 A1 | 3/2010 | Sepetka et al. |
| 2010/0185210 A1 | 7/2010 | Hauser et al. |
| 2011/0166586 A1 | 7/2011 | Sepetka et al. |
| 2011/0288572 A1 | 11/2011 | Martin |
| 2012/0143230 A1 | 6/2012 | Sepetka et al. |

FOREIGN PATENT DOCUMENTS

| | | |
|---|---|---|
| EP | 1312314 A1 | 5/2003 |
| JP | 11-47140 | 6/1989 |
| JP | 62-49841 | 9/1994 |
| JP | 2007-522881 A | 8/2007 |
| JP | 2007-252951 A | 10/2007 |
| WO | WO 96/01591 | 1/1996 |
| WO | WO 96/19941 | 7/1996 |
| WO | WO 97/27808 | 8/1997 |
| WO | WO 97/27893 | 8/1997 |
| WO | WO 98/03120 | 1/1998 |
| WO | WO 00/72909 | 12/2000 |
| WO | WO 01/32254 | 5/2001 |
| WO | WO 01/67967 | 9/2001 |
| WO | WO 02/02162 | 1/2002 |
| WO | WO 02/28291 | 4/2002 |
| WO | WO 03/000334 | 1/2003 |
| WO | WO 03/061730 | 7/2003 |
| WO | WO 03/089039 | 10/2003 |
| WO | WO 2006/031410 | 3/2006 |
| WO | WO 2006/122076 | 11/2006 |
| WO | WO 2007/092820 | 8/2007 |
| WO | WO 2008/131116 | 10/2008 |
| WO | WO 2009/034456 | 3/2009 |
| WO | WO 2009/056482 | 7/2009 |
| WO | WO 2011/091383 | 7/2011 |
| WO | WO 2012/009675 | 1/2012 |
| WO | WO 2012/162437 | 11/2012 |

* cited by examiner

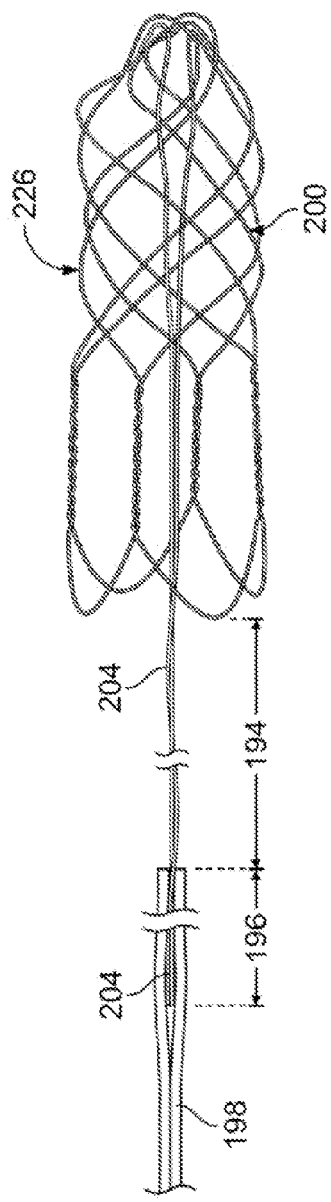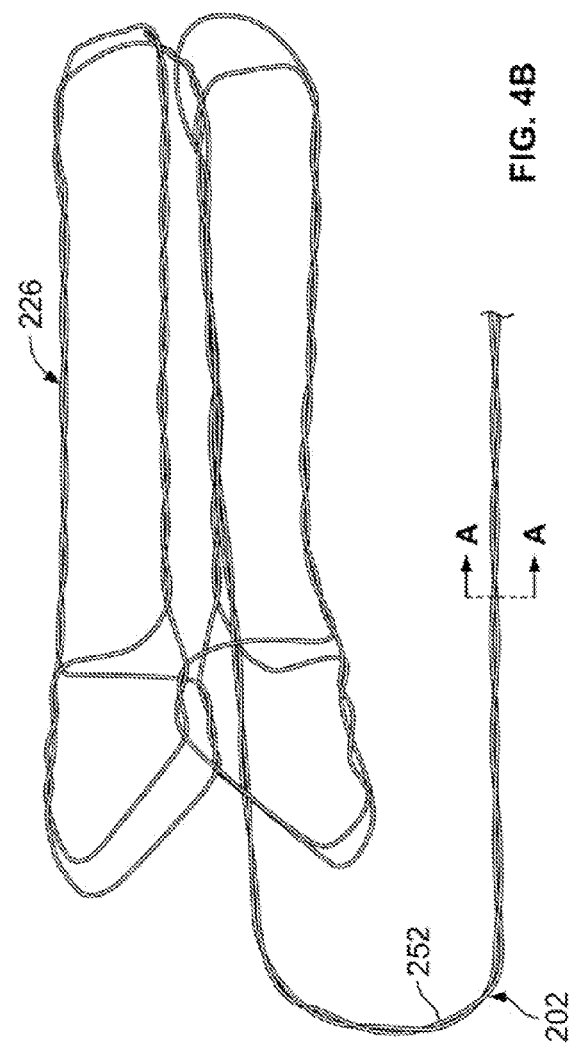

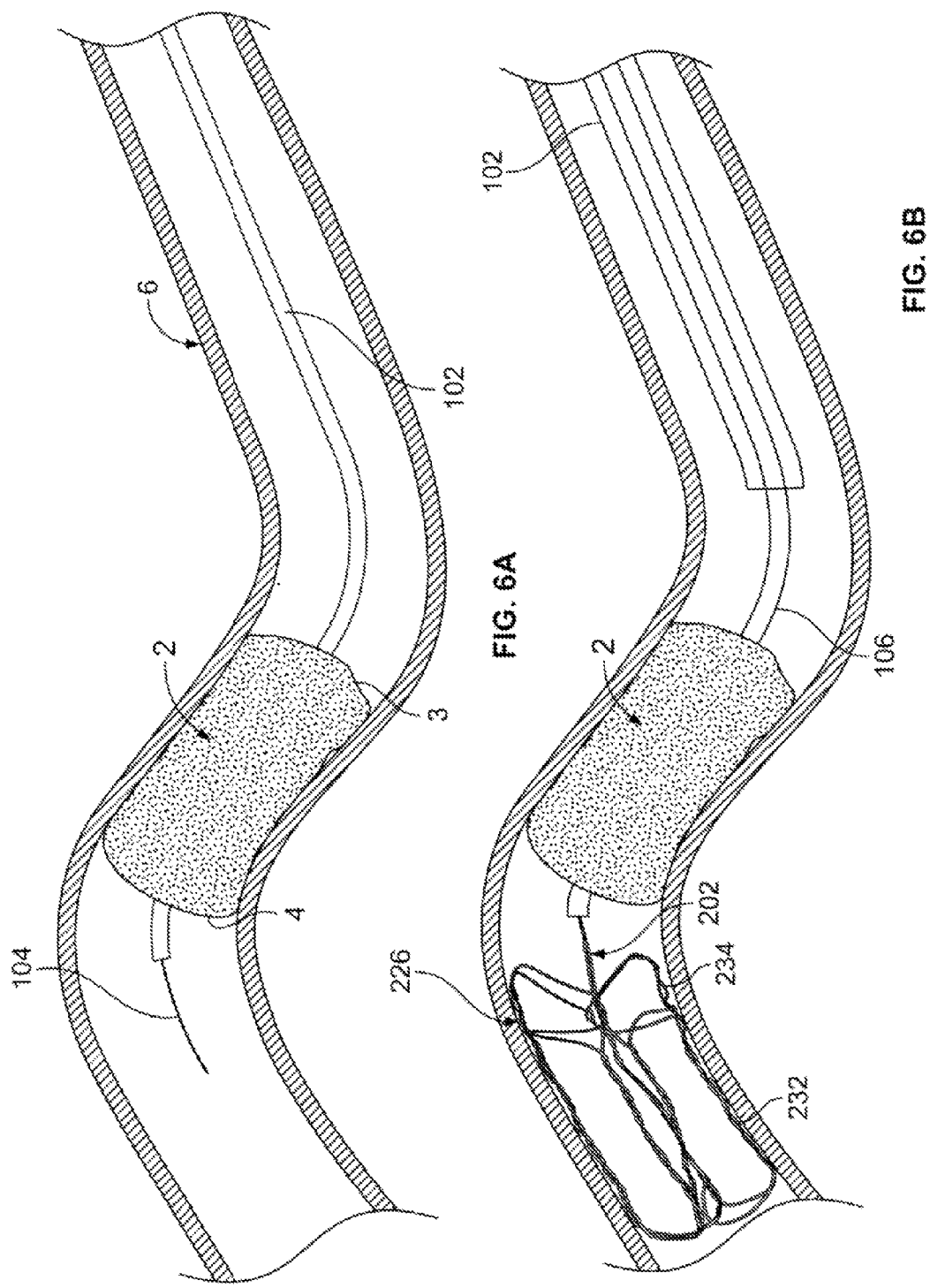

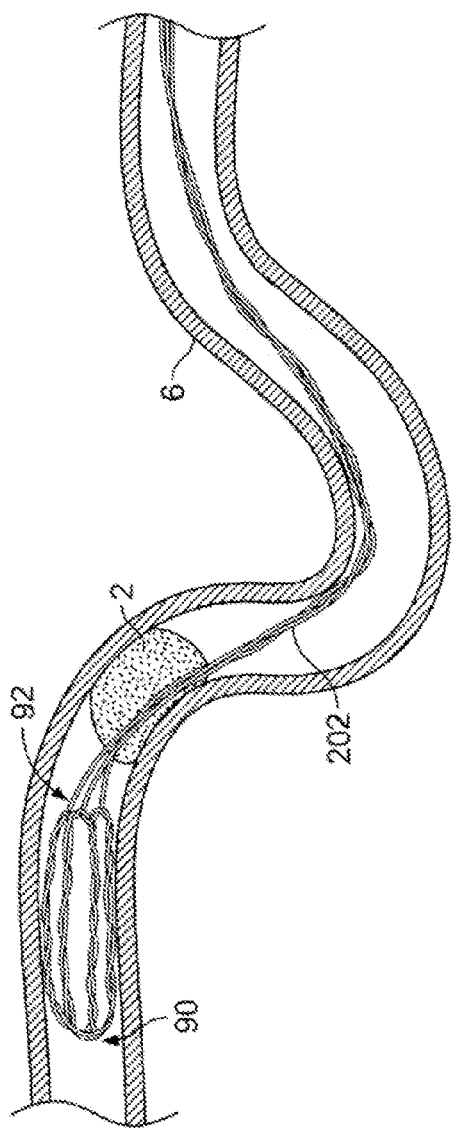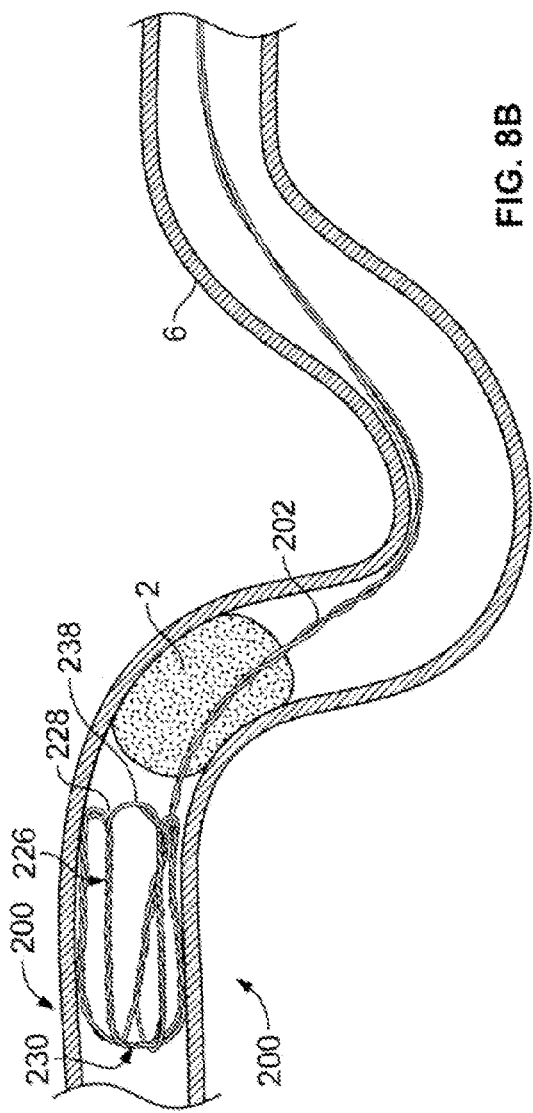

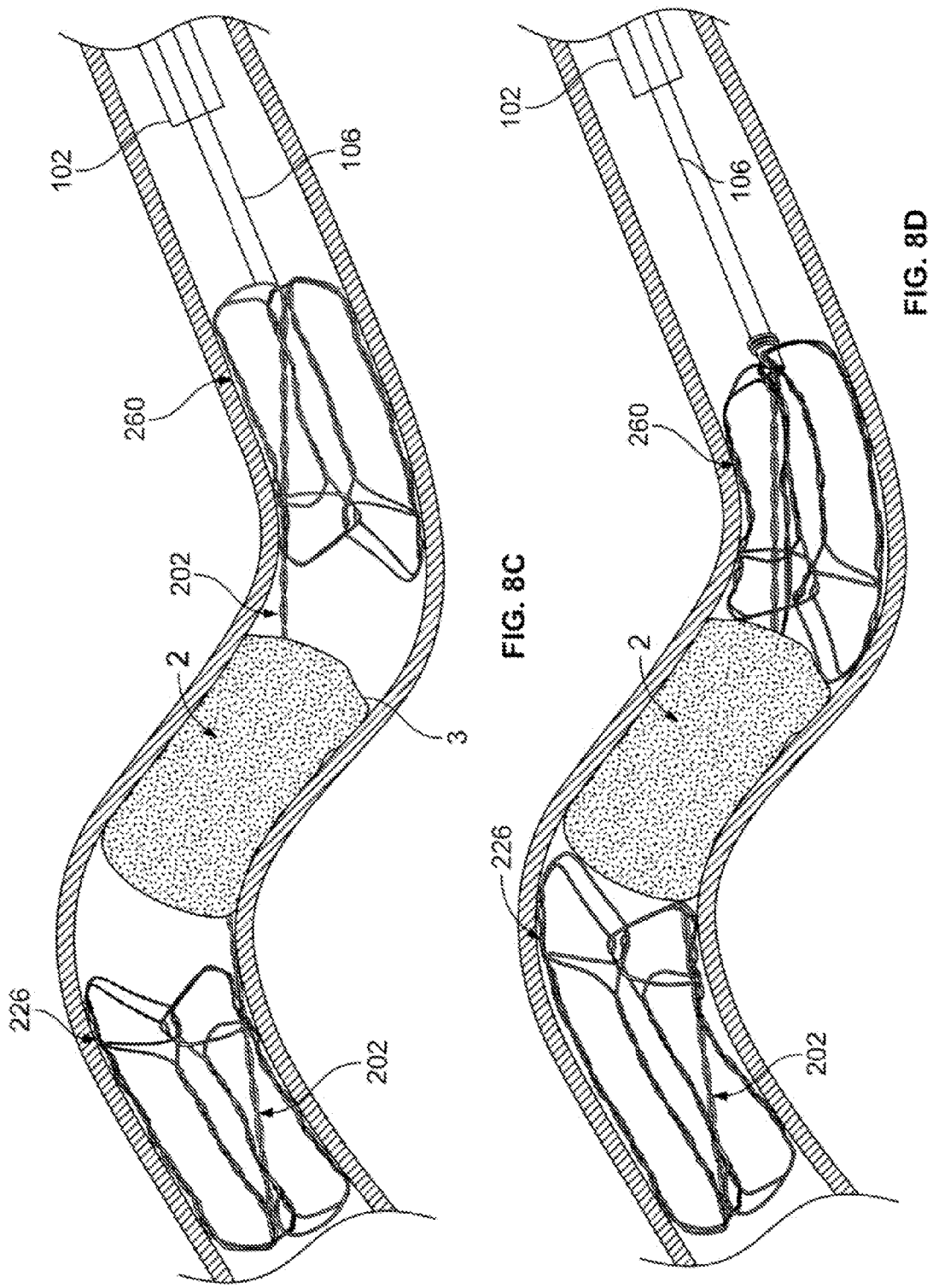

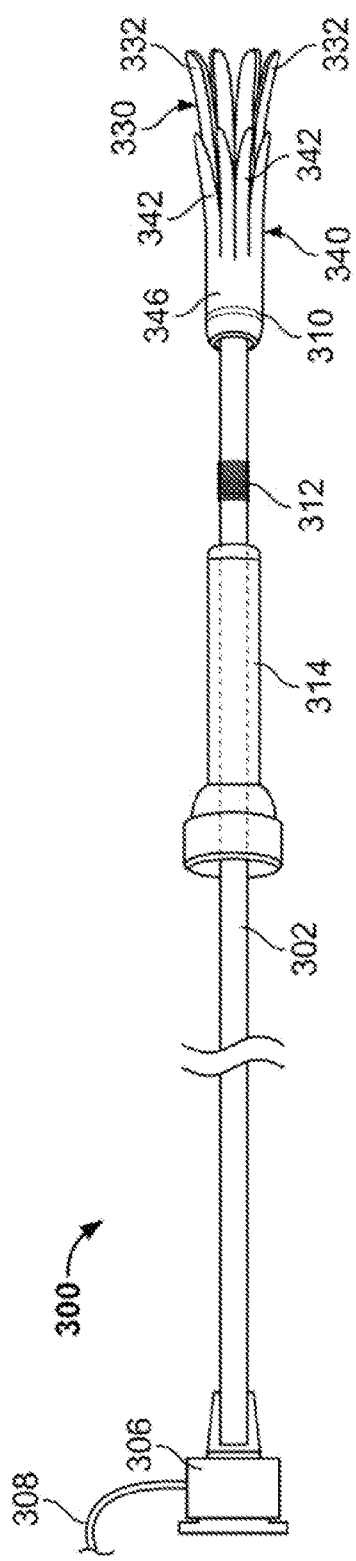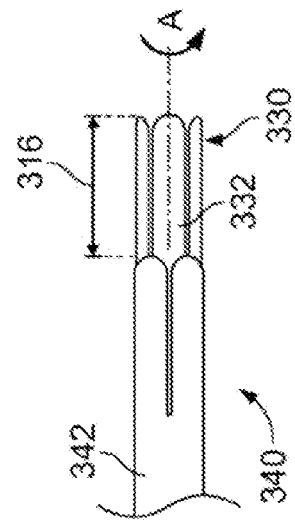
FIG. 11A
FIG. 11C
FIG. 11B

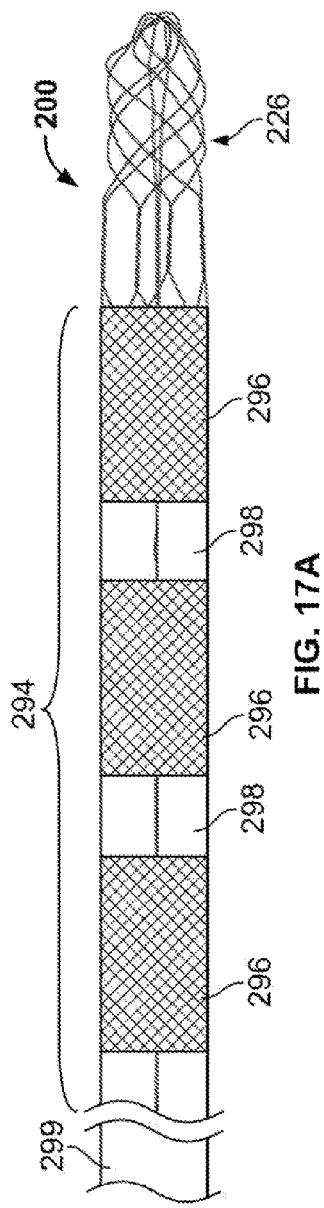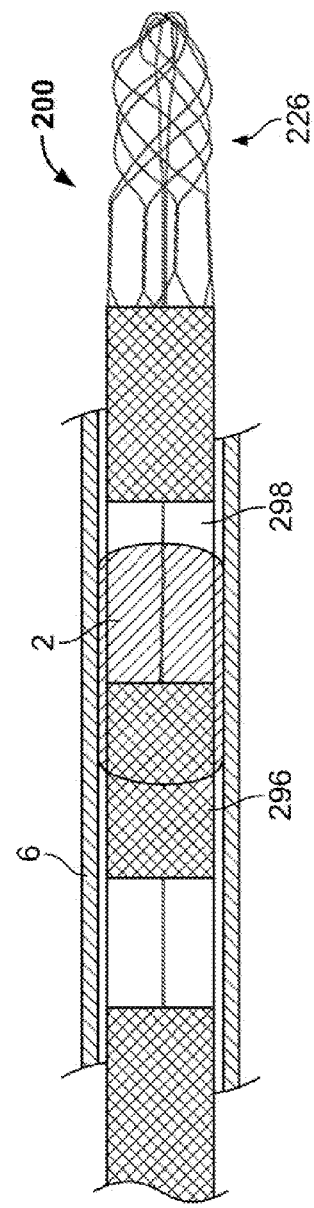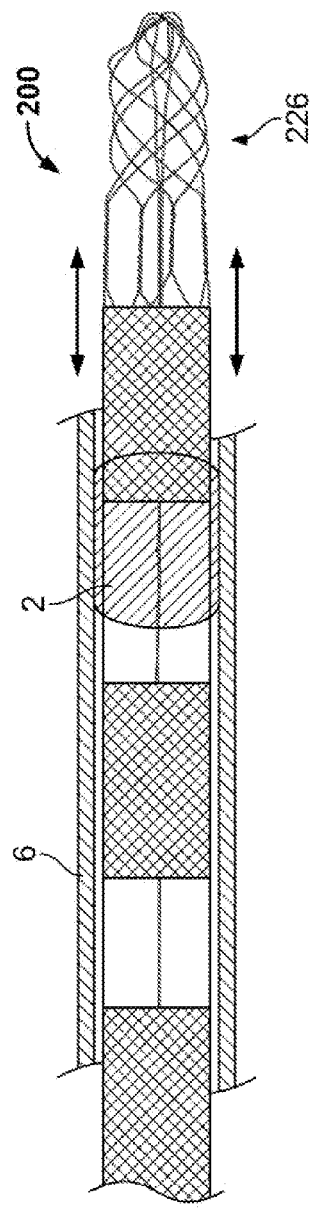

RETRIEVAL SYSTEMS AND METHODS FOR USE THEREOF

RELATED APPLICATIONS

This application is a continuation of International Patent Application No. PCT/US2010/026571 filed Mar. 8, 2010 which claims benefit of priority to U.S. Provisional Application Nos. 61/158,324 filed Mar. 6, 2009 and 61/171,419 filed Apr. 21, 2009, the contents of which are incorporated herein by reference in its entirety.

FIELD OF THE INVENTION

The devices described herein are intended to retrieve obstructions from the body. In a first variation, the devices are constructed in wire form where the wires diverge from a main bundle to form a variety of shapes that form a composite device. The benefit of such a diverging wire construction is that the composite complex device can be of a "joint-less" construction. Such devices have applicability through out the body, including clearing of blockages within body lumens, such as the vasculature, by providing a capturing portion that can envelop the obstruction to address the frictional resistance between the obstruction and body lumen prior to attempting to translate and/or mobilize the obstruction within the body lumen. In addition, the devices described below include features that prevent unwanted and premature mobilization of the obstruction when removing the obstruction through tortuous anatomy.

BACKGROUND OF THE INVENTION

Many medical device applications require advancement of device in a reduced profile to a remote site within the body, where on reaching a target site the device assumes or is deployed into a relatively larger profile. Applications in the cerebral vasculature are one such example of medical procedures where a catheter advances from a remote part of the body (typically a leg) through the vasculature and into the cerebral region of the vasculature to deploy a device. Accordingly, the deployed devices must be capable of achieving a larger profile while being able to fit within a small catheter or microcatheter. In addition, the degree to which a physician is limited in accessing remote regions of the cerebral vasculature is directly related to the limited ability of the device to constrain into a reduced profile for delivery.

Treatment of ischemic stroke is one such area where a need remains to deliver a device in a reduced profile and deploy the device to ultimately remove a blockage in an artery leading to the brain. Left untreated, the blockage causes a lack of supply of oxygen and nutrients to the brain tissue. The brain relies on its arteries to supply oxygenated blood from the heart and lungs. The blood returning from the brain carries carbon dioxide and cellular waste. Blockages that interfere with this supply eventually cause the brain tissue to stop functioning. If the disruption in supply occurs for a sufficient amount of time, the continued lack of nutrients and oxygen causes irreversible cell death (infarction). Accordingly, immediate medical treatment of an ischemic stroke is critical for the recovery of a patient.

Naturally, areas outside of ischemic stroke applications can also benefit from improved devices. Such improved devices can assume a profile for ultimate delivery to remote regions of the body and can remove obstructions. There also remains a need for devices and systems that can safely remove the obstruction from the body once they are secured within the device at the target site. Furthermore, there remains a need for such devices that are able to safely removed once deployed distally to the obstructions in the even that the obstructions is unable to be retrieved.

Furthermore, the techniques for treating strokes described herein can be combined with stenting as well as the delivery of clot dissolving substances.

The use of stents to treat ischemic stroke is becoming more common. Typically, a physician places an unexpanded stent across a clot and then expands the stent to compress the clot and partially open the vessel. Once the vessel is at least partially open, clot dissolving fluids, such as t-PA or urokinase, can be deployed through a microcatheter to further dissolve the clot. However, these fluids generally take a long time to dissolve clot (sometimes up to several hours). Thus, the use of these fluids has not been terribly effective at dissolving clot in vessels where a complete blockage occurs. The use of a stent allows immediate flow to the vessel, the fluid can then be administered over several hours to dissolve the clot. Once the clot dissolves, the stem can either be left in place (i.e., a permanent stent), or removed (i.e., a temporary stent).

However, once blood flow is restored, a portion of the clot dissolving substance is dispersed downstream of the clot via blood flow. This minimizes the contact time and amount between the fluid and the clot thereby decreasing the efficiency of the stent and fluid treatment.

The methods, devices and systems, address the problems described above.

SUMMARY OF THE INVENTION

The examples discussed herein show the inventive device in a form that is suitable to retrieve obstructions or clots within the vasculature. The term obstructions may include blood clot, plaque, cholesterol, thrombus, naturally occurring foreign bodies (i.e., a part of the body that is lodged within the lumen), a non-naturally occurring foreign body (i.e., a portion of a medical device or other non-naturally occurring substance lodged within the lumen.) However, the devices are not limited to such applications and can apply to any number of medical applications where elimination or reduction of the number of connection points is desired.

One variation of the device includes a medical device for removing an obstruction from a blood vessel, the medical device comprises a main bundle comprising a group of wires having a first end and a second end, a capturing portion formed by the group of wires and having a translating surface adjacent to a capturing surface, the translating surface having an open proximal end and the capturing surface having a permeable distal end, where the capturing portion is formed from the group of wires such that the group of wires diverges from the second end of the main bundle to form the permeable distal end, the group of wires extend back in a proximal direction to form the capturing surface, the translating surface, and open proximal end about the main bundle; and where the translating surface and capturing surface are configured so that a translating surface axial strength is greater than a capturing surface axial strength, wherein application of a tensile force on the main bundle causes axial compression of the capturing surface without causing axial compression and deformation of the translating surface sufficient to deform the translating surface as the capturing portion engages the obstruction.

The medical device can include a capturing surface that is configured to generate a spring force against the translating surface when a proximal force applied by the main bundle of wires compresses the capturing surface against the translating surface when encountering resistance from the obstruction, where the capturing surface is configured to have a sufficient axial stiffness to direct the spring force and proximal force to the open proximal end as the open proximal end engages the obstruction where the capturing surface is also sufficiently flexible to conform to a shape of the vessel.

In another variation, the capturing section is configured so that when the open proximal end of the translating section engages resistance equal to or greater than a threshold force, proximal movement of the leading wire inverts the capturing section within the translating section and reduces a size of the capturing section to enable the capturing section to re-enter a catheter.

In those variation of the device that are navigated in tortuous anatomy (such as the cerebral vasculature), the device can include a main bundle joined to a proximal bundle, where the proximal bundle comprises a stiffness greater than the main bundle and where the main bundle extends for at least a predetermined range from the permeable distal end to allow navigation of a distal portion of the medical device within the cerebral vasculature.

Another variation of the device includes a retrieval device for removing an obstruction from a body lumen, the system comprising at least one leading wire; a retrieval body comprising a translating section adjacent to a capturing section, the translating section having an open proximal end and the capturing section having a permeable distal end, where the leading wire is extends to a portion of the capturing section to permit articulation of the open proximal end relative to the leading wire; and where the translating section and capturing section are configured so that a translating section axial strength is greater than a capturing section axial strength, wherein application of a tensile force on the leading wire causes axial compression of the capturing surface without causing axial deformation of the translating surface when the retrieval body engages the obstruction.

Variations of the retrieval system can also include a sheath having a hub located at a proximal end, a proximal capture portion affixed to a distal end of the sheath, at least one leading wire extending through the sheath, where a distal section of the leading wire comprises a distal stiffness and where a proximal section of the leading wire comprises a proximal stiffness, where the proximal stiffness is greater than the distal stiffness, a distal capturing portion at the distal end of the leading wire, the distal capturing portion being axially moveable relative to the proximal capture portion, and an insertion tool slidably located over the sheath, the insertion tool comprising a gripping region affixed to a rigid section, where compression of the gripping portion creates a frictional fit between the insertion tool such that when the insertion tool is coupled to the catheter, compression of the gripping portion and axial movement of the insertion tool advances the sheath within the catheter.

In one variation of the devices described herein, the device comprises a main bundle or group of wires that diverge to form a device having various shapes but few or no connections points or joints (where fabrication of such a construction is referred to as "jointless"). Clearly, the inventive devices described herein are not limited to such a jointless construction. Additional variation includes one or more leading wires that are attached to a capturing portion as described below.

In another variation, the device includes a main bundle comprising one or a group of wires. The device also includes a capturing portion formed by the wires or wire of the main bundle. The capturing portion includes a cavity or space that is able to surround the obstruction. Accordingly, the capturing portion includes an open proximal end, a permeable distal end, and a capturing surface extending therebetween. The permeable distal end should be sufficiently permeable to allow blood to flow but have sufficient surface area to prevent escape of the obstruction or to prevent particles such as pieces of clot or emboli that would otherwise cause a complication if such pieces migrate through the body. In some variations of the device, the capturing portion is formed from the group of wires such that the group of wires diverges from the second end of the main bundle to form the permeable distal end, the group of wires extend back in a proximal direction to form the capturing surface and open proximal end about the main bundle. Although some closing of the open proximal end can occur, it will not be sufficient to interfere with the obstruction as the capturing portion moves over the obstruction. In some variations, the permeable end may be the distal end or be towards the distal end (meaning anywhere past a proximal end). The terms distal and proximal are relative to the physician (e.g., the distal end is the farthest end from the catheter/physician).

The devices of the present invention typically include a main bundle from which the wires extend. In most case, the main bundle extends for a length sufficient to withdraw the device from a body of a patient. Accordingly, in such cases, the main bundle shall extend through the length of a catheter. In alternate constructions, the main bundle may be affixed to a single wire or member. In such cases, a main bundle does not extend from the capturing portion to the exterior of the patient. Instead, a single wire extends to the operator interface of the device where the wire is affixed to a main bundle.

Devices of the present invention can incorporate any number of wires of different characteristics including, but not limited to, materials, shapes, sizes and/or diameters. Clearly, the number of permutations of device configurations is significant. Providing devices with such a composite construction allows for the manipulation of the device's properties to suite the intended application.

In an additional variation, the surface of the capturing portion can include a wire frame structure, a mesh, a single wound wire, a film, a membrane, a polymer covering, and a plurality of crossing wires or a heterogeneous mixing of these. In additional variations, a section of the capturing portion can include wires, while another section of the capturing portion can include a film. Clearly, any number of permutations is within the scope of this disclosure. In any case, the capturing surface should prevent the obstruction from escaping as the device is removed from the body. Clearly, the capturing surface can comprise any number of shapes or configurations.

As noted herein, the joint-less construction improves the flexibility and strength of the device by eliminating joints, connection points, or other attachment points. In addition, the joint-less construction improves the ability of the device to be delivered through a small microcatheter. As a result, the device and microcatheter are able to access remote regions of the vasculature.

The devices may be fabricated to be self-expanding upon deployment from a catheter. Alternatively, the devices can be constructed from shape-memory alloys such that they automatically deploy upon reaching a pre-determined transition temperature.

The devices of the present invention may also include features to prevent migration of the obstruction as the capturing portion encapsulates the obstruction. For example, a proximal foot (such as region of increased surface area) can be located on or in the catheter. In another variation, an additional capture portion is located on the catheter where the proximal end of this capture is a mesh, a single wound wire, a film, a membrane, a polymer covering, or a plurality of crossing wires affixed to or in the catheter. Accordingly, the capturing portions both envelope or surrounds the obstruction as they are moved together. As noted below, additional variations may allow for temporarily locking of the two capturing portions together for increase effectiveness in removing the obstruction from the body.

The capturing portions disclosed herein can include mechanical features that assist in removal of the obstruction. These features can be hooks, fibers, barb, or any such structure. Any portion of the capturing portion or even the device can have such hooks, fibers, or barbs that grip into the obstruction as the device surrounds the obstruction. It will be important that such features prevent the obstruction from sliding proximally but do not hinder the ability of the practitioner to remove the device from the body.

The operation of the devices and method described herein secure the obstruction, overcome the friction forces acting on the obstruction, and then remove the obstruction from the anatomy without losing or fractionating the obstruction. In a first variation, the inventive method includes advancing a catheter distal to the obstruction, deploying a first capturing portion distal of the obstruction, where the first capturing portion comprises a translating surface and a capturing surface, the translating surface having an open proximal end and the capturing surface having a permeable distal end, and at least one leading wire affixed to the capturing surface and extending through the capturing portion and through the catheter, where the translating surface and capturing surface are configured so that a translating surface axial strength is greater than that of a capturing surface axial strength, proximally moving the leading wire to compress the capturing surface without compressing the translating surface such that the translating surface gradually advances over the obstruction, and removing the obstruction and first capturing portion from the blood vessel Additional variations of the method include (1) passing a catheter distally to the obstruction by passing either through the obstruction and/or between the obstruction and the vascular wall; (2) deploying a first capturing portion distally to the obstruction and the catheter is withdrawn proximal to the obstruction; (3) the capturing portion is then translated over the obstruction by withdrawing the main bundle. Since the main bundle is affixed to a distal end of the capturing portion, misalignment between the bundle and the capturing portion does not cause distortion of the open proximal end. Since the open proximal end remains expanded against the lumen wall, the capturing portion can then be advanced over the obstruction.

The method and systems may also include the use of an additional capturing portion having an open distal end. This configuration allows the first capturing portion and second capturing portion to envelop or ensnare the obstruction from both the proximal and distal sides. Additional variations even allow for temporarily locking the two capturing portions together. Such a feature increases the ability to remove the obstruction from the body It should be noted that reference to surrounding, capturing or securing the obstruction includes partially and/or fully surrounding, engulfing, encapsulating, and/or securing the obstruction. In any case, a portion of the device engages the obstruction prior to translation of the obstruction within the lumen.

It should be noted that in some variations of the invention, all or some of the device can be designed to increase their ability to adhere to the obstruction. For example, the wires may be coupled to an energy source (e.g., RF, ultrasonic, or thermal energy) to "weld" to the obstruction. Application of energy to the device can allow the surrounding portion to deform into the obstruction and "embed" within the obstruction. Alternatively, the device can impart a positive charge to the obstruction to partially liquefy the obstruction sufficiently to allow for easier removal. In another variation, a negative charge could be applied to further build thrombus and nest the device for better pulling force. The wires can be made stickier by use of a hydrophilic substance(s), or by chemicals that would generate a chemical bond to the surface of the obstruction. Alternatively, the filaments may reduce the temperature of the obstruction to congeal or adhere to the obstruction.

Additional variations of the invention include a reentry device for withdrawing an object into a distal end of a sheath, the reentry device comprising a elongate member having a distal portion and a lumen extending therethrough, a plurality of first tines arranged circumferentially at the distal portion, the plurality of first tines each having a distal end forming a first discontinuous funnel where the distal end of each first tine is spaced from the distal end of an adjacent first tine, wherein the first discontinuous funnel is collapsible upon withdrawal into the distal end of the sheath, a second funnel spaced proximal to the first funnel, where the second funnel is collapsible upon withdrawal into the distal end of the sheath, and wherein a distal perimeter of the first discontinuous funnel shape is distal to a distal perimeter of the second funnel.

Another variation of a device as described herein includes methods and devices for recanalizing a blood vessel having an obstruction. The obstructions can vary from fully blocking flow to partially blocking flow in the blood vessel. In addition, the devices and methods can only recanalize the blood vessel or can also remove the obstruction.

In one example, the device includes a distal capturing portion having an open proximal end and a fluidly permeable distal end, the distal capturing portion having a translating surface adjacent to the open proximal end and a distal capturing surface adjacent the fluidly permeable distal end; a proximal capturing portion having an open distal end and a fluidly permeable proximal end, the proximal capturing portion having a medial surface between the open distal end the fluidly permeable proximal end, where the medial surface comprises a stent-type structure that is configured to expand to compress the obstruction when deployed therein; and a main bundle comprising a group of wires having a first end and a second end extending through the proximal capturing portion to the distal capturing portion, where the main bundle is moveable relative to the proximal capturing portion such that proximal movement of the main bundle decreases a distance between the open ends of the distal capturing portion and proximal capturing portion.

The device can optionally include a proximal capturing portion configured to include at a plurality of fluid delivery ports on a surface proximal capturing portion allowing fluid to be delivered from a perimeter of the proximal capturing portion.

In some variations, the devices described herein can include at least one filament forming the proximal capturing portion, the filament including at least one fluid delivery passage extending therethrough and in fluid communication with the fluid delivery ports.

The medial surfaces of the proximal capturing portion can comprise stent-like structures. For example, they can include mesh patterns or braided structures.

Another variation of a method for recanalizing a blood vessel having an obstruction includes inserting an expandable structure within the obstruction, where the expandable structure comprises at least one fluid delivery port adjacent to an exterior surface of the expandable structure; expanding the expandable structure within the obstruction; and delivering a substance through the fluid delivery port such that the substance begins to dissolve the obstruction.

One variation of the method includes the use of an expandable structure that is fabricated from at least one tubular element, the tubular element comprising a fluid delivery passage extending through at least a portion of the tubular element, where the fluid delivery passage terminates in at least one of the fluid delivery ports.

In another variation, the expandable structure comprises a stein portion and a fluid delivery tube or membrane located within the stent portion, where expanding the expandable structure comprises expanding the stent portion and where delivering the substance comprises delivering the substance through at least one delivery port located in the fluid delivery membrane.

The method can also include withdrawing the proximal capturing portion proximally to the obstruction and then surrounding the obstruction with the distal capturing portion and the proximal capturing portion to capture the obstruction.

The method can also include using the distal capturing portion to assist in compressing the obstruction by withdrawing the distal capturing portion against the expandable structure when the expandable structure is located in the obstruction to cause the expandable structure to increase a radial force to the obstruction.

In another variation, the expandable structure comprises a distal capturing portion having a fluid permeable distal end and a proximal stent section, where the proximal stent section comprises a plurality of high density stent sections and a plurality of low density of stent sections, where expanding the expandable structure comprises expanding the proximal stent section into the obstruction.

Another variation of the present invention also includes a method of recanalizing a blood vessel having an obstruction by advancing a microcatheter distal to the obstruction; deploying a distal capturing portion distally of the obstruction; positioning a proximal capturing portion within the obstruction, where the proximal capturing portion is sized to have a greater length than a length of the obstruction and where proximal capturing portion expands to compress a portion of the obstruction against the vessel; moving the proximal capturing portion toward to the obstruction; securing the obstruction by moving the distal capturing portion and the proximal capturing portion together; and removing the obstruction from the blood vessel.

As noted herein, the methods can include a capturing portion structure (sometimes referred to as a medial surface) that comprises a stent portion having a fluid permeable proximal end. The stent portion can comprise a structure that expands against an obstruction to assist in recanalizing the vessel.

In one variation, withdrawing the proximal capturing portion comprises resheathing at least a section of the proximal capturing portion within a microcatheter during withdrawal of the proximal capturing portion. A segment of the proximal capturing portion can be deployed from the microcatheter proximal to the obstruction such that the partially deployed segment functions as a proximal basket.

Any variation of the methods described herein can optionally include delivering a substance to the obstruction where the substance is configured to dissolve the obstruction. In such cases the delivering the substance to the obstruction can comprise delivering the substance through the microcatheter or delivering the substance through a surface of the proximal capturing portion.

The present disclosure also includes methods of recanalizing a blood vessel having an obstruction by advancing a catheter distal to the obstruction; deploying a first capturing portion distally of the obstruction, where the first capturing portion comprises a permeable distal end, an open proximal end, a capture surface extending therebetween, and at least one leading wire extending through the capturing portion and through the catheter; positioning a second capturing portion within the obstruction, the second capturing portion having an open distal'end and a fluidly permeable proximal end, and a medial surface extending therebetween, such that the second capturing portion compresses a portion of the obstruction against the blood vessel; withdrawing the second capturing portion proximal to the obstruction; capturing the obstruction between the first and second capturing portions by moving the first capturing portion over the obstruction by pulling on the leading wire to apply a force to the capturing portion at a location distal to the open proximal end of the first capturing portion; and removing the obstruction from the blood vessel.

The present disclosure also include a method of removing an obstruction from a blood vessel using a stent structure having high density section and low density section. For example, a variation of the method can include inserting an expandable structure within the obstruction, where the expandable structure comprises a distal capturing portion having an open proximal end and a fluid permeable distal end, and a proximal stent section, where the proximal stent section comprises a plurality of high density stent sections and a plurality of low density of stent sections, where the high density stein sections comprise a high surface area of a mesh, or a woven pattern; and expanding the expandable structure within the obstruction such that one or more high density stent sections engage the obstruction. In an additional variation, the expanded expandable structure can be withdrawn or reciprocated within the vessel to break the obstruction free or shear portions of the obstruction.

Additional devices and methods for treating ischemic stroke are discussed in commonly assigned U.S. patent application Ser. Nos. 11/671,450 filed. Feb. 5, 2007; 11/684,521 filed Mar. 9, 2007; 11/684,535 filed Mar. 9, 2007; 11/684,541 filed Mar. 9, 2007; 11/684,546 filed Mar. 9, 2007; 11/684,982 filed Mar. 12, 2007, 11/736,526 filed Apr. 17, 2007, 11/736,537 filed Apr. 17, 2007, and 11/825,975 filed Sep. 10, 2007; the entirety of each of which is incorporated by reference. The principles of the invention as discussed herein may be applied to the above referenced cases to produce devices useful in treating ischemic stroke. In other words, the wire-shaped construction of devices according to present invention may assume the shapes-disclosed in the above-referenced cases when such a combination is not inconsistent with the features described herein.

BRIEF DESCRIPTION OF THE DRAWINGS

Each of the following figures diagrammatically illustrates aspects of the invention. Variation of the invention from the aspects shown in the figures is contemplated.

FIG. 4A illustrates a variation of a capturing portion having a main bundle that extends beyond a certain distance to provide a device having an extremely flexible distal region and a relatively stiff proximal region with a strong joint region that will be sufficiently spaced from tortuous anatomy during use of the device.

FIG. 4B illustrates a main bundle having a curved or shaped portion.

FIGS. 6A to 6B illustrate an example of traversing an obstruction with a sheath to deploy a distal capturing portion.

8F illustrates a device after securing an obstruction between proximal and distal capturing sections.

Figure 9:
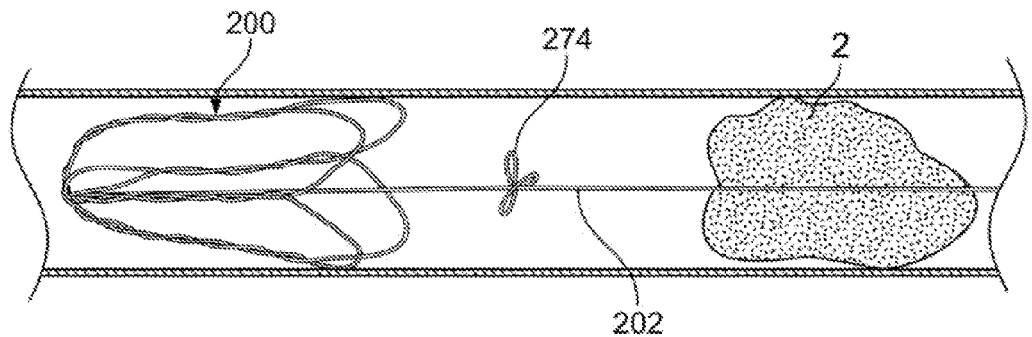

FIG. 9 illustrates a main bundle as including an increased surface area or medial foot that is used to dislodge or loosen the obstruction from a wall of the body passage.

Figure 10:
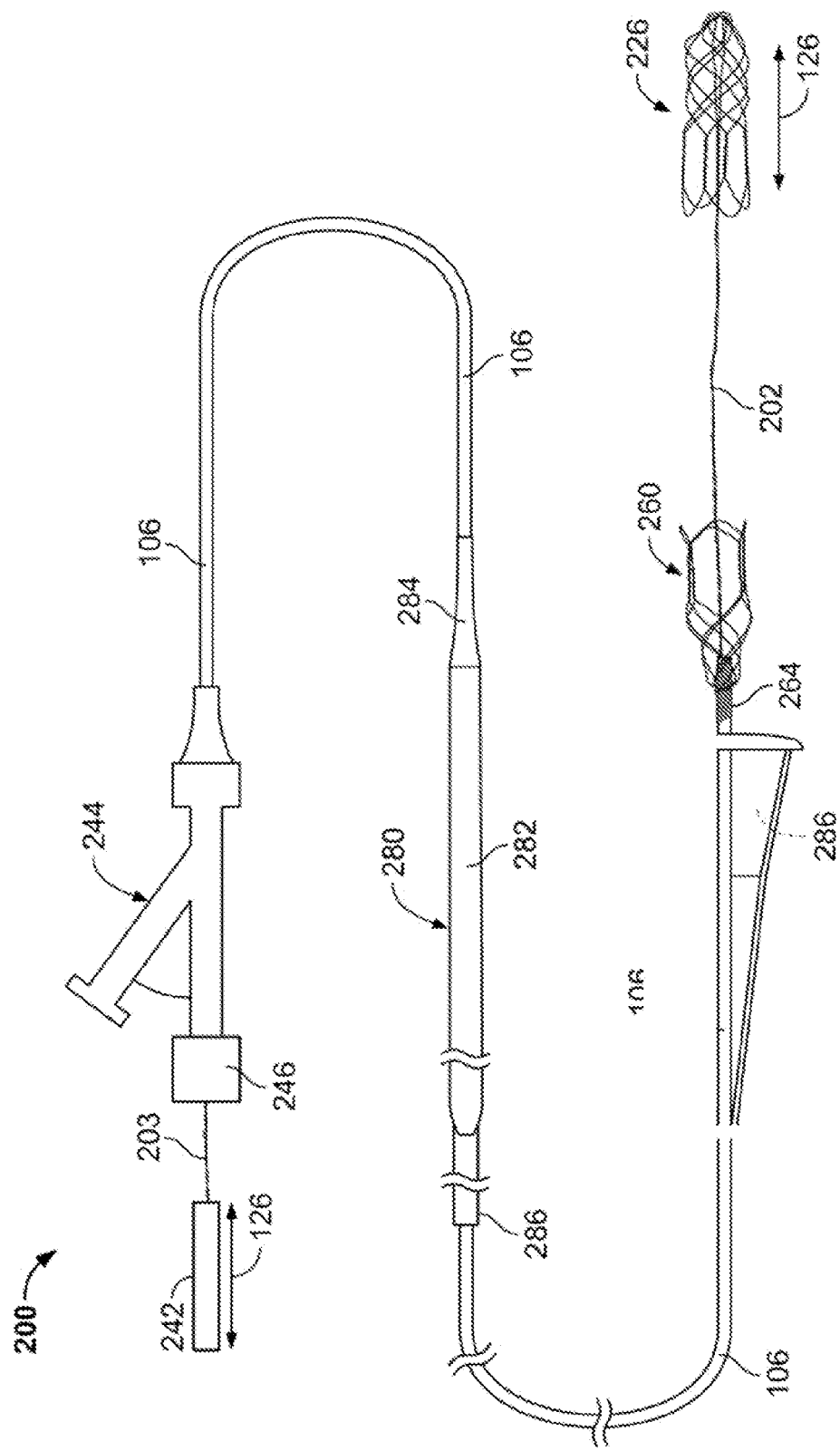

FIG. 10 illustrates a variation of a proximal and distal end of a retrieval device.

FIGS. 11A to 11C illustrate a variation of a funnel catheter useful for retrieving objects from vessels or body lumens.

Figure 12A:
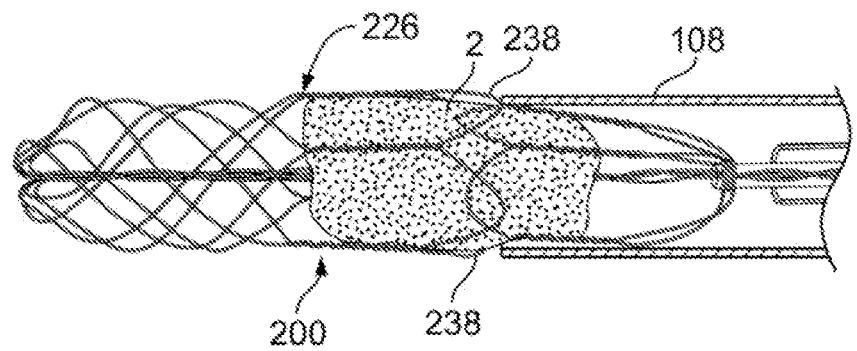

FIG. 12A shows an example of a retrieval device getting caught on a guide sheath.

Figure 12B:
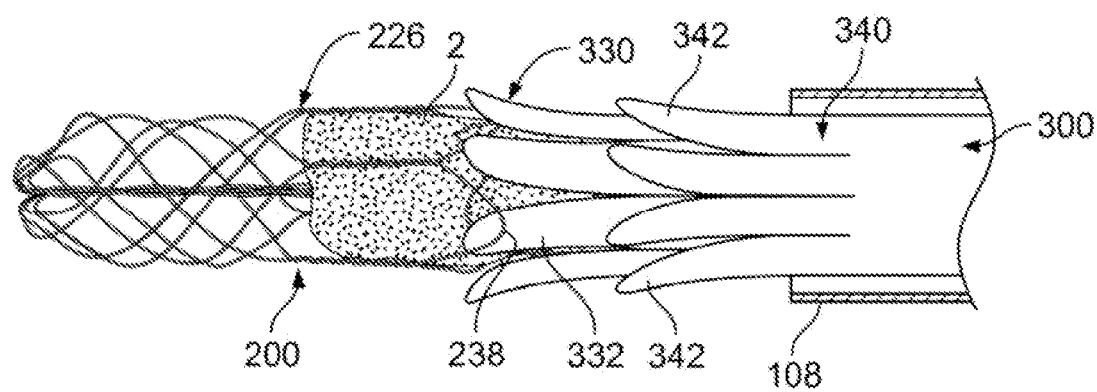
Figure 12C:
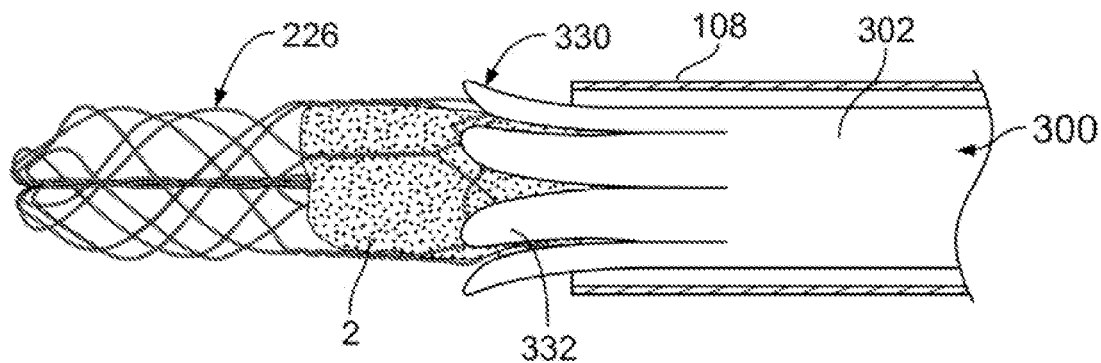
Figure 12D:
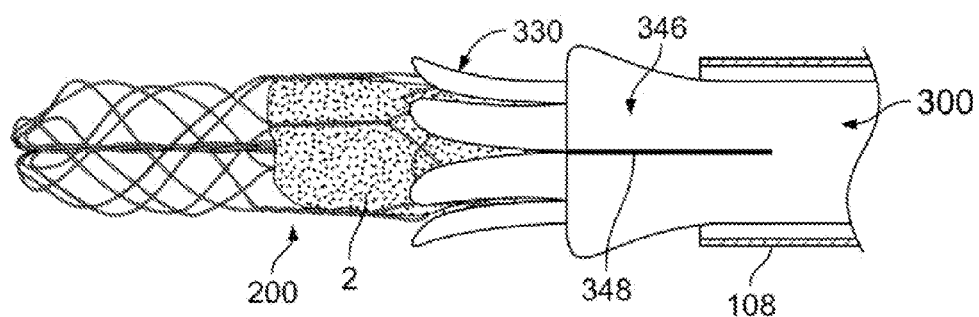

FIGS. 12B to 12D provide illustrative examples of funnel catheter used for removal of an obstruction.

FIG. 13A to 13G illustrates another variation of a funnel catheter using a mesh or layer of material to form a funnel.

FIGS. 14A to 14D illustrate additional concepts to prevent or minimize flaring of the distal capture portion so that it may be withdrawn into a guide sheath.

Figure 15:
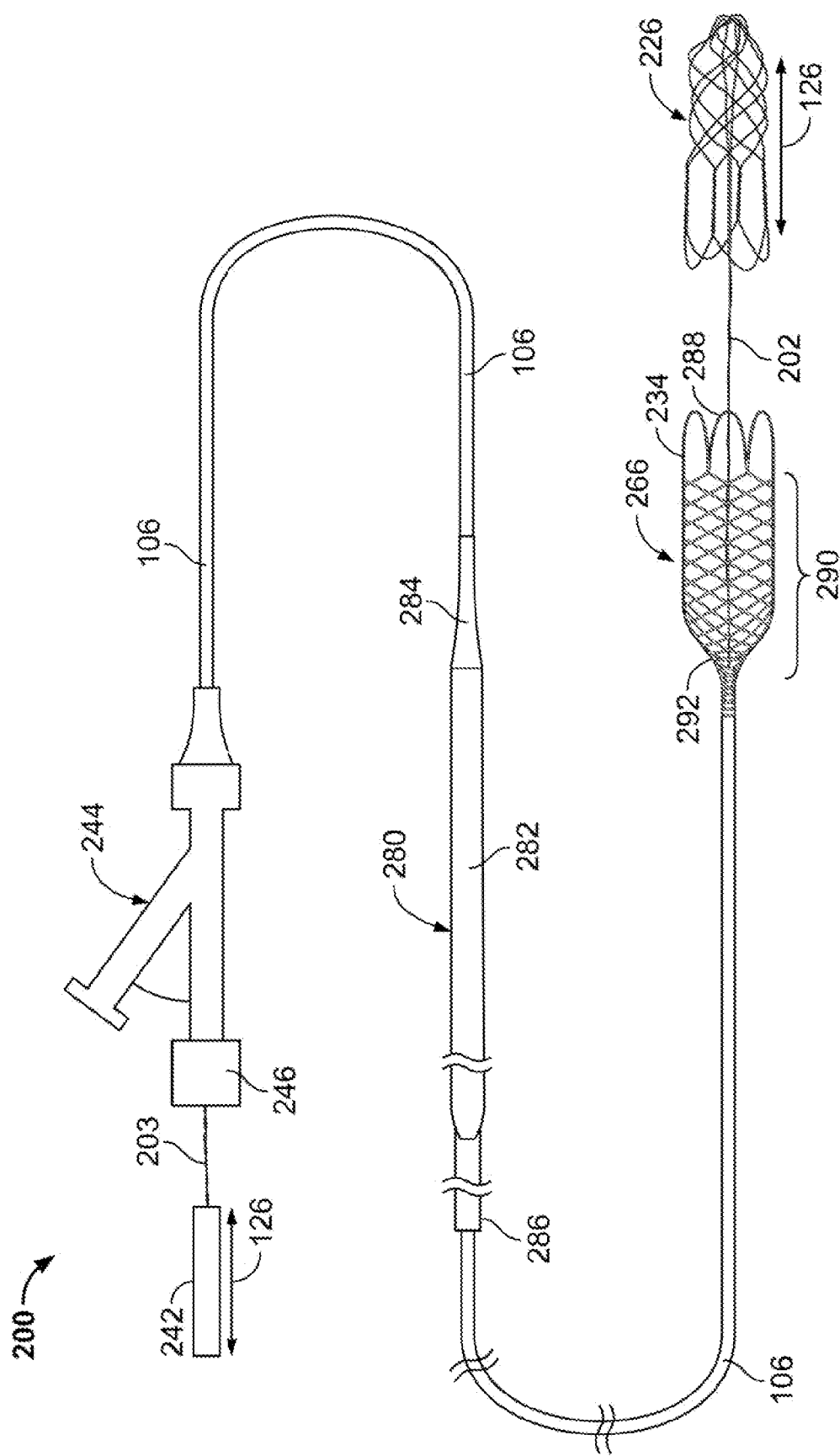

FIG. 15 illustrates another variation of a distal basket and a proximal capturing portions where the proximal capturing portion comprises a stent-like structure.

FIGS. 16A to 16E show a retrieval device that uses a proximal capture portion that is configured to be deployed against an obstruction within a vessel or other lumen.

FIGS. 17A to 17C illustrate a variation of a working portion of an obstruction removal device having a distal capturing portion affixed to a proximal section comprising one or more high density sections interconnected with one or more low density sections.

FIGS. 18A to 18H illustrate variations of capture portion that are configured to deliver a substance at a perimeter of the device so that the substance can be deployed closely to the obstruction.

DETAILED DESCRIPTION

It is understood that the examples below discuss uses in the cerebral vasculature (namely the arteries). However, unless specifically noted, variations of the device and method are not limited to use in the cerebral vasculature. Instead, the invention may have applicability in various parts of the body. Moreover, the invention may be used in various procedures where the benefits of the method and/or device are desired.

Figure 1A:
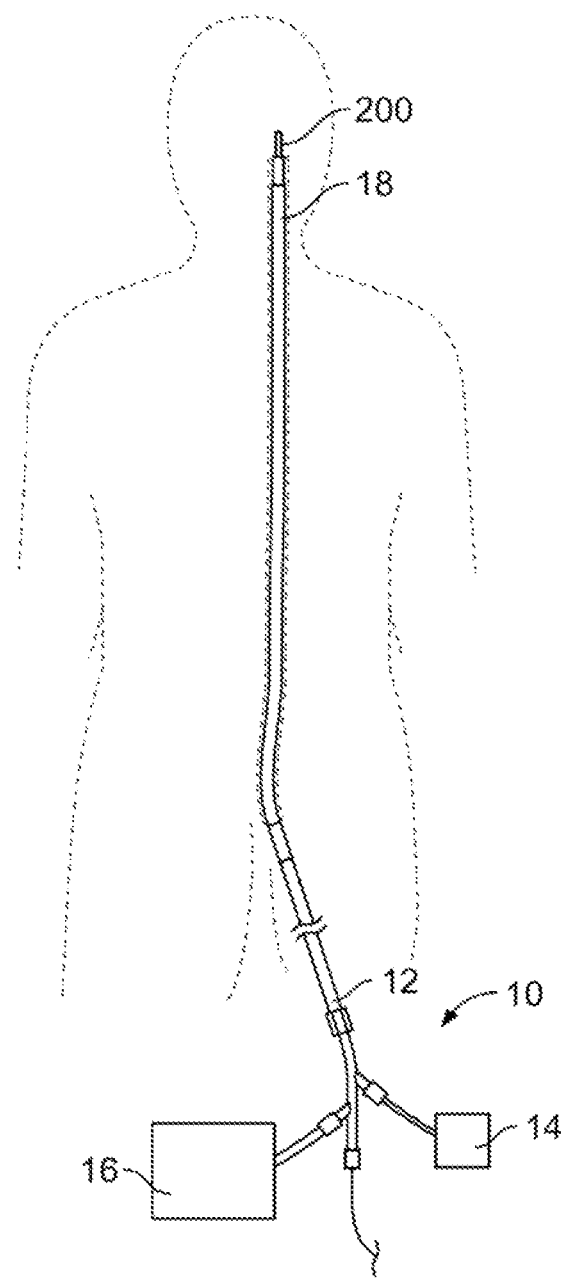
FIG. 1A illustrates an example of a device according to the present invention when used in a system for removing obstructions from body lumens.

FIG. 1A illustrates a system 10 for removing obstructions from body lumens as described herein. In the illustrated example, this variation of the system 10 is suited for removal of an obstruction in the cerebral vasculature. Typically, the system 10 includes a catheter 12 microcatheter, sheath, guide-catheter, or simple tube/sheath configuration for delivery of the obstruction removal device to the target anatomy. The catheter should be sufficient to deliver the device as discussed below. The catheter 12 may optionally include an inflatable balloon 18 for temporarily blocking blood flow or for expanding the vessel to release the obstruction.

It is noted that any number of catheters or microcatheters maybe used to locate the catheter/microcatheter 12 carrying the obstruction removal device 200 at the desired target site. Such techniques are well understood standard interventional catheterization techniques. Furthermore, the catheter 12 may be coupled to auxiliary or support components 14, 16 (e.g., energy controllers, power supplies, actuators for movement of the device(s), vacuum sources, inflation sources, sources for therapeutic substances, pressure monitoring, flow monitoring, various bio-chemical sensors, bio-chemical substance, etc.) Again, such components are within the scope of the system 10 described herein.

In addition, devices of the present invention may be packaged in kits including the components discussed above along with guiding catheters, various devices that assist in the stabilization or removal of the obstruction (e.g., proximal-assist devices that holds the proximal end of the obstruction in place preventing it from straying during removal or assisting in the removal of the obstruction), balloon-tipped guide catheters, dilators, etc.

Figure 1B:
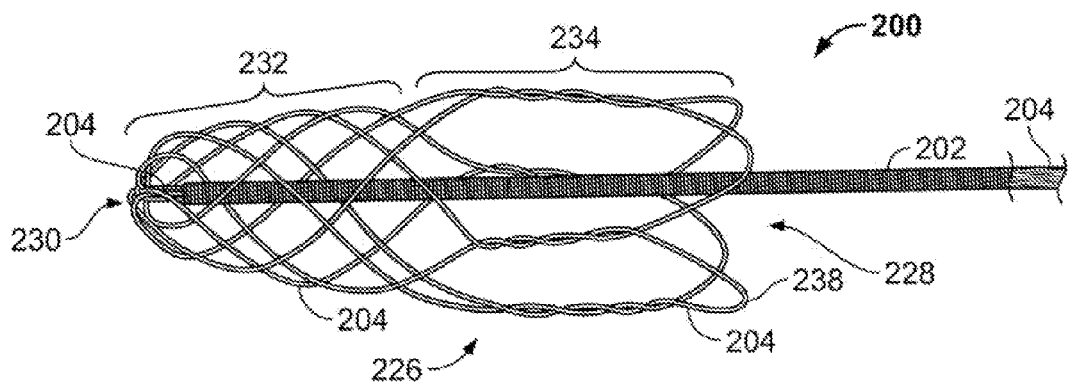
FIG. 1B illustrates a first example of an obstruction removal medical device.

FIG. 1B illustrates a first example of an obstruction removal medical device according to the features described herein. As shown, the device 200 generally includes capturing portion 226 comprising a translating section/surface 222 and a capturing section/surface 224. In the illustrated variation, the translating section 222 shown comprises a wire framework. However, any number of configurations is within the scope of this disclosure. In many variations of the device, the translating section 222 provides a low friction surface so that it translates over the obstruction without significantly moving the obstruction. This permits the capturing portion 226 to envelop or surround the obstruction prior to attempting to move the obstruction within the body lumen. As noted herein, the translating section 222 attempts to reduce the outward radial force applied by the obstruction against the wall of the lumen during movement of the obstruction within the lumen.

FIG. 1B illustrates a distal section of the capturing portion 226 that serves as a capturing section/surface 232. The capturing section 232 has an increased frictional surface (in this variation illustrated by the crossing 204 wires) so that it can capture and ultimately remove the obstruction. The frictional surface of the capturing section 232 can also be described as an increased coverage density. In essence, as the frictional surface of capturing section 232 coverage density increases, there is a greater "device" surface area to interact with the obstruction. In some variations the capturing section 232 increases in frictional surface between the translating section 234 and the end of the device 200.

As shown, the device 200 includes a main bundle 202 comprising a group of individual leading wires 204. In this variation, the bundle of leading wires 204 is surrounded by a coil or coiled wire 205. The coiled wire 205 can comprise a single leading wire that joins the device 202. Alternatively, the coiled wire 205 can extend terminate or wrap back prior to forming the capture portion 226. Moreover, the coiled wire 205 can extend throughout a length the main bundle 202, or along one or more segments of the main bundle 202.

While the example shows the group consisting of four individual leading wires 204, the bundle 202 can have any number of leading wires. In various examples 2, 4, or 8 wires were used to construct the device. In certain variations, the number of wires in the main bundle loop around from the capturing portion. For example, if 2 leading wires are used to construct the device, then when constructing the main bundle 202 2 wires are set to extend distally towards the capturing portion, where the 2 wires are then shaped to form the capturing portion. Eventually, the wires then loop back to extend proximally away from the capturing portion. Therefore, the 2 wires are doubled in the main bundle to create 4 separate wires in the main bundle.

The individual wires 204 themselves may be comprised of a number of different "micro" filaments, wires, or a single type of wire. Variations of the wires 204 are discussed in detail below; however, the wires 204 can be strands, filaments, or any similar structure that is able to be joined to form the device. The bundle 202 may be braided, wrapped, twisted, or joined in any manner such that they do not separate or become unbundled except where desired. For example, wires in any section of the device 200 can be bonded together (e.g., with epoxy, a polymeric coating, weld, solder, and/or adhesive, etc.) to prevent the wires from separating during deformation of the device as it deploys or removes the obstruction. In addition, the main bundle 202 can incorporate any number of features to assist in orienting the device 200 within the body passage. For example, the main bundle 202 can include a pre-set bend that would bias the capturing portion 226 in a desired orientation upon deployment as discussed below.

As also discussed below, variations of the present device 200 include capturing portions 226 where the translating section 234 provides a greater axial strength than an axial strength of the capturing section 232. The axial strength (e.g., column strength) determines whether the respective section of the capturing portion 226 compresses when the device 200 encounters resistance from an object and as a proximal or pulling force is applied through the main bundle or leading wire 202. In use, the translating section 234 resists axial compression and deformation so that it can locate about the obstruction. While the nature of moving the translating section will place the structure in a state of compression, there will be no visible deformation or deflection that prevents the translating section from advancing across an obstruction.

There are a number of approaches to adjust the axial strength of a capturing section 232 as well as the entire structure. In a first example, the manner in which the leading wire is wound to form the respective surface 232, 234 impact the respective axial strength. As shown, the traversing section 234 comprises a series of wrapped wires extending in an axial direction. This axial alignment causes the wires to oppose axial forces and thus increases the axial strength of the traversing section 234 relative to the capturing section 232. In the latter section, the wires 232 extend in a helical direction about the section 232. Thus there is less resistance to an axial load when compared to the traversing section 234.

Alternatively, or in combination, additional techniques can produce a device 200 with a capturing portion 226 that has sections of varying axial strength. In one example, the wire diameter can be adjusted to produce the desired column strength. Generally, for a given construction, a larger diameter wire increases the column strength of the section. In addition, larger diameter leading wires can terminate at the translating section 234 to permit smaller diameter wires to form the capturing section 232. In another example, the leading wire 204 composition can be selected to produce the desired axial strength. For example, drawn filled tube (DFT) wire has 30% platinum 70% nitenol. Decreasing the amount of platinum and increasing the nitenol increases the wire strength and results in higher column strength. In yet another example, the respective section, or the entire capturing portion 226, can be processed to produce the desired axial strength. For example, changing the annealing profile (e.g., temp, time) affects the wire strength, and therefore the axial strength.

Variations of devices 200 described herein can have capturing portions with alternate configurations than those shown in above. The capturing portion 226 can include constructional designs such as a basket, a filter, a bag, a coil, a helical wire structure, a mesh, a single wound wire, a film, a membrane, a polymer covering, or a plurality of crossing wires. In variations of the device, the capturing portion 226 is sufficiently permeable to allow blood or other fluid flow therethrough. As noted above, capturing portion 226 may be any structure that covers, encapsulates, engulfs, and/or ensnares the obstruction either fully or partially. Accordingly, although the capturing portion 226 is illustrated as a filter/bag, the wires may diverge to form a coil, helical shape, other mesh structure, or any other structure that defines a space that can be translated over the obstruction to ultimately remove the obstruction 2.

The capturing portion 226 can include an open proximal end 228, a permeable distal end 230 and a capturing surface 232 located therebetween. The capturing surface 232 of the capturing portion 226 defines a volume, cavity, or space that is able to cover, encapsulate, envelop, engulf, ensnare and/or surround the obstruction. Generally, the term traversing wire or filament refers to the section of leading wire 204 that forms the traversing surface 238. Generally, the traversing wires form the capturing surface 238 and then form the open proximal end 228. As discussed herein and illustrated below, the open proximal end 228 expands within the lumen, typically to the lumen walls, so that the obstruction enters the open proximal end 228 as the bundle 202 (or leading wire) translates the device 200 proximally.

The permeable distal end 230 is typically sufficiently porous so that fluid or blood may flow through. However, the end 230 is sufficiently closed (or has an increased surface area) so that the obstruction should not escape through the distal end 230 of the device 200. This construction typically causes the obstruction to become ensnared within the capturing portion 226 and prevented from passing through by the permeable distal end 230.

Figure 1C:
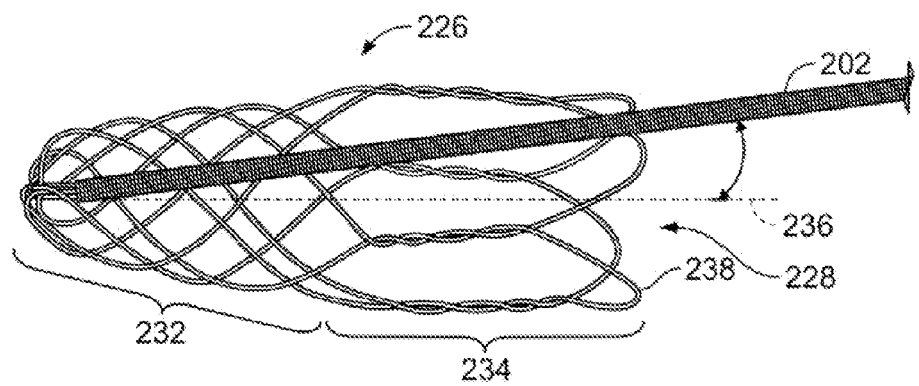
FIG. 1C illustrates the obstruction removal device articulating relative to leading wires (or a main bundle) without deforming an open end of the capturing portion.

As shown in FIG. 1C, an important feature of the present devices 200 is that the main bundle 202 and capturing portion 226 can articulate relative to one another without interfering with the size or profile of the open proximal end 228. This feature is described more fully below. As shown, the main bundle 202 extends through the open proximal end 228 and through at least a the traversing section 234 capturing portion 226.

FIG. 1C illustrates a condition where the main bundle 202 and capturing portion 226 articulate relative to one-another. Because the main bundle 202 joins the capturing section 232 at a distance from the open proximal end 228 movement of the main bundle 202 relative to an axis 236 of the capturing portion 226 does not reduce a profile of the open proximal end 228. If the main bundle 202 were affixed or connected to the open proximal end 228, then any movement of the bundle 202 away from the capturing portion's axis 236 would exert a force on the open end. This force, in turn, would cause the open end to narrow or deform. By doing so, the open end would not be able to uniformly expand against the lumen wall to capture the obstruction.

Turning now to the construction of the device 200, as shown above, the main bundle or a leading wire 202 extends beyond the open proximal end 228 and forms the capturing portion. In one variation, the construction of the device relies on converging/diverging wires to form continuous shapes so that the device is completely joint or connection free. However, as noted herein, the leading wire or main bundle 202 can be affixed to a structure that forms the capturing portion via an attachment point, joint, or junction. In addition, the structures forming the capturing portion can be fabricated from such processes as laser cutting of tubes, etching, metal injection molding, or any other such process.

The devices of the present invention can also include additional features to aid in removal of obstructions. For example, as shown in FIGS. 1B to 1C, the open proximal end 228 can include one or more petals or flanges 238 extending radially outward. The flanges 238 allow device 200 to have a flared structure at the open proximal end 228. In one example, the capturing portion 226 can be slightly oversized relative to the body passage containing the obstruction or slightly larger than the capturing portion. The flanges 238 provide an additional force against the wall of the passage to ensure that the device 200 is able to surround or encapsulate the obstruction. In yet another feature, in variations of a system having a proximal and distal capturing portion, the flanges can serve to lock the proximal and distal capturing portions together once they encapsulate or surround an obstruction. This feature minimizes the chance that the obstruction escapes from the capturing portions as the device and obstruction are removed from the body lumen.

In additional variations, the main bundle can diverge to form the capturing portion in multiple locations so long as the capturing portion's ability to articulate is not sacrificed. For example, the main bundle can diverge in several locations along the capturing surface (not shown).

FIGS. 1B to 1C also shows an integrally formed reinforcement ring 240 located along the length of the capturing surface 232 (i.e., on the traversing wires). The reinforcement ring 240 can be a separate or discrete ring located on or in the capturing surface 232. Alternatively, or in combination, the reinforcement ring 240 can be a ring shape that is integrally formed through arrangement of the wires 204 (as show in FIGS. 1B to 1C). The reinforcement ring 240 assists in expanding the device when deployed in the body lumen and/or prevents the device (e.g., the open proximal end) from collapsing as the device moves within the lumen to secure the obstruction. The reinforcement ring 240 can comprise a single wire, or a twisted pair of wires. Alternatively, the rings do not need to extend entirely circumferentially around the capturing surface. Instead, a reinforcement portion may extend between adjacent traversing wires but does not necessarily extend around the circumference of the capturing section. As noted herein, reinforcement portions may extend between adjacent traversing wires in multiple locations.

Figure 2A:
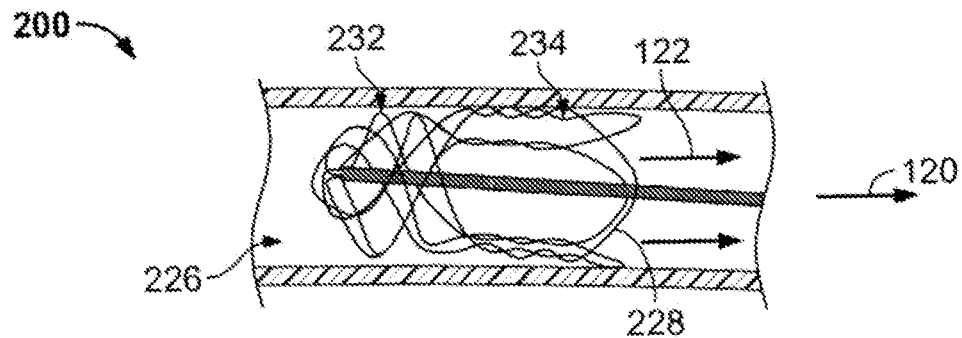
FIGS. 2A to 2E show a capturing portion for use with systems described herein where the capturing portion has sections of varying axial strengths. Such features can optionally be designed to provide a spring force when a section of the capturing portion is compressed and/or staged inversion of the capturing portion so that it can be removed through an immovable obstruction.
Figure 2B:
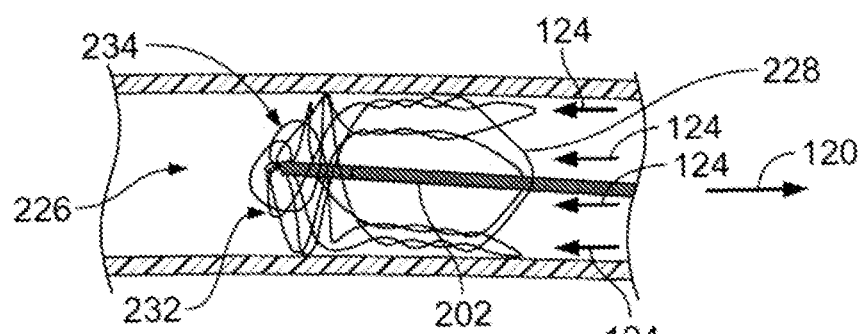

FIGS. 2A to 2E, show several benefits of varying axial strengths of the different sections of a capture portion 226. As shown in FIG. 2A, when the physician retrieves the capturing portion 226 by pulling on the leading wire or main bundle 202 (as shown by arrow 120), the entire capturing portion 226 translates as shown by arrow 122. However, when the device 200 encounters resistance (as schematically shown by force arrows 124) the lesser axial strength of the capturing section 232 causes axial deformation or compression of the capturing section 232 (as shown by FIG. 2B). In certain variations, the capturing section 232 can be constructed to function as spring such that deformation of the capturing section 232 stores energy. Accordingly, the physician can pull the main bundle 202 to build energy in the capturing section 232, then relax the force on the main bundle 202. The stored energy in the capturing section 232 gradually drives the open proximal end of the translating section 234 over or along the obstruction. The physician can apply this "pull and relax" technique repeatedly until the obstruction is sufficiently captured by the capturing portion 226.

Figure 2C:
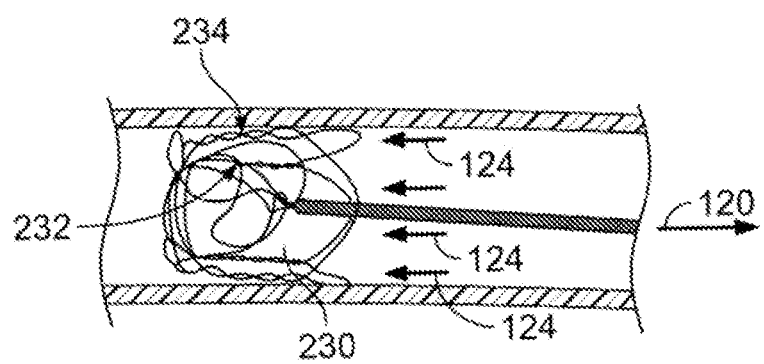
Figure 2D:
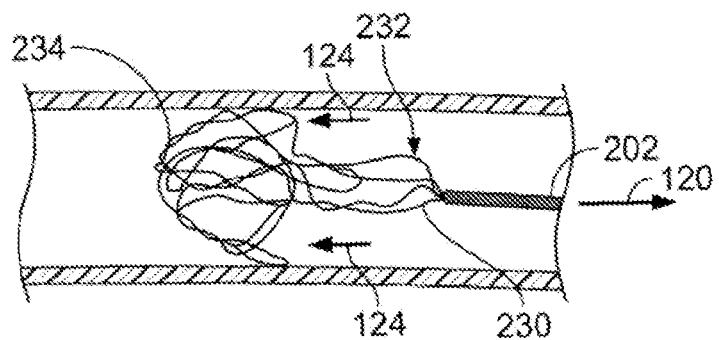
Figure 2E:
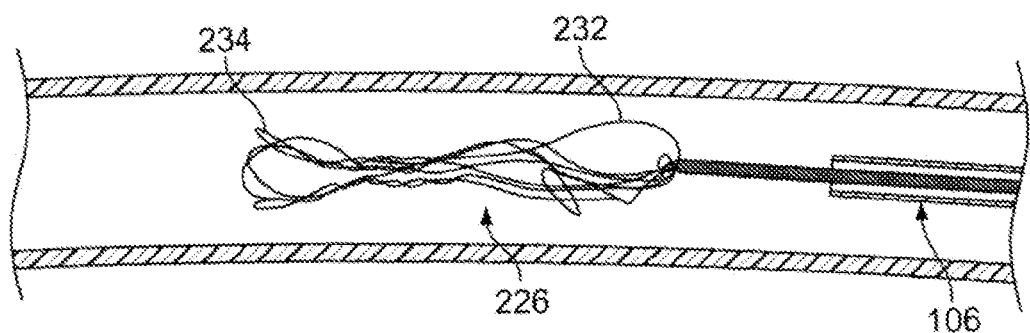

FIG. 2C shows an additional safety benefit given the varying axial strengths of the different sections of a capture portion 226. In the event the capturing portion 226 encounters an excessive degree or threshold of force (as denoted by arrows 124), the reduced axial strength of the capturing section 232 can invert within the translating section 234. As shown, the permeable distal end 230 of the capturing section 232 inverts and is pulled by the main bundle 202 within the translating section 234 and reduces in size. As shown in FIG. 2D, continued pulling on the main bundle 202 causes eventual inversion of the translating section 234 so that the capturing section 232 extends through the translating section 234 and the permeable distal end 230 is now proximal to the translating section 234. Continuing to apply move the main bundle 202 in a proximal direction 120 inverts the capturing portion 226 as shown in FIG. 2E. As shown, the translating section 234 is now distal to the capturing section 232. This causes a reduction in the size of the capturing portion through inversion of the capturing portion 226. This feature permits withdrawal of the capturing portion 226 within a delivery sheath 106 or through an immobile obstruction (as discussed below). As shown below, the ability to sequentially invert the capturing portion 226 and reduce its diameter enables retrieval of the device if deployed distal to atherosclerotic plaque or an immobile object where continued pulling against the object could cause damage or tearing of the body passage or vessel wall. It was found that retrieval devices that are not constructed with regions of varying axial strength, spring function, or staged inversion can often flatten or expand in diameter when attempting to retrieve the device though an immobile or stubborn obstruction.

Figure 3A:
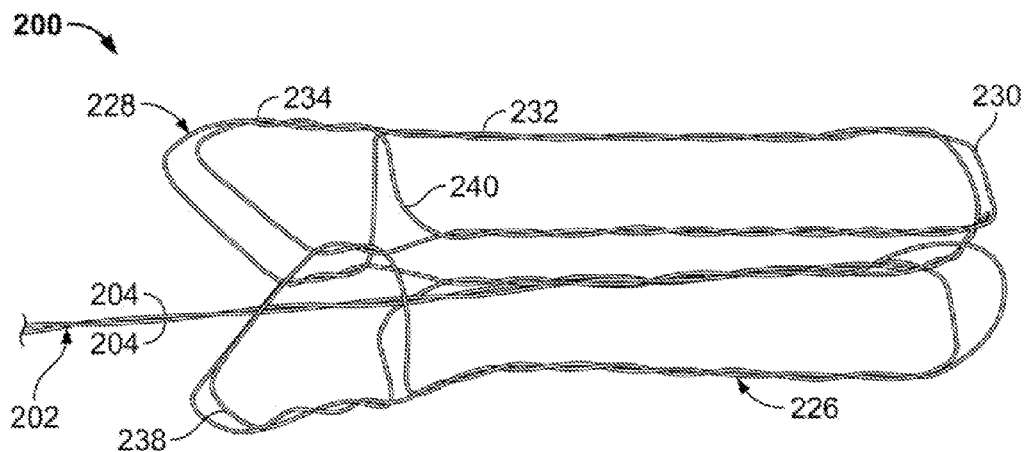
FIG. 3A illustrates a first variation of the device having a joint-less construction of a capturing portion that articulates about a main bundle of wires.

FIG. 3A illustrates an additional variation of a capturing portions 226 according to the present disclosure. In FIG. 3A, the main bundle 202 and the group of wires 204 branch or diverge at the permeable distal end 230 to form the capturing portion 226. In additional variations, the main bundle 202 can branch or diverge within a mid-portion of the capturing surface 232 rather than at the permeable distal end 230. In such a case, the wires 204 form the capturing surface 232 first and ultimately branch to form the remainder of the capturing portion. In any case, by extending through the open proximal end 228, the main bundle 202 is able to articulate relative to the capturing portion 226 without significantly reducing a profile of the open distal end 228. As discussed above, the capturing surface 232 of these variations is fabricated (either through processing or wire construction) to have an axial strength that is lower than that of the traversing section 234.

Figure 3B:
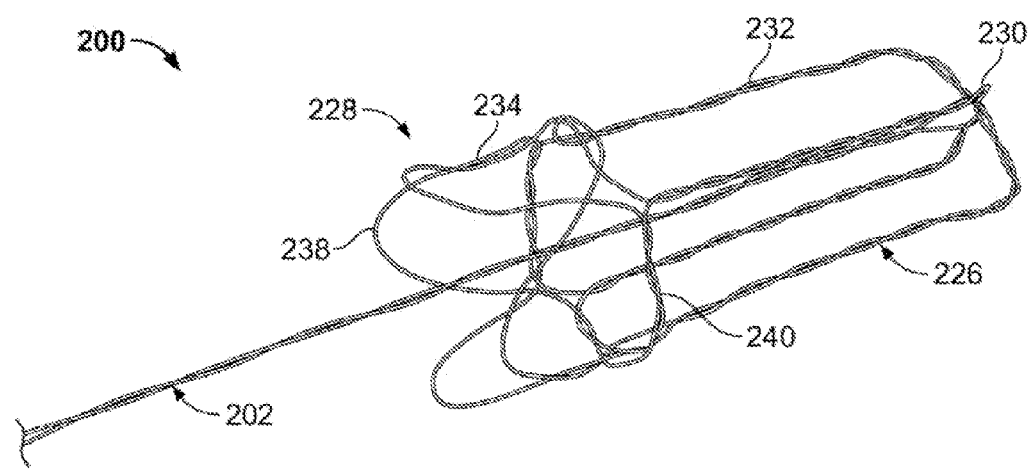
FIGS. 3B to 3H illustrate various constructions of capturing portions for use in the present invention.

FIG. 3B illustrates a variation having an integrated reinforcement ring 240. Typically, the reinforcement ring 240 provides radial strength to the capturing portion 226 to prevent collapse or deformation that would otherwise interfere with enveloping the obstruction. A reinforcement ring 240 may allow for use of wires that would otherwise provide unacceptable radial strength. For example, the reinforcement ring 240 may permit use of smaller diameter wires thereby allowing the device 200 to compress to a smaller diameter during delivery via a catheter.

In addition to the reinforcement ring 240, FIG. 3B includes an open proximal end 228 having a number of petals/flanges 238. In this variation, although the flanges 238 intersect one another, they are independently moveable.

Figure 3C:
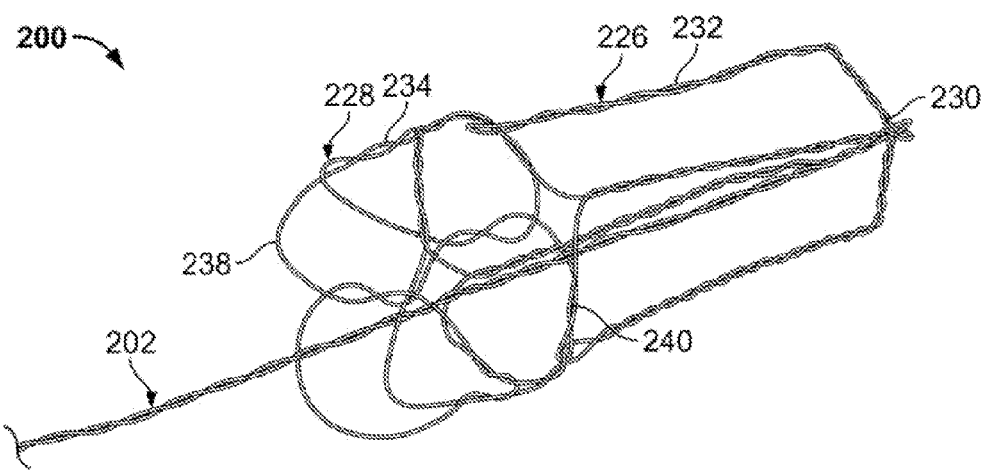

FIG. 3C shows a variation of a device 200 where the capturing portion 226 includes flanges 238 that are interwoven or connected with adjacent flanges 238. (Variations include bonding or otherwise joining the adjacent flanges together.) This feature provides the flanges 238 with a higher radial strength that reduces the likelihood that the flanges 238 bend or distort when moving in the body lumen or removing the obstruction.

Figure 3D:
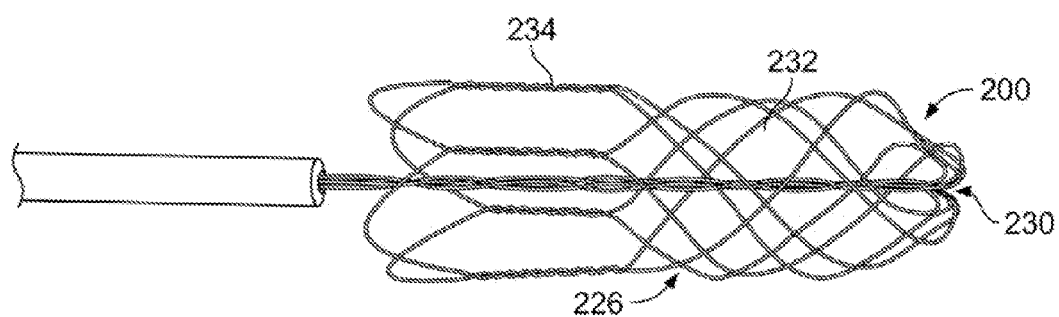
Figure 3E:
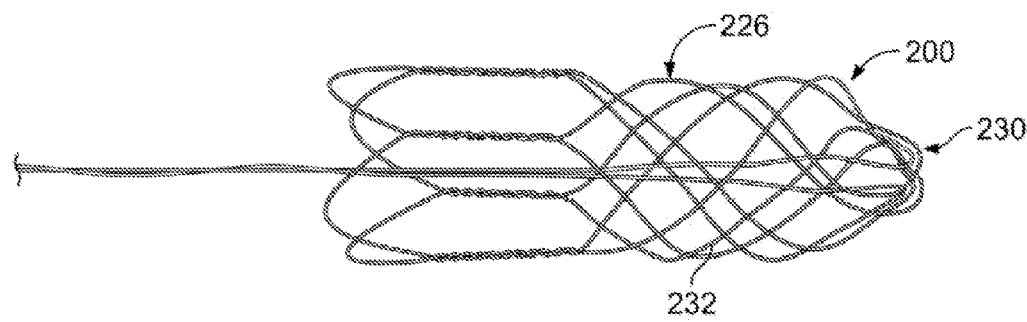

FIGS. 3D to 3E illustrate additional variations of devices having capturing portions 226 that have a basket type configuration. As shown, the capturing portions 226 and surface 232 comprise a denser mesh of traversing wires that ultimately lead to the traversing section 234 that terminates in flanges 238 at the open proximal end 228. In such variations, a first portion of the traversing surface 232 that is adjacent to the open proximal end has a low coverage density relative to the remaining portion of the capturing surface having a higher coverage density that eventually forms the permeable distal end 230. This construction lowers the lowering frictional resistance of the first portion of the capturing surface when moving over or against the obstruction but allows the remaining portion of the capturing surface to encapsulate and secure the obstruction.

As shown in FIG. 3E, the wires diverge from the main bundle towards the distal end of the capturing portion 226 to form the permeable distal end 230. The permeable distal end 230 can actually have the same configuration as the capturing surface 232. In other words, the permeable distal end can simply be an extension of the capturing surface that extends over the distal end of the capturing portion.

Naturally, the divergence of the wires can occur over a length of the capturing portion 226 rather than immediately at the distal end. For example, as show in FIG. 3D, the wires diverge towards a mid-section of the capturing portion and ultimately form the permeable distal end 230.

Figure 3F:
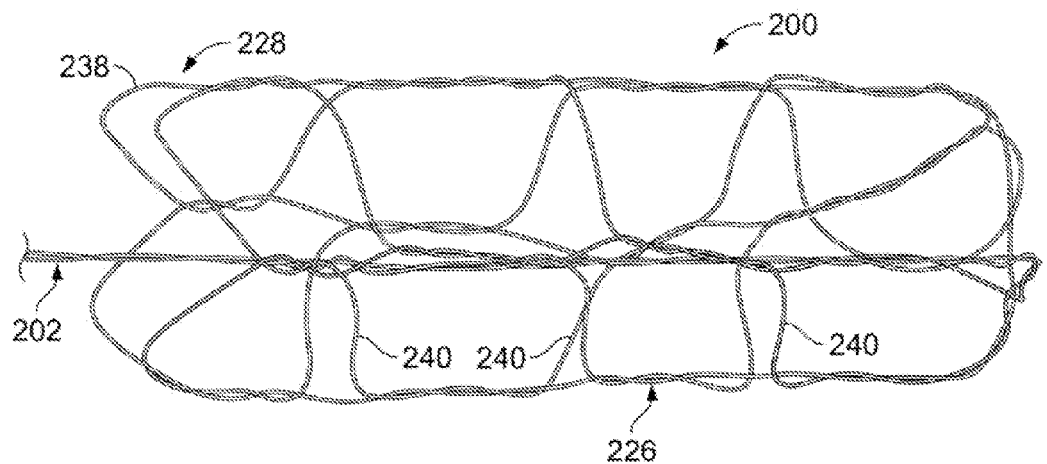

FIG. 3F illustrates a variation of a device 200 having multiple reinforcement rings 240. As noted above, the reinforcement rings provide additional radial strength to the capturing portion 226 as the device 200 moves within the body lumen and prevents distortion of the capturing portion 226. However, as noted above, the device will be fabricated to provide varying regions of axial strength to allow for either the spring effect or the staged inversion discussed above. In any case, the rings 240 do not need to extend around an entire circumference of a device, variations include any number of supports that extend between adjacent traversing wires.

Figure 3G:
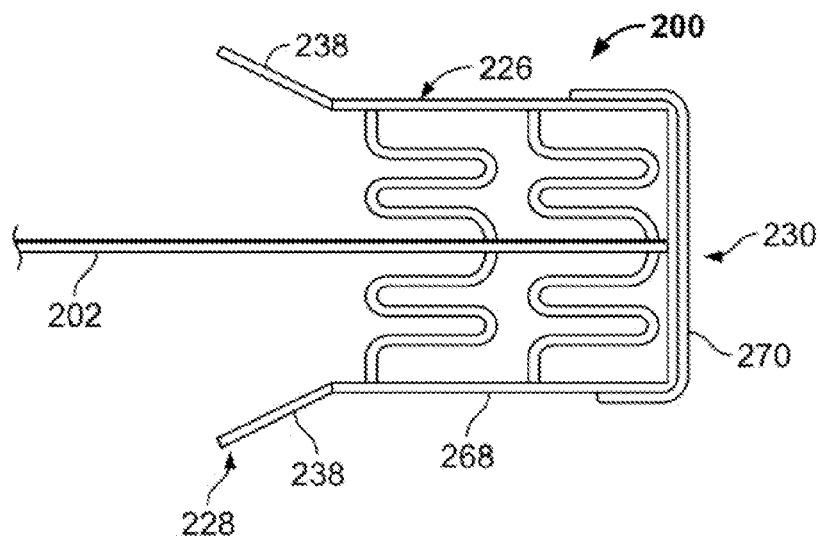

FIG. 3G illustrates another variation of a device 200 having a leading wire 202 extending to a distal end 230 of a capturing portion 226. In this variation the capturing portion 226 is fabricated from a stent-type structure. As noted above, it is within the scope of this disclosure to use any type of similar structure such as a laser cut tube, a chemically etched or photo etched tube, a polymer or metal injection molded structure, a basket, a filter, a bag, a coil, a helical wire structure, a mesh, a single wound wire, a film, a membrane, a polymer covering, or a plurality of crossing wires as the capturing portion 226 so long as the device can be compressed to a small size for delivery and expand after traversing the obstruction. The illustrated variation also shows a covering 270 located on the distal end 230 of the capturing portion 226. The length of the polymeric covering 270 can vary across the capturing portion 226 to prevent the obstruction from escaping as the device is translated over the obstruction. Furthermore, the covering 270 can be polymeric or a wire mesh. However, typically the covering has sufficient porosity to allow blood to flow through the device 200. In this variation, the flanges 238 form the translating surface.

Figure 3H:
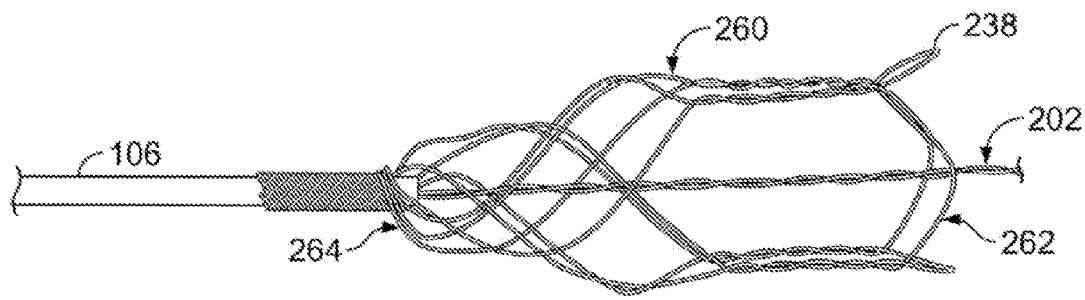

FIG. 3H illustrates another feature for use with system described herein. In this variation, the system includes a proximal capturing portion 260 located on an exterior of a delivery sheath 106. The main bundle 202 extends through the sheath 106 to a distal capturing portion (not shown). As discussed below, the proximal capturing portion 260 can be similar to the distal capturing portions 226 described herein with the exception that the distal end 262 of the proximal capturing portion is open while the proximal end 264 of the proximal capturing portion is closed. Furthermore, the proximal capturing portion 260 articulates with respect to the sheath 106 much in the same manner as the distal capturing portion 226 articulates relative to the main bundle 202. In this variation, the proximal end 264 of the proximal capturing portion 260 is tapered or has a smaller profile than the remaining proximal capturing portion 260. Such a feature may be useful to improve the deliverability of the device to the intended site as well as to maneuver around any obstructions within the body passage. In addition, as noted below, the proximal capturing portion 260 can be compressed about the obstruction to improve the ability of the system to remove the obstruction. The construction of the proximal capturing portion 260 can optionally include variations having regions of differing axial strength, or sections capable of generating spring force. Typically, since the proximal capturing portion 260 is not advanced distal to the obstruction, the need for staged inversion is not necessary. Accordingly, any number of capturing designs can be incorporated for the proximal capturing portion.

In some variations, the leading wire can extend to the proximal end of the system for manipulation by the physician. However, it is often the case that the characteristics of the device must vary along its length. For example, when the device is intended for use in remote tortuous anatomy, the proximal section of the device is desirably stiffer (to advance the distal portion of the device to the target anatomy). However, the distal section of the device must have properties that make it suitable for the tortuous anatomy. In the case where devices are used in the cerebral vasculature, the distal section must be extremely flexible, while the proximal section should be stiff. In many cases, different material properties are required. A problem then arises in attempting to join different materials especially in the joining region.

Conventional joining methods include soldering, welding, gluing, thermal junctions, etc. These joining methods produce an area having an increase in the stiffness of the device. For example, if two wires are to be laser welded together, then the section where they are joined has an overlap which yields greater stiffness than the rest of the wire. This increased area of stiffness is often balanced against the strength of the joined segment. If the joined region is too long, the strength will be sufficient but the increase in stiffness often prevents navigation through the tortuous anatomy. IF the joined region is too short, then the device can navigate through the anatomy but the bond is weaker and a risk of failure increases.

FIG. 4A illustrates another variation of an improvement for use with the devices described herein especially for use in tortuous anatomy such as the cerebral vasculature. In this example, the capturing portion 226 is show with a number of leading wires 204 extending proximally. To provide the desired characteristics, the leading wires 204 are joined in region 196 to wires 198 having a structure that is suitable for the proximal anatomy (e.g., the wires are larger in diameter or stiffer). To enable use of the device 200 in the cerebral anatomy without compromising bond strength characteristics or flexibility of the device 200, the leading wires extend a pre-determined region so that the bond region 196 is placed out of the tortuous anatomy. Since the cerebral vasculature is approximately 30 centimeters in length, the leading wires 204 can extend for a length 195 of at least a predetermined length so that it remains very flexible when navigating the cerebral vasculature or other tortuous anatomy. In one example the length was 20 centimeters (but can be 30 or more centimeters). By deliberately extending the leading wires 204 by length 194, the length of the bond region 196 can be chosen to accommodate the proximal anatomy (where a greater stiffness of the bond region 196 can be accommodated). The length of the bond region 196 can vary depending on the application (e.g., from 2 to 20 cm for a device intended for cerebral the cerebral vasculature). However, the bond can extend along the entire proximal section of leading wire.

FIG. 4B illustrates an addition aspect of for use with devices described herein where the main bundle 202 has a curved or bend portion 252. This pre-set shape assists in orienting the capturing portion 226 within the body passage since the bend will cause the device to bias against a wall of the body passage.

Figure 4C:
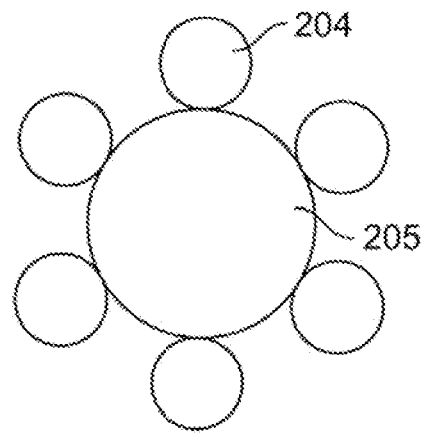
FIGS. 4C to 4E illustrate wires of different constructions within a main bundle.
Figure 4D:
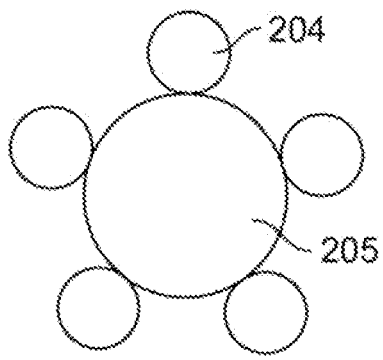

FIGS. 4C and 4D show cross sectional views taken along the line A-A in FIG. 4B. As shown, the wire form construction described herein allows for a number of configurations depending on the particular application. For example, the individual wires 204 (as discussed herein) may themselves comprise a bundle of smaller wires or filaments. In addition, the wires can be selected from materials such as stainless steel, titanium, platinum, gold, iridium, tantalum, Nitinol, alloys, and/or polymeric strands. In addition, the wires used in a device may comprise a heterogeneous structure by using combinations of wires of different materials to produce a device having the particular desired properties. For example, one or more wires in the device may comprise a shape memory or superelastic alloy to impart predetermined shapes or resiliency to the device. In some variations, the mechanical properties of select wires can be altered. In such a case, the select wires can be treated to alter properties including: brittleness, ductility, elasticity, hardness, malleability, plasticity, strength, and toughness.

The device may include a number of radiopaque wires, such as gold and platinum for improved visibility under fluoroscopic imaging. In other words, any combination of materials may be incorporated into the device. In addition to the materials, the size of the wires may vary as needed. For example, the diameters of the wires may be the same or may vary as needed.

In addition, the individual wires may have cross-sectional shapes ranging from circular, oval, d-shaped, rectangular shape, etc. FIG. 4C illustrates one possible variation in which a number of circular wires 204 are included with a d-shaped wire 205. Moreover, the device is not limited to having wires having the same cross-sectional shape or size. Instead, the device can have wires having different cross-sectional shapes. For example, as shown in FIG. 4D, one or more wires 205 can have a different cross-sectional shape or size than a reminder of the wires 204. Clearly, any number of variations is within the scope of this disclosure.

To illustrate one such example, a device can have 8-12 wires made of 0.003" round superelastic material (e.g., nitinol). The device may additionally have 2-4 wires made from 0.002" platinum for fluoroscopy. Of the 8-12 nitinol wires, 1-4 of these wires can be made of a larger diameter or different cross-section to increase the overall strength of the device. Finally, a couple of polymer fibers can be added where the fibers have a desired surface property for clot adherence, etc. Such a combination of wires provides a composite device with properties not conventionally possible in view of other formation means (such as laser cutting or etching the shape from a tube or joining materials with welds, etc.). Clearly, any number of permutations is possible given the principles of the invention.

In another example, the device may be fabricated from wires formed from a polymeric material or composite blend of polymeric materials. The polymeric composite can be selected such that it is very floppy until it is exposed to either the body fluids and or some other delivered activator that causes the polymer to further polymerize or stiffen for strength. Various coatings could protect the polymer from further polymerizing before the device is properly placed. The coatings could provide a specific duration for placement (e.g., 5 minutes) after which the covering degrades or is activated with an agent (that doesn't affect the surrounding tissues) allowing the device to increase in stiffness so that it doesn't stretch as the thrombus is pulled out. For example, shape memory polymers would allow the device to increase in stiffness.

Figure 4E:
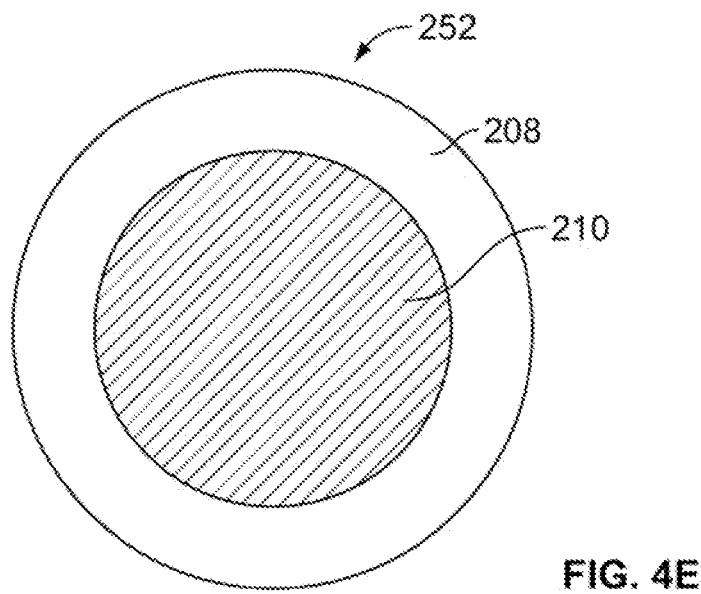

In another variation, one or more of the wires used in the device may comprise a Drawn Filled Tube (DFT) such as those provided by Fort Wayne Metals, Fort Wayne, Ind. As shown in FIG. 4E, such a DFT wire 252 comprises a first material or shell 208 over a second material 210 having properties different from the outer shell. While a variety of materials can be used, one variation under the present devices includes a DPI wire having a superelastic (e.g., Nitinol) outer tube with a radiopaque material within the super-elastic outer shell. For example, the radiopaque material can include any commercially used radiopaque material, including but not limited to platinum, iridium, gold, tantalum, or similar alloy. One benefit of making a capturing portion from the DFT wire noted above, is that rather than having one or more markers over the capturing portion, the entire capturing portion can be fabricated from a super-elastic material while, at the same time, the super-elastic capturing portion is made radiopaque given the core of radiopaque material within the super-elastic shell. Clearly, any composite DFT wire 252 can be incorporated into the system and capturing portions described herein.

Figure 5A:
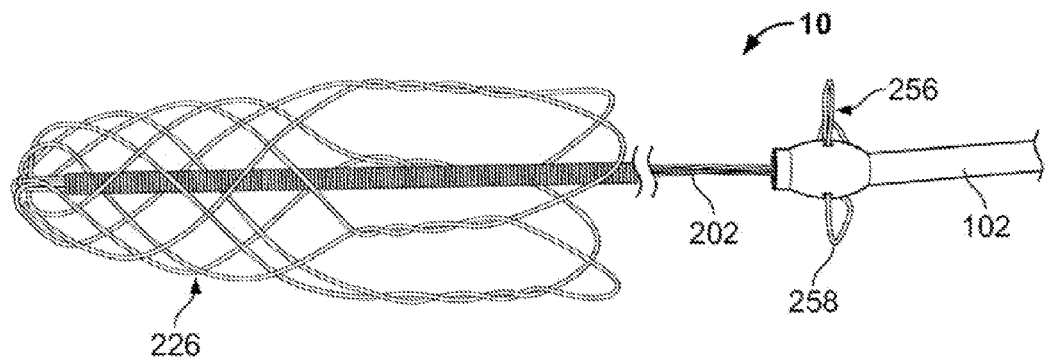
FIG. 5A illustrates am example of a proximal foot located on a catheter of the present system.

FIG. 5A shows a working end of a variation of a system 10 for removing an obstruction from a body lumen. In this variation, the system 10 includes a main bundle 202 and capturing portion 226 extending out of a micro-catheter or catheter 102. The micro-catheter 102 can optionally include a proximal foot 256 that can slide axially over main bundle 202 and can be variably positioned in relation to the capturing portion 226. The proximal foot 256 can include any number of configurations apart from the petal/flange 258 configuration (i.e., the foot can be a balloon, coil, shoulder, etc. where such structures simply replace the petals in FIG. 5A). In any case, the proximal foot 256 provides an increased surface area that provides an opposing force to the capturing portion 226, where the opposing force aids the movement of the obstruction within the capturing portion 226. Alternatively, the proximal foot stabilizes the obstruction and keeps the obstruction from moving with the capturing portion until the capturing portion envelops the obstruction.

The size of the proximal foot 256 can be adjusted depending on the target site anatomy. For example, a larger surface area can be employed if the target site is within a bifurcation of the body passage. The size of the proximal foot 256 can also be adjustable during the procedure. For example, in the case of a petal/flange 258 configuration, the petals 258 can assume a larger size to initially stabilize the obstruction and then reduce in size to allow the obstruction to be completely engulfed by capturing section 226.

The proximal foot 256 can extend from an interior of the catheter 102, such as from within the internal lumen of the catheter, or from an additional lumen within a wall of the catheter. Alternatively, the proximal foot 256 can be permanently affixed to the catheter 102. In such a case, a separate catheter (without a proximal foot) can be employed to traverse the obstruction for deployment of the device distally to the obstruction. Once the device is deployed, the catheters can be exchanged to provide the proximal loot. In an additional variation, the proximal foot 256 can be affixed to a delivery sheath (as described below) and be collapsed within the catheter, where advancement out of the catheter expands the proximal foot 256 so that it may function as described above.

In an additional variation, a proximal capturing portion (as shown in FIG. 3H) can be used with a foot 256 that is located about the main bundle 202. Such a variation may or may not include a distal capturing portion. Accordingly, the construction of the proximal capturing portion (as described herein to include sections of varying axial strength) can be used to perform a push and relax technique (similar to that of the pull and relax technique described herein).

Figure 5B:
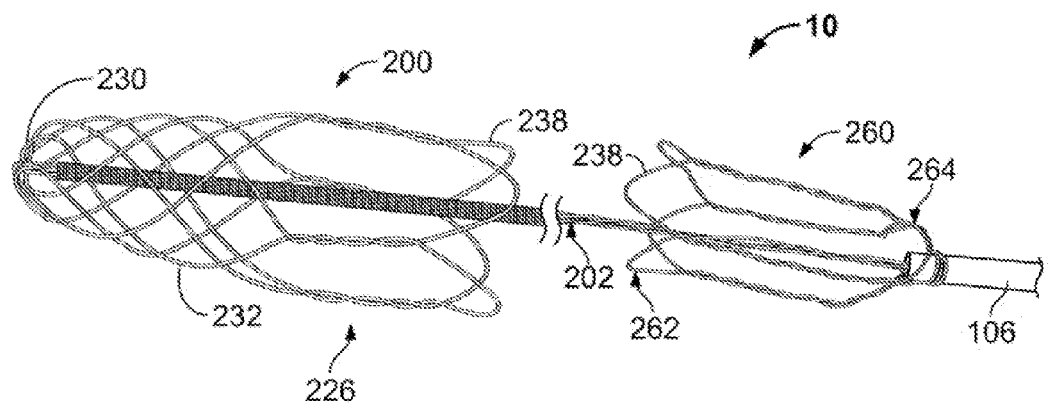
FIG. 5B illustrates a distal and a proximal capturing portion located on a system under the present invention.

FIG. 5B illustrates another variation of the system 10 where the system includes a proximal capturing portion 260 located on an exterior of a delivery sheath 106. Naturally, the proximal capturing portion 260 could also be affixed to an exterior of a micro-catheter. The proximal capturing portion 260 is similar to the capturing portions 226 described herein with the exception that the distal end 262 of the proximal capturing portion is open while the proximal end 264 of the proximal capturing portion is closed. The proximal capturing portion can also optionally be configured to have regions of varying axial strength, spring rate, and various other features associated with the distal capturing portion 226. In the illustrated variation, the capturing portion 226 and main bundle 202 move relative to the proximal capturing portion 260 to capture an obstruction. Furthermore, the proximal capturing portion 260 articulates with respect to the sheath 106 much in the same manner as the distal capturing portion 226 articulates relative to the main bundle 202. As shown, the petals 238 on the open ends 228 and 262 can interact to nest once the capturing portions 226 and 260 are moved sufficiently close to one another. The outward force caused by the retained obstruction provides a frictional interaction between adjacent petals/flanges 238 to maintain the nesting.

Variations of the device include additional structures, such as springs, hooks, barbs, etc, to cause the open ends 228 and 262 to interlock. As noted above, a separate catheter can be used to initially deploy the capturing portion 226 beyond the obstruction. Although the capturing portions shown have the same configuration, the capturing portions 226 and 260 used in any given system do not have to match in size, shape, and configuration. For example, the proximal capturing portion can be impermeable to flow while the distal capturing portion allows flow. In another example, one basket may be undersized relative to the other to improve nesting.

In any case, the construction of the system 10 shown in FIG. 5B includes open ends 228 and 262 of capturing portions 226 and 260 that are unconnected. Accordingly, as the capturing portions 226 and 260 move towards one another as a result of the main bundle 202 translating relative to the delivery sheath 106 the open ends are free to articulate around the main bundle 202 and delivery sheath 106 respectively to remain expanded against the lumen wall.

Figure 5C:
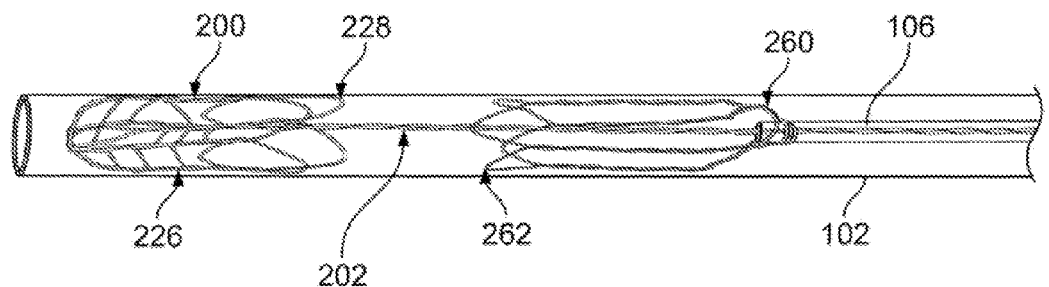
FIGS. 5C to 5E illustrate an overview of a variation of a delivery system employing a proximal and distal capturing portion.
Figure 5D:
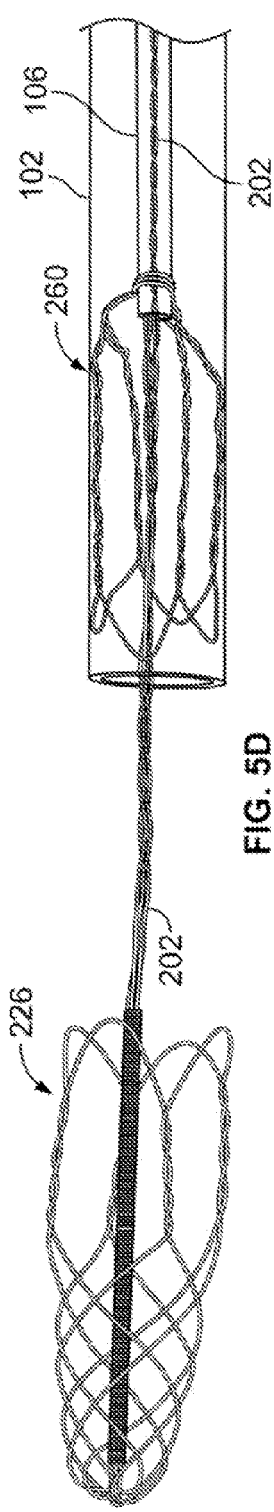
Figure 5E:
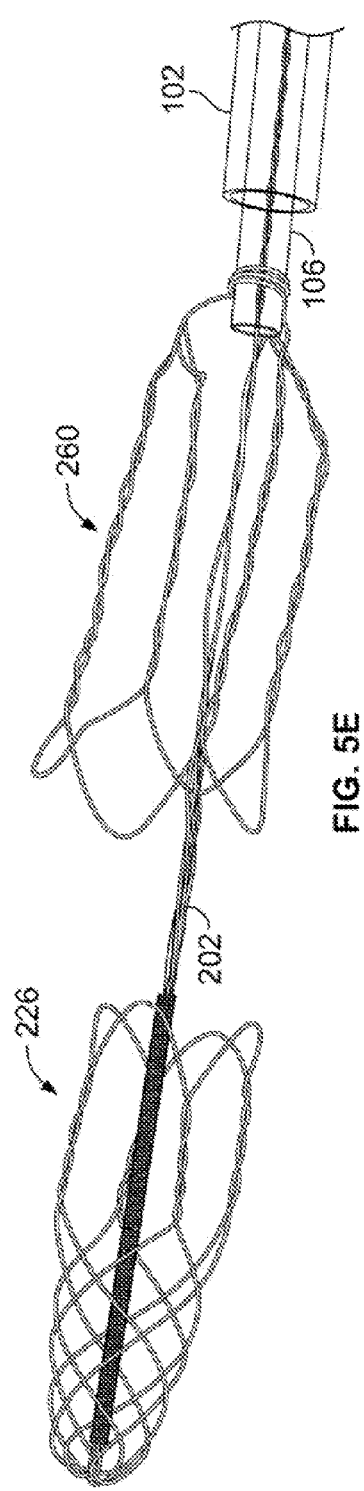

FIGS. 5C to 5E illustrate a variation of a system for delivery of the capturing portions 226 and 260. FIG. 5C shows the proximal 260 capturing portion affixed to a delivery sheath 106. In alternate variations, the proximal capturing portion 260 can be replaced with a proximal foot (not shown). As noted above, the main bundle or leading wires 202 extends through the delivery sheath 106 and connects to the distal capturing portion 226 beyond the opening 228 of the distal capturing portion 200. The main bundle or leading wire 202 extends through the proximal capturing portion 260. This allows the free ends of the capturing portions 228 and 262 to remain relatively unattached so that they can articulate and conform to the curvature of the vessels (as discussed below). The capturing portions 226 and 260, main bundle 202 and delivery sheath 106 extend through a microcatheter 102.

FIG. 5D illustrates a state of deployment after the microcatheter 102 traverses the obstruction (not shown). Once the microcatheter 102 is distal to the obstruction, the distal capturing portion 226 deploys from the end of the microcatheter 102. As noted herein, the capturing portions can self-expand or can expand upon actuation by the physician. In any case, the distal capturing portion 226 should be sufficiently collapsible to remain within the microcatheter 102 for deployment distal to an obstruction. To deploy the distal capturing portion 200 from the catheter 102, the main bundle 202 can translate to push the distal capturing portion 226 to eject it from the catheter 102. Alternatively, the microcatheter 102 can be withdrawn from the distal capturing portion 226.

FIG. 5E illustrates the deployment state after the catheter 102 is withdrawn proximal to the obstruction (not shown) and after the proximal capture portion 260 is delivered from the microcatheter 102. As noted above, the proximal capture portion 260 can be affixed to an exterior of the catheter, in which case the catheter may be either de-sheathed or exchanged. Alternatively, and as shown, the proximal capturing portion 260 is affixed to a delivery sheath 106 and is fabricated to collapse within the microcatheter for ultimate deployment, whereby translating the sheath 106 delivers the proximal portion 260 from the microcatheter.

Figure 5F:
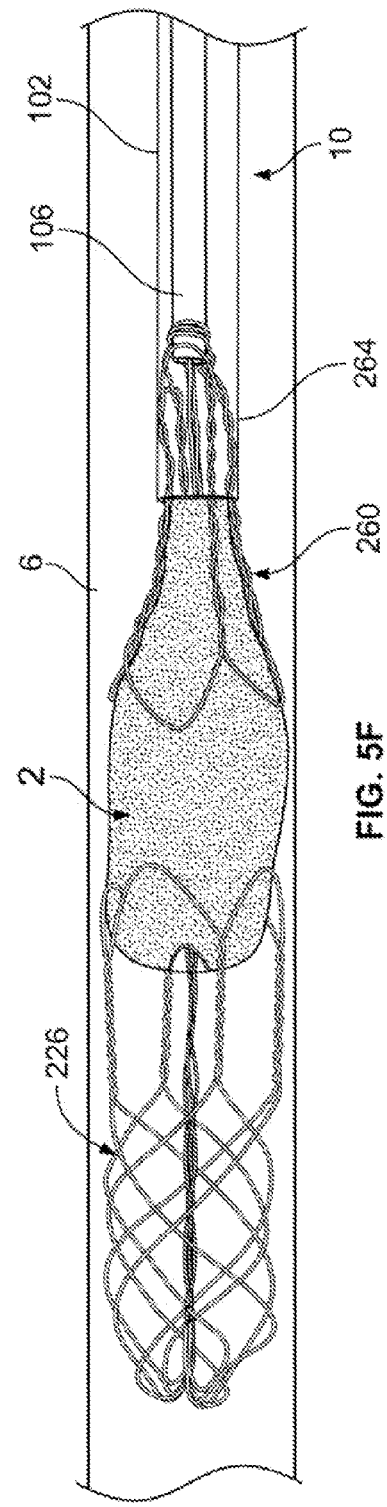
FIG. 5F illustrates compression or collapsing of a proximal capturing portion about an obstruction prior to translation of the obstruction in the vessel.

FIG. 5F shows another aspect of the system 10 where the proximal end 264 of the proximal capturing portion 260 is collapsed or compressed about an obstruction 2 prior to translation of the obstruction 2 within the vessel. In this illustration, the proximal capturing portion 260 is compressible by advancing the catheter 102 over the closed proximal end 264 of the capturing portion 260. In such a case, the proximal capturing portion 260 is slidable within and relative to the catheter 102. Naturally, variations may include compressing the proximal end 264 during translation of the obstruction 2. In either case, the proximal capturing portion 260 can be compressed in a number of different ways. For instance, the proximal basket can be compressed using a catheter 102 (as shown), or the delivery sheath 106, or any other number of mechanisms (not illustrated).

As shown, the proximal end 264 can be compressed using a sheath 106 and/or catheter 102 However, other means of compressing may be employed (e.g., a loop structure, a tube over the sheath, a draw-string configuration, etc.) In use, once the distal capturing portion 226 is deployed distally to the obstruction 2 and the catheter 102 is withdrawn proximal to the obstruction 2, the proximal capturing portion 260 is deployed. As the proximal capturing portion 260 partially (or totally) engulfs the obstruction 2, the physician can collapse or compress the proximal capturing portion 260 to better secure the obstruction within the system 10.

It is noted that any number of shapes, configurations, as well as any number of joined wires may be contemplated to form devices under the present disclosure. However, variations of the invention include selecting a number of wires to produce specific structural properties to the device. For example, the devices can have any number of wires where the limit is determined by the ability to produce a device of a sufficiently small size to access the area containing the obstruction. However, in some cases, it may be desired that wires are chosen to impart specified characteristics. For example, in the illustrated variation, the main bundle may comprise any number of wires that do not diverge to form subsequent shapes in the device. In other words, not all of the wires forming a section are required to diverge to form an adjacent section. Instead, these non-diverging wires may simply "loop" back away from the device. In an additional variation, one or more wires may diverge to form a particular portion of the capturing portion (e.g., the closed end, traversing wire, etc.). Then the wires can loop back to converge again with the main bundle.

FIGS. 6A to 6E show one example of the deployment of a variation of a device according to the present invention about an obstruction in a vessel. The figures are intended to demonstrate the initial placement of the device immediately prior to removal of the obstruction.

FIG. 6A illustrates an obstruction 2 lodged within a body lumen or vessel 6. In the case where the vessel is a cerebral artery, the obstruction may result in an ischemic stroke. Using standard interventional catheterization techniques, a microcatheter 102 and guidewire 104 traverse the obstruction. The microcatheter 102 may be advanced through the obstruction 2. Alternatively, the microcatheter 102 may "push" aside the obstruction and is advanced around the obstruction. In any case, the microcatheter 102 travels from the near end 3 (or proximal side) of the obstruction 2 to the far end 4 (or distal side) of the obstruction 2. It is noted that the catheter 102 may be centered or off-center with respect to the obstruction 2. Furthermore, the device may or may not be used with a guidewire to navigate to the site and traverse the obstruction.

Some variations of the device may be placed without an accompanying guidewire. Moreover, the structures discussed herein may be directly incorporated into a guidewire assembly where deployment may require a sheath or other covering to release the components from constraint.

FIG. 6B illustrates deployment of a capturing portion 226 and main bundle 202 of the device 200 from within the microcatheter 102 distal to the obstruction 2. Accordingly, in most variations, the capturing portion 226 is designed to fit within the catheter 102 for delivery and expand upon deployment. Alternatively, the device may be actuated to assume the desired shape (e.g., upon reaching a transition temperature where one or more wires comprise a shape memory alloy). As shown, the capturing portion 226 includes a traversing section 234 and a capturing section 232. In some procedures the traversing section 234 engulfs the obstruction 2 with little or no complication as the main bundle 202, catheter 102, or sheath 106 pulls the capturing portion 226 in a proximal direction.

Figure 7A:
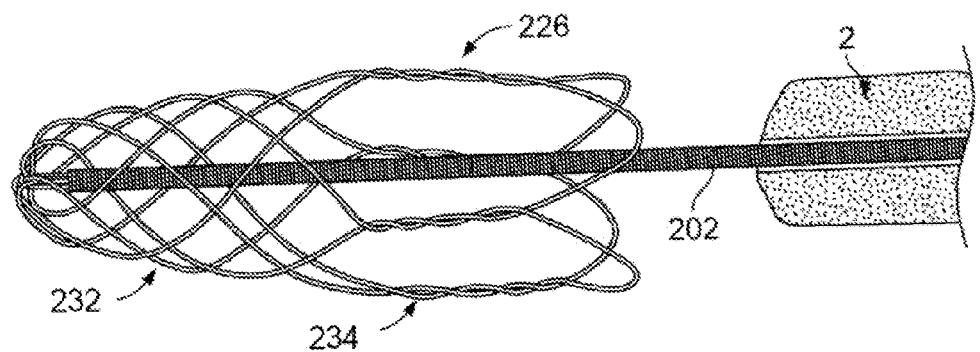
FIGS. 7A to 7C illustrates a condition where a section of the capturing portion deflects to provide a spring force that gradually drives a traversing section along the obstruction.
Figure 7B:
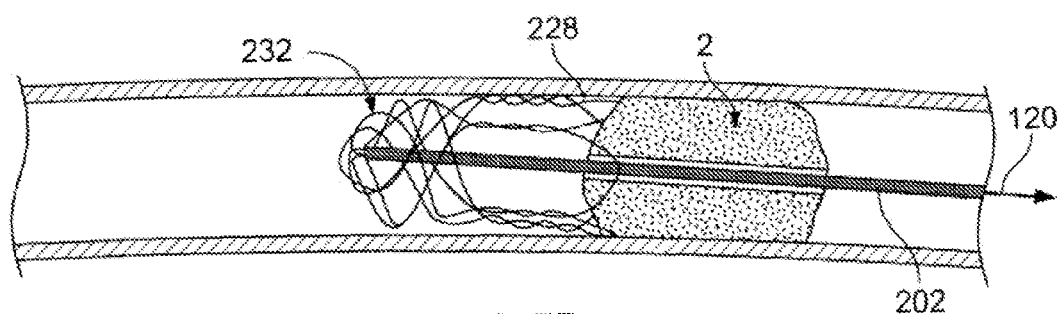
Figure 7C:
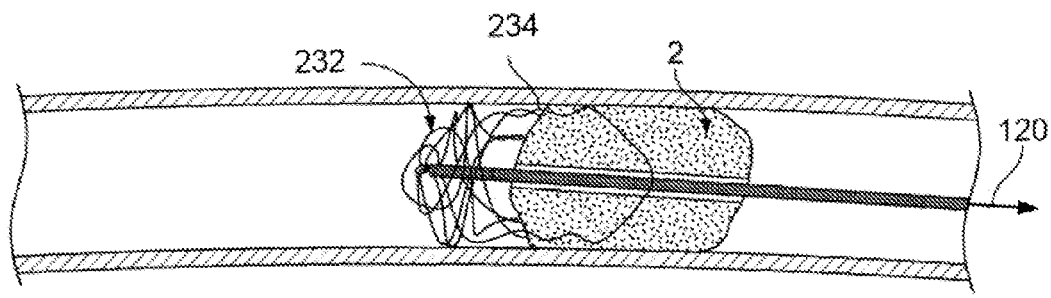

However, as discussed above, there may be some procedures where the distal capturing portion 226 is deployed distal to an obstruction 2 that is deposited within the vessel or lumen such that a steady translation of the capturing portion 226 will not engulf the obstruction 2. FIGS. 7A to 7G illustrate some examples of such a situation. As shown in FIG. 7A, a sheath 106 might be able to traverse the obstruction 2 to deploy the distal capturing portion 226 in preparation for engulfing the obstruction 2. FIG. 7B illustrates a condition where the traversing section 234 engages the obstruction 2 but is unable to easily or fully engulf the obstruction 2. However, in those variations where the capturing portion 226 includes regions having different axial strength (as discussed above), continued pulling of the main bundle 202 in a proximal direction 120 causes the capturing section 234 to compress. When the capturing section 234 is constructed to function as spring, the deformation of the capturing section 232 stores energy from the proximal movement of the main bundle 202. This storing of energy allows the physician to relax the pulling force 120 on the main bundle 202. FIG. 7C shows a compressed capturing section 234. The energy stored in the capturing section 232 gradually drives the open proximal end 228 of the translating section 234 over or along the obstruction 2. The physician can apply this "pull and relax" technique repeatedly until the obstruction is sufficiently captured by the capturing portion 226. In some variations, the capturing section 234 remains compressed as the obstruction 2 finally breaks loose and removed.

Figure 7D:
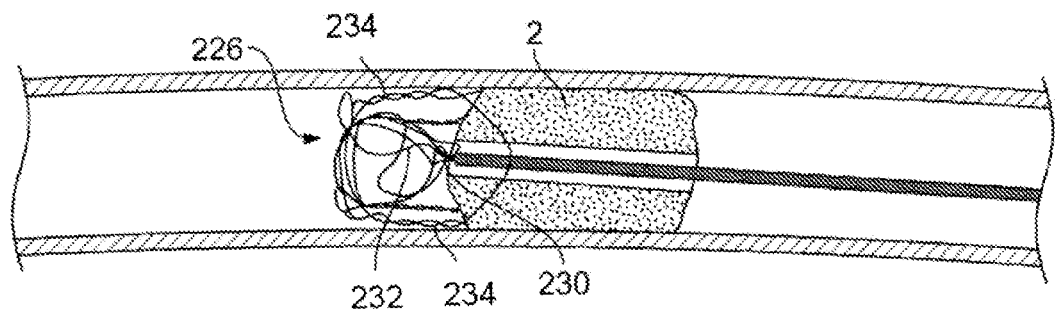
FIGS. 7D to 7G illustrate staged inversion of the distal capturing portion to allow removal of the device from an immovable clot.

FIG. 7D represents the situation where a distal capturing portion distal to an object 2 that is significantly embedded within a vessel or body lumen. In such cases, the force required to remove the obstruction 2 may damage the vessel or lumen. Such obstructions include atherosclerotic plaque or other immobile objects. As shown, when the distal capturing portion 226 is pulled once the proximal force 120 reaches a threshold value (as determined by the construction of the capturing portion 226) the capturing portion 226 undergoes a staged inversion as the permeable end 230 enters the traversing section 232. In this variation, the permeable end 230 actually enters the obstruction 2. The construction of the capturing portion 226 prevents flattening or expanding in diameter, where such movements would prevent removal of the capturing portion. Again, if the force applied by the capturing portion 226 breaks the obstruction 2 free. The obstruction 2 can be removed even though a part of the capturing portion 226 is within the obstruction 2 as shown in FIG. 2D.

Figure 7E:
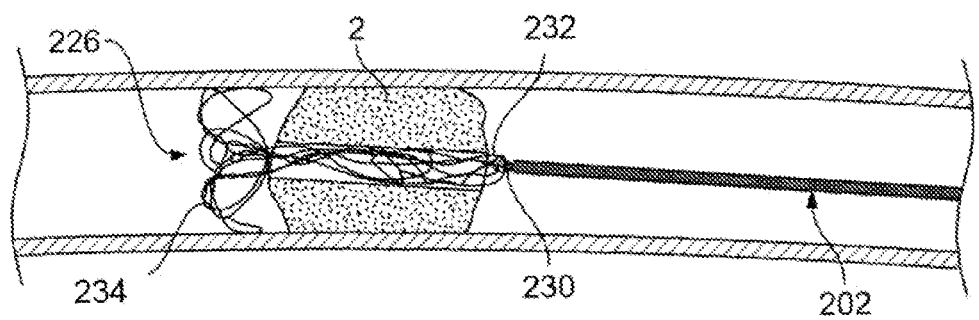

FIG. 7E shows advanced inversion of the capturing portion 226 as the capturing section 234 is now proximal to the traversing section 232. The traversing section 232 may be deformed upon inversion but will taper towards the capturing section 234 as the capturing section 234 passes through the obstruction 2 (typically via an opening that was previously created by advancement of a sheath 106 through or around the obstruction 2).

Figure 7F:
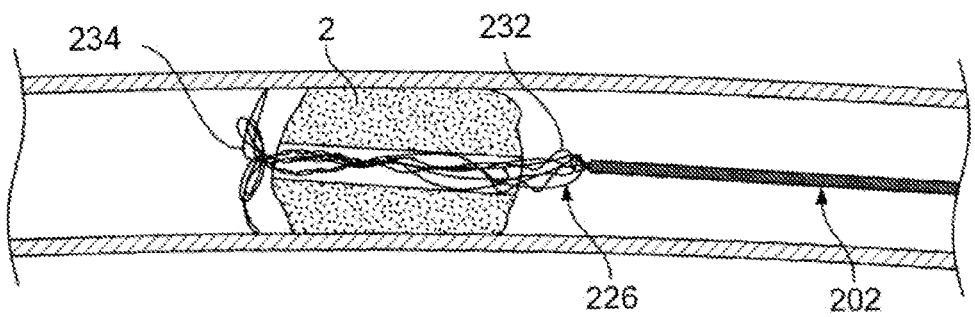
Figure 7G:
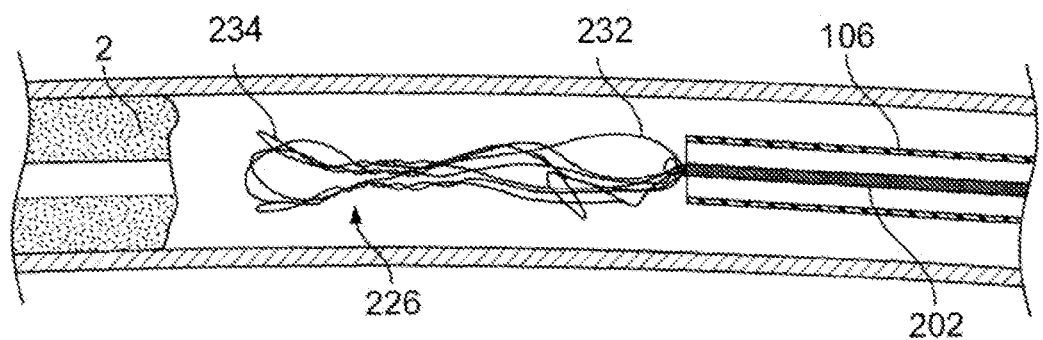

FIG. 7F shows the capturing portion 226 nearly passing through the obstruction 2 so that it may be removed from the body. As shown in FIG. 7G, the capturing portion 226 is now fully inverted and is in a state where it can re-enter a catheter for removal from the patient.

The construction described herein that allows for staged inversion of the capturing portion 2 provides a significant safety feature. A physician must undertake additional surgical intervention to remove any retrieval device that has become lodged distally to an immobile obstruction. The ability of staged inversion allows the physician to invert and remove the capturing portion 226 if application of a predetermined or threshold force is exceeded by proximal displacement of the device. This feature reduces the need for additional surgical intervention to remove a retrieval device that would otherwise become lodged or separated as a result of excessive forces being applied.

FIGS. 8A to 8B illustrate an additional benefit of affixing a leading wire or bundle of wires 202 beyond a proximal opening 228 of a capturing portion 226. FIG. 5A illustrates a basket type structure 90 where a wire 202 is affixed to a proximal end 92. As shown, as the leading wire 202 pulls the basket 90 through tortuous anatomy 6, the force component pulling away from an axis of the device 90 causes the proximal open end 92 to constrict or reduce in size. As shown, as the proximal end 92 approaches the obstruction 2 the perimeter of the end is not placed against the walls of the body passage 6. As a result, the constricted opening 92 places an increased axial force on the obstruction 2 as the basket 90 translates over the obstruction 2 (because the proximal end 92 pushes against the obstruction rather than sliding around it), making encapsulation of the obstruction more difficult and possible leading to vascular damage.

FIG. 8B shows a device 200 according to the principles disclosed herein. The leading wire 202 is affixed to the distal end 230 of the capturing portion 226. As the main bundle 202 is pulled through the curved vascular path, the capturing portion 226 pivots or articulates about the bundle 202 and remains aligned with the axis of the vessel. As a result any misalignment between the leading wire 202 and an axis of the capturing portion 226 does not affect the open proximal end 228. As noted above, some closing of the open proximal end may occur, though it will not be sufficient to interfere with the obstruction as the capturing portion moves over the obstruction. Such a configuration allows the perimeter of the open proximal end 228 to remain against the wall of the passage 6. As shown, because the open proximal end 228 is not constricted, the open proximal end 228 is better suited to slide around the obstruction for eventual removal.

FIG. 8C shows withdrawal of the microcatheter 102 to the proximal side 3 of the obstruction 2 and deployment of a proximal capturing portion 260 (in alternate variations, a proximal foot can be used or the capturing portion 226 alone can be used). Again, the catheter 102 can be exchanged for a catheter 102 having a proximal capturing portion 260. Alternatively, and as shown in the accompanying figures, the proximal capturing portion 260 can be affixed to a delivery sheath 106 that is fed through the microcatheter 102.

As also shown in the figure, the main bundle 202 and capturing portions become misaligned due to the tortuousity of the anatomy. However, because the capturing portions 226 and 260 are able to pivot or articulate relative to the main bundle 202 and catheter 102 or sheath 106, the open ends are able to remain against the lumen wall. In conventional devices where the open end is attached to either a wire or catheter, when the wire or catheter bends in the anatomy, the forces exerted on the open ends deform or distort the end to assume a reduced profile. Accordingly, the physician may have difficulty in removing an obstruction if the profile of the open end becomes reduced in size. Closing of the open end can also result in vascular damage if the physician applies too much force in translating the device.

Figure 8E:
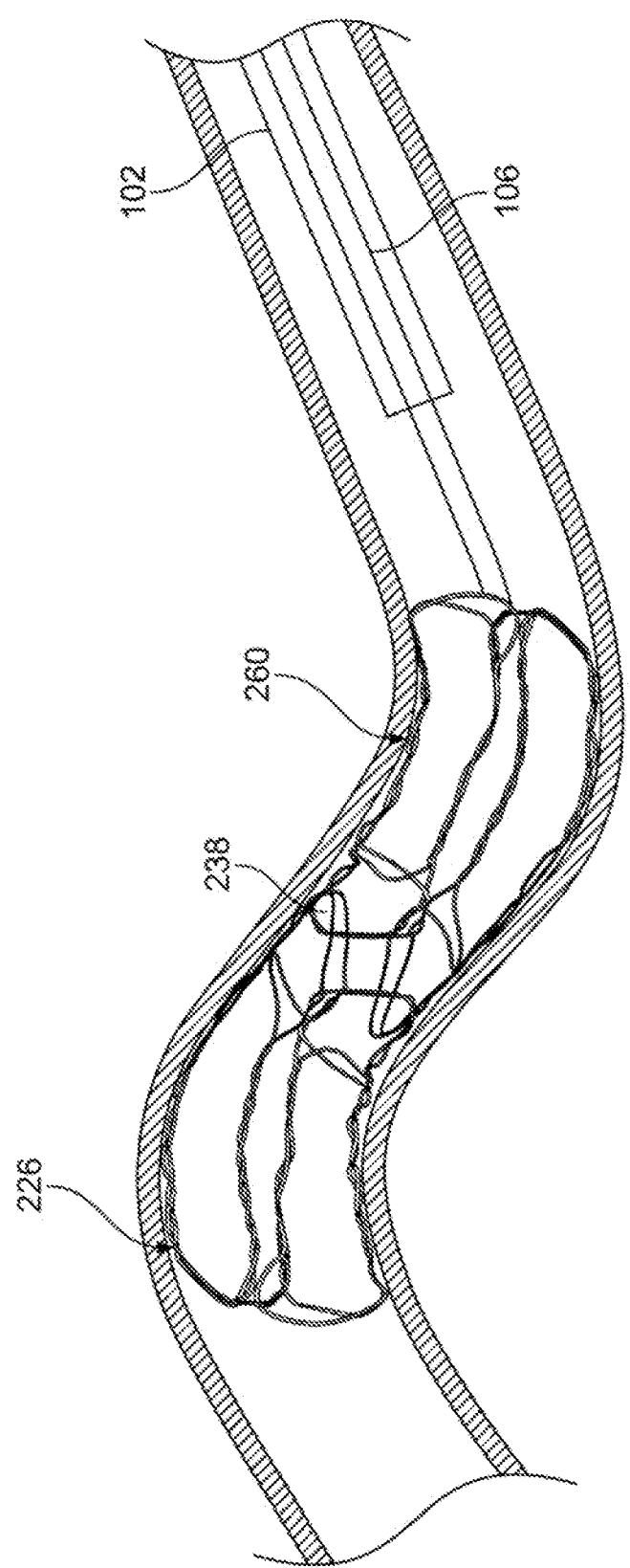
FIGS. 8C to 8E illustrate a proximal capturing portion and a distal capturing portion approaching an obstruction.

FIG. 8D shows movement of the capturing portions 226 and 260 adjacent to the obstruction 2. The proximal capturing portion 260 can remain stationary or may be advanced relative to the distal capturing portion 226. Regardless, the physician is able to ensnare the obstruction 2 within the cavities defined by the capturing portions 226 and 260. FIG. 8E illustrates the system as the two capturing portions are drawn together. For purposes of clarity, the obstruction is not shown. Upon sufficient advancement of the capturing portion 226 and proximal capturing portion 260 relative to one-another, flanges 238 on the respective open ends can interlock. This feature provides added safety in removing the device as the obstruction is encapsulated between the two nested portions.

Figure 8F:
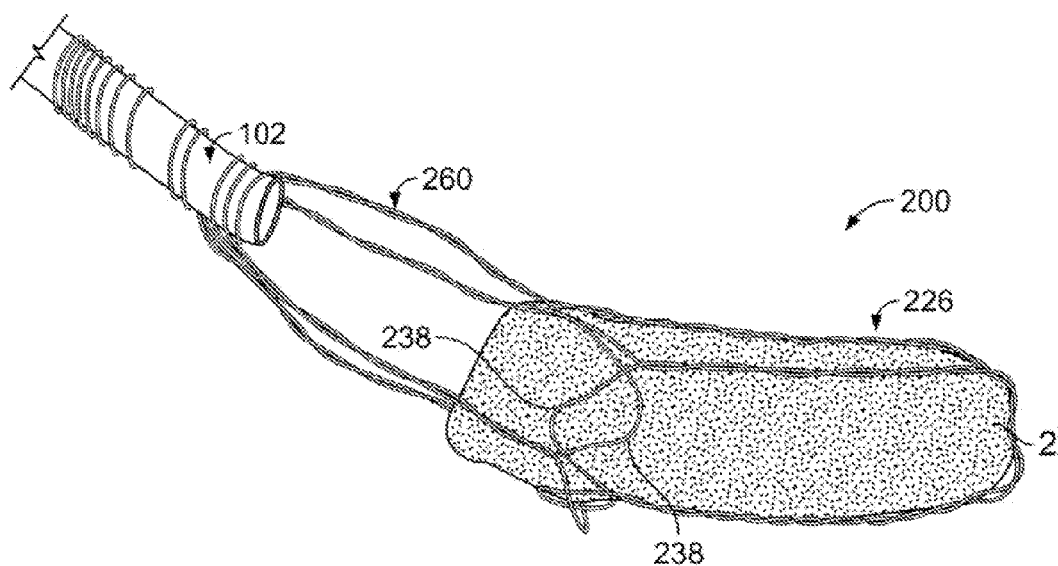
FIG. 8A illustrates closure of the proximal opening of a capturing portion without the benefit of articulation of the capturing portion about a leading wire.
FIG. 8B illustrates, conceptually, one benefit of articulation of a capturing portion about a leading wire or main bundle of wires.

FIG. 8F illustrates a device 200 after securing an obstruction between a proximal 260 and distal 226 capturing sections. As shown, the captured obstruction 2 is held between capturing portions 226 and 260 where the flanges 238 nest within one-another to "lock" the capturing portions together. In some variations of the device, one of the capturing portions can be undersized relative to the other. This configuration allows for the undersized capturing portion to become further compressed as the devices are pulled together. The compression of the capturing surface then serves to further compress the obstruction 2 captured within the device.

The capturing portions described herein can include coverings or wrappings so long as the other features of the device are not impaired. Such coverings can be located on both capturing portions 226 and 260, only one or more capturing portions. The covering can include a strand or fiber wrapped or woven about the section, a polymer film, or a dipped polymer coating such as silicone, urethane, etc. The coating on either capturing portion can be solid or porous. In the latter case, blood can continue to flow through the coating. In one variation, the proximal capturing portion 260 could employ a solid covering while the distal capturing portion 200 could include a porous covering. In such a case, blood or other fluid flow could be temporarily halted by the presence of the solid covering to assist in removal of the obstruction.

FIG. 9 illustrates a variation of the system where the main bundle 202 includes a medial foot 274. The construction of the medial foot 274 can be similar to that of the proximal foot discussed above (e.g., wires looped into a petal configuration.) However, the medial foot includes a surface area or diameter larger than a diameter of the main bundle. In any case, the increased surface area of the medial foot 274 provides an increased resistance to the obstruction 2 as the distal capturing portion 200 and main bundle 202 are pulled in a proximal direction towards an obstruction 2. The medial foot 274 engages the obstruction 2 to partially displace or loosen the obstruction from the walls of the body passage. The medial foot 274 can be slidably located on the main bundle such that after a threshold force, the medial foot moves within the distal capturing portion 200. The main bundle 202 can include any number of medial feet 274.

Although the illustrated variation shown above comprise open-ended, circular, looped or partial loop shape cross sectional areas, variations of the capturing portions can include any number of shapes. For example, such a shape can include a circle, an arcuate shape, a partial circular shape, a loop, an oval, a square, a rectangle, a polygon, an overlapping loop, a pair of semi-circles, etc.) The various shapes may be heat set to be either self-expanding (i.e., superelastic) or the use of shape memory alloys can allow for the device to assume the particular shape upon reaching a desired transition temperature.

The exemplary shapes discussed above permit the shaped section to adjust in diameter in response to placement in varying diameters of body lumens. It is noted that a device may have different shaped sections on different ends of the device.

While many different shapes are contemplated to be within the scope of this disclosure, the shapes will depend upon the ultimate application of the device. As noted herein, the illustrated examples have particular applicability in retrieving obstructions from the vasculature. Accordingly, for these applications the shaped sections should form a shape so that they can expand against a vessel wall without causing trauma to the vessel. For example, upon release from the catheter, the shaped section can assume their resting shape and expand within the vessel. The resting shape can be constructed to have a size slightly greater than that of the vessel. Sizing the device relative to the target vessel may assist in placing the parts of the device against a vessel.

In an additional aspect, the shaped sections may be designed to have an unconstrained shape that is larger than the intended target vessel or simply different than a cross sectional profile of the intended vessel (i.e., not circular or tubular, but e.g., linear or other different shape). In such an example, as the shaped section is released from the delivery catheter, the shape section attempts to return to the unconstrained shape. In those variations where the unconstrained shape is different from the circular profile of the vessel, the leading wire assumes a shape that accommodates the vessel but is more rigid and stable since its unconstrained shape is entirely different from that of the vessel. In other words, the shaped section continually exerts an outward force on the vessel.

In yet another aspect, the shaped sections shown herein may not necessarily lie in the same plane. Instead, they can be axially spaced by an offset. One benefit of constructing the device to have non-planar shaped section is that the configuration might allow for delivery of the device through a smaller microcatheter because the shaped sections do not interfere with one another when collapsed to fit within the microcatheter.

Another aspect applicable to all variations of the devices is to configure the devices (whether the traversing filament or the surrounding portion) for better adherence to the obstruction. One such mode includes the use of coatings that bond to certain clots (or other materials causing the obstruction.) For example, the wires may be coated with a hydrogel or adhesive that bonds to a thrombus. Accordingly, as the device secures about a clot, the combination of the additive and the mechanical structure of the device may improve the effectiveness of the device in removing the obstruction. Coatings may also be combined with the capturing portions or catheter to improve the ability of the device to encapsulate and remove the obstruction (e.g., a hydrophilic coating).

Such improvements may also be mechanical or structural. Any portion of the capturing portion can have hooks, fibers, or barbs that grip into the obstruction as the device surrounds the obstruction. The hooks, fibers, or barbs 154 can be incorporated into any portion of the device. However, it will be important that such features do not hinder the ability of the practitioner to remove the device from the body.

In addition to additives, the device can be coupled to an RF or other power source (such as 14 or 16 in FIG. 1A), to allow current, ultrasound or RF energy to transmit through the device and induce clotting or cause additional coagulation of a clot or other the obstruction.

The methods described herein may also include treating the obstruction prior to attempting to remove the obstruction. Such a treatment can include applying a chemical or pharmaceutical agent with the goal of making the occlusion shrink or to make it more rigid for easier removal. Such agents include, but are not limited to chemotherapy drugs, or solutions, a mild formalin, or aldehyde solution.

As for other details of the present invention, materials and manufacturing techniques may be employed as within the level of those with skill in the relevant art. The same may hold true with respect to method-based aspects of the invention in terms of additional acts that are commonly or logically employed. In addition, though the invention has been described in reference to several examples, optionally incorporating various features, the invention is not to be limited to that which is described or indicated as contemplated with respect to each variation of the invention.

FIG. 10 illustrates one variation of a retrieval device 200 including a distal capture portion 226 coupled to one or more leading wires in the form of a main bundle 202. The main bundle extends through a sheath 106 that includes a proximal capture portion 260. The configuration of the retrieval device 200 can incorporate the proximal and distal capture portions discussed herein as well as various other configurations discussed in the commonly assigned patent applications noted above. In addition, the relative sizes of the various components shown in FIG. 10 and discussed below are for illustrative purposes only.

An end 264 of the proximal capture portion 260 is affixed to a distal end of the sheath 106. However, as noted above, other variations are within the scope of the disclosure. The main bundle 202 can optionally terminate at a handle 242. As noted above, in certain variations, the main bundle is joined to a stiffer wire or stiffer bundle of wires. This allows the device 200 to have a very flexible distal section with a relatively stiffer proximal section. FIG. 4A above, discusses placement of a joint at a location spaced from the distal section of the device so as to increase a bond strength but not impair the distal section's flexibility. In any case, the device 200 can have a proximal bundle 203 that comprises either the exposed wires or a covering/tube over the wires. In certain variations, the bundle or wire 202, 203 can be encapsulated with a coating.

The proximal end of the sheath 106 includes a sheath handle 244. As discussed herein, axial movement of the bundle 202 or proximal bundle 203 (typically at the handle 242) results in movement 126, or translation of the bundle within the sheath 106. This action moves the distal capture portion 226 (as shown by arrows 126). In certain variations, the device 200 is loaded into a microcatheter (not shown but discussed above) that is delivered to the site of the obstruction and crosses the obstruction.

In some variations, the sheath hub 244 includes one or more locking hubs 246. Where actuation (either axial or rotational) of the locking hub 246 locks the main bundle 202 relative to the sheath handle 244 and sheath 106. It follows that such locking action also locks the distal capture portion 226 relative to the proximal capture portion 260. A variety of methods can be employed to increase a frictional interference between the locking hub 246 and the proximal bundle 203. As a result, when a physician determines a length of an obstruction, the physician can set a spacing between the capturing portions 226 260 by locking the proximal bundle 203 relative to the sheath hub 244. Accordingly, the proximal bundle 203 can include any type of incremental markings to allow the physician to readily determine a spacing of the capturing portions. As illustrated, the sheath hub 244 can include additional injection ports to deliver fluid or other substances through the sheath 106.

As noted above, the device 200 can be used with microcatheter. In those variations it is important that the device 200 is loaded without damaging the distal bundle 202, capture portions 226 260, and/or sheath 106. As a result, the device 200 can include an optional funnel 286 that reduces the proximal capture portion 260 (and/or the distal capture portion 226) for loading within the microcatheter and/or sheath 106.

Another variation of the device 200 includes an insertion tool 280 slidably affixed to the sheath 280. Because variations of the device 200 can be extremely flexible, the insertion tool 280 can be used to provide column strength to the sheath 106, bundle 202 or other components as the device 200 is pushed into the microcatheter. The insertion tool comprises a rigid section 282 and a frictional coupler 284. The rigid section 282 has a column strength that supports the device 200 to prevent buckling. The frictional coupler 284 can be a flexible material that allows an operator to squeeze or grip the coupler 284 to create a temporary frictional interface between the loading tool 280 and the device 200 (typically the sheath 106). Such an action allows axial advancement of the device 200 as the loading tool 280 is advanced into the microcatheter. Once the rigid section 282 is fully inserted into the microcatheter, the operator releases the frictional coupler 284 and can withdraw the loading tool 280 from the catheter without withdrawing the device 200. The insertion tool 280 can also include an optional loading tube 286 slidably coupled to the rigid section 282. When used, the funnel 286 can withdraw the proximal and distal capturing portion 226 260 within the loading tube 286. The loading tube 286 then couples to a microcatheter allowing the capturing portions to advance therein as the rigid section 282 and frictional coupler 284 advance the device 200 relative to the loading tube 286.

FIG. 11A illustrates a funnel catheter 300 useful for retrieving objects from vessels or body lumens. Typically, when a physician captures an obstruction in various retrieval devices, the device and the obstruction are easily removed from the body by withdrawing the device and obstruction into a sheath, guide catheter or introducer ("guide catheter"). However, in some circumstances, a physician has difficulty withdrawing the obstruction loaded device within a sheath, guide catheter or introducer. Specifically, one or more components of the retrieval device might become caught on an edge of the guide catheter. The concern may still remain even when using a guide catheter having an increased diameter (such as when the retrieval device catches on one edge of the guide catheter tip). Moreover, large guide catheters are difficult to advance within various parts of the anatomy. As a result, the obstruction loaded device must travel further. Movement of the obstruction loaded device within the body creates the risk that the obstruction will detach or break apart and cause additional adverse consequences.

The funnel catheter 300 includes a first and second slotted funnels 330, 340 located at the distal end of an inner shaft 302. Each funnel 330 340 comprises a number of extensions or tines 332 342. The inner shaft 302 can be cut to produce the first tines 332. Alternatively, the first tines 332 can be affixed to a portion of the inner shaft 302. The second slotted funnel 340 is offset in both a proximal and rotational position relative to the first slotted funnel 330. The purpose of this dual offset is discussed in detail below. As shown, the second funnel 340 can be a slotted tube that is affixed over the inner shaft 302. In an alternate variation, a plurality of second tines 342 can be located about the inner shaft 302 to form a second slotted funnel 340. As shown in FIG. 11B, the tines 332 342 can be configured to expand outward (if not restrained) via use of a coil or other spring-type means. Alternatively, they can be actuated to expand outward. However, in most cases, the tines 332 342 can expand passively upon entry of the retrieval device 200. The expansion of one or both funnels assists in receiving the retrieval device. In additional configurations, one or more funnels can be designed so that they remain in a cylindrical shape rather than expand outwards (as shown in FIG. 11C). Variations of the funnel catheter 300 can include configurations having one or more funnels, or configurations where the tines spaced or adjacent (or a combination thereof).

FIG. 11C also illustrates the dual offset nature of the dual funnel catheter 300. The first offset is a linear offset 316 such that the distal ends of the first tines 332 or funnel 330 extends beyond a distal end of the second tines 342 or second funnel 340. The second offset comprises a rotational offset (denoted by rotational angle A). For example, the illustrated rotational offset A is 45 degrees. However, the rotational offset can vary depending on the particular application. In most variations, the rotational offset A will place the second tines 342 over the gaps or spaces between the first tines 332. The number of tines can vary depending on the application. Variations of the funnel catheter can include discontinuous funnels with two or more tines.

Turning back to FIG. 11A, the funnel catheter 300 can optionally include any number of medical fittings or components. As shown, the catheter 300 includes a hemostasis valve or hub 306 at the proximal end. The hemostasis valve 306 can include a fluid side port 308 for delivery of fluid through the catheter 300. The catheter 300 can also include one or more radiopaque markers 310 so that the location of the funnel or funnels 330 340 can be identified via non-invasive imaging (e.g., under fluoroscopy). The funnel catheter 300 can also optionally include one or more markers 312. Such markers are useful to inform a physician (who is only able to view the proximal end of the device 300) of the distance to the first or second funnel. As a result, the physician will be able to determine whether the funnels are advanced out of the guide catheter. FIG. 11A also shows the funnel catheter 300 as including a loading tool 314. The loading tool 314 can be advanced over the funnels 330 340 to compress the funnel when loading into a guide catheter or other sheath.

FIGS. 12A to 12C provide an illustrative example where use of a funnel catheter 300 aids in removal of an obstruction 2 loaded within a retrieval device 200.

As shown in FIG. 12A, attempting to remove the obstruction 2 when engulfed in the retrieval device 200 creates a risk that one or more portions of the device 200 become caught on the guide sheath or access catheter 108. In some cases, the physician can simply engage the device 200 against the distal end of the guide sheath 108 and withdraw until the obstruction 6 and device 200 are located in an acceptable area of the body or withdrawn entirely from the body. For example, in certain situations, the obstruction 6 and device 200 can be withdrawn with the guide sheath 108 until all components reach a high flow, non-critical locations (e.g., the groin area). In the case of a clot, a clot dissolving substance (t-PA urokinase, etc.) can then be applied to dissolve and remove the clot. Alternatively, the physician can attempt to aspirate through the guide sheath 108 in an attempt to draw the entire retrieval device 200 and obstruction 2 within the guide sheath 108. In yet another variation, the physician can advance fibers or guide wires out through the guide sheath 108, then withdraw the obstruction 2/retrieval device 200 and attempt to use the fibers or guide wires as a moveable surface to capture the device 200. Furthermore, the physician can attempt to use a variety of existing devices (e.g., the FastCath provided by Genesis Medical Inc., the Merci Retriever provided by Concentric Medical Inc., or any commercially available snare or distal protection device) to remove the engulfed obstruction 2 from the body.

In some variations, the capturing portions discussed above can be constructed to improve their ability to be withdrawn into a guide sheath. For example, increasing the number of petals or flanges on the traversing sections increases the probability that the distal flanges nest within the proximal capturing portion. Alternatively, or in combination, the petals 238 on the distal capturing portion can be staggered in length or position to ease insertion into the proximal capturing portion. In another variation, the petals 238 shape or curvature can be adjusted so that they do not flare outward.

FIG. 12B shows a distal end of a funnel catheter 300 as it receives an obstruction 2 loaded retrieval device 200. As shown, the tines 332 of the first funnel 330 receive the device 200. The tines 332 minimize the likelihood that the device 200 becomes caught. The limited surface area of the tine 332 (combined with the rounded tines 332 342) produces a tendency for the device 200 to deflect away from the tines as it is withdrawn into the funnels. The second funnel 340 (being rotationally offset from the first funnel 330 provides coverage over the spaces between the first tines 332 thereby assisting in re-nesting of the device 200 within the funnels. Ultimately, the device 200 and obstruction 2 are withdrawn into a guide sheath 108 and removed from the body.

FIGS. 12 C to 12D show additional variations of funnel catheter 300. FIG. 12C shows a single funnel 330 having a plurality of tines 332. FIG. 12D illustrates a dual funnel catheter 300 having a discontinuous first funnel 230 and a second funnel 346. The second funnel 346 can be a continuous funnel so long as it is able to retract within the guide sheath 108. As shown, the second funnel 346 can include a single slit 348 that allows the funnel to compress within the guide sheath 108. In addition, the variation of FIG. 12D can be used without the first discontinuous funnel 330. Accordingly, as the retrieval device 200 and clot 2 approach the funnel 346 and enters the funnel, further withdrawing the retrieval device 200 causes squeezing of the retrieval device 200 and obstruction 2. In yet another variation, the funnel 346 can incorporate a drawstring to compress the funnel 346 once the retrieval device 200 and obstruction are located therein.

Figure 13A:
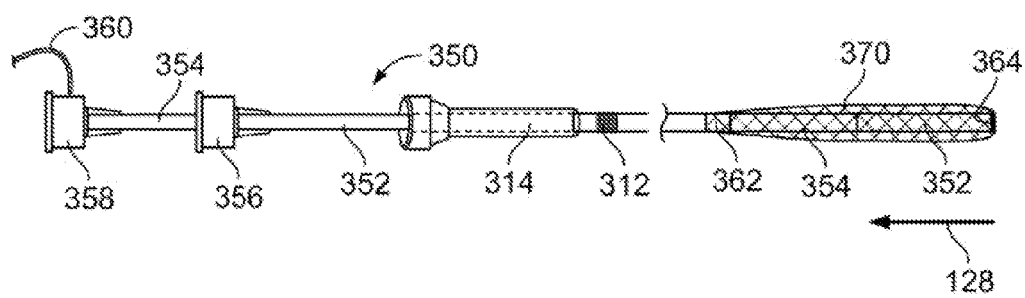
Figure 13B:
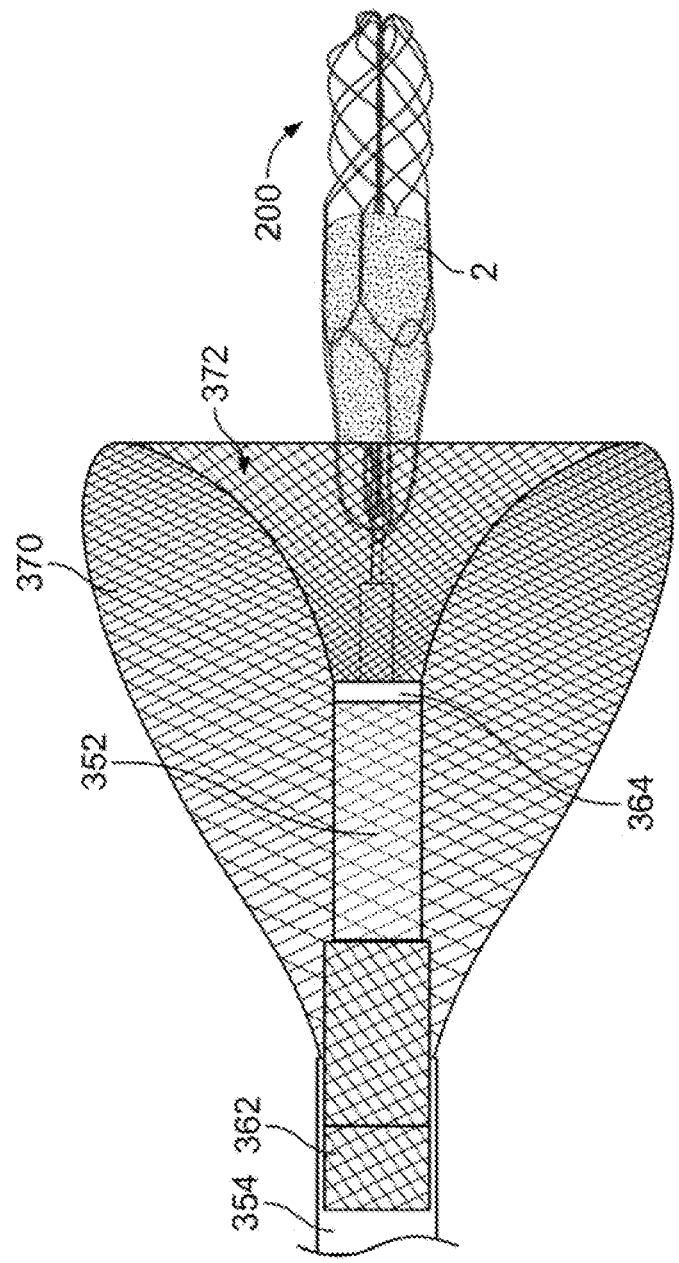

FIG. 13A to 13B illustrates another variation of a funnel catheter 350 suited to remove a retrieval device 200 from the body. As shown in FIG. 13A, the funnel catheter 350 includes a first shall 352 and a second shaft 354 slidably located therein. A mesh 370 is fused to each shaft 352 354 at a distal location 362 364. Accordingly, relative movement of the shafts 352 354 (either the first shaft 352 can be pushed or the second shall 354 can be pulled) creates a funnel shape 372 as the mesh portion affixed to the second shaft 354 is inverted within the remainder of the mesh 370. It is noted that in some variations of the system, the mesh funnel funnels are combined with the tine based funnels described above. Such that one funnel comprises the tines while the other comprises the mesh structure described herein.

In another variation, a third distally located capture portion (similar to a distal capture portion) can be used to draw the retrieval device within a guide sheath. In such a variation, the third capture portion can be a larger distal capture portion and when the retrieval device engulfs an obstruction, the third basket portion can be proximally withdrawn to capture the retrieval device and obstruction.

As illustrated in FIG. 13B, as the retrieval device 200 and obstruction 2 approach the funnel catheter 350, the distal attachment points 362 364 of the shafts 352 354 are moved together to invert the mesh 370 and form a funnel 372. The retrieval device 200 can then be withdrawn into the funnel. This design allows for the retrieval device 200 to be fully withdrawn into the catheter 350 while the funnel 372 is expanded. Alternatively, the funnel 372 can be used to compress the retrieval device 200 and obstruction 2 prior to withdrawal into the catheter 350.

The mesh 370 can include any medically acceptable material such as a nitenol braid. Furthermore, the mesh allows for flow through the vessel or lumen while expanded. However, additional variations of the device can include a solid layer of material substituted for the mesh.

Figure 13C:
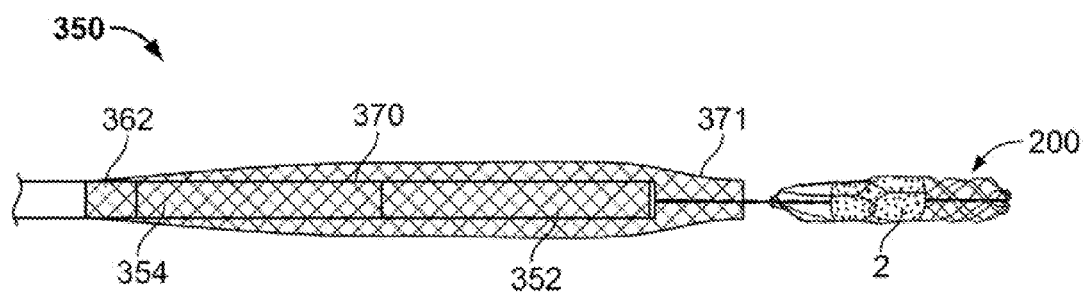
Figure 13D:
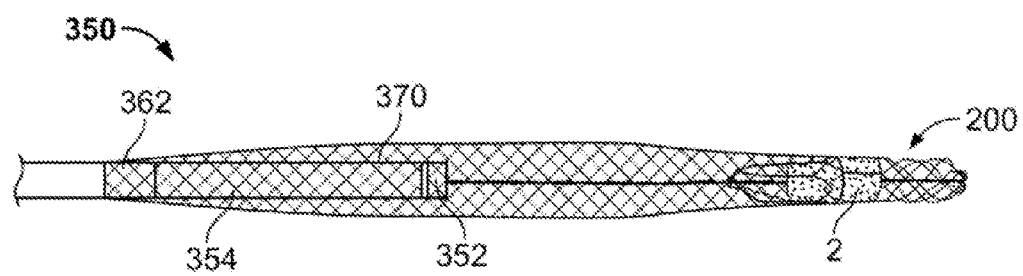
Figure 13E:
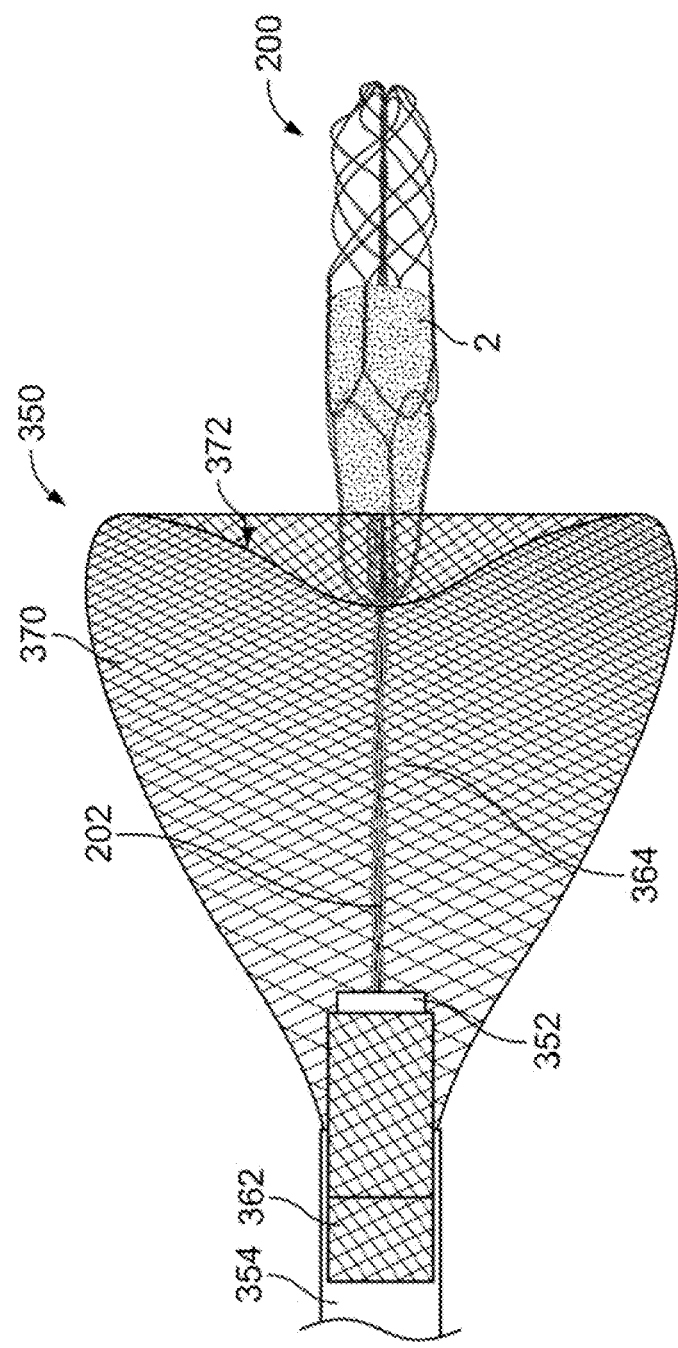

FIGS. 13C to 13E illustrate another variation of a funnel catheter 350 suited to remove a retrieval device 200 from the body. As shown in FIG. 13C, the funnel catheter 350 includes a first shaft 352 and a second shaft 354 slidably located therein. A mesh 370 is joined only the rear shaft 354 at a distal location 362. The end of the mesh 370 is free at the distal end of the device 350. The mesh 370 is sized at a distal end 371 to neck down. Accordingly, as the distal shaft moves rearward, the mesh 370 is unsupported. The necked section 371 of the mesh allows for distal advancement of the device 200 through the neck portion 371. However, as shown by FIG. 13D, rearward movement of the device 200 causes engagement with the neck portion 371. Further rearward movement of the device 200 causes the unsupported mesh 370 to form a funnel shape 372 as shown in FIG. 13E. The funnel shape allows for the retrieval device 200 to be fully withdrawn into the catheter 350 while the funnel 372 is expanded. Alternatively, the funnel 372 can be used to compress the retrieval device 200 and obstruction 2 prior to withdrawal into the catheter 350. To compress the funnel, the device 200 can be advanced out of the funnel and away from the mesh 370. Next, the distal shaft 352 can be advanced through the neck portion 371 of the mesh 370 to receive the device 200. In another variation, the device 350 can include a single shaft 354 where the mesh 370 can extend beyond the shaft 354. The mesh can be heat set to assume a funnel shape upon the application of a current or as it reaches body temperature. In another variation, the mesh 370 can comprise a super-elastic material that assumes the shape shown in FIG. 13E when released from a constraining member.

Figure 13G:
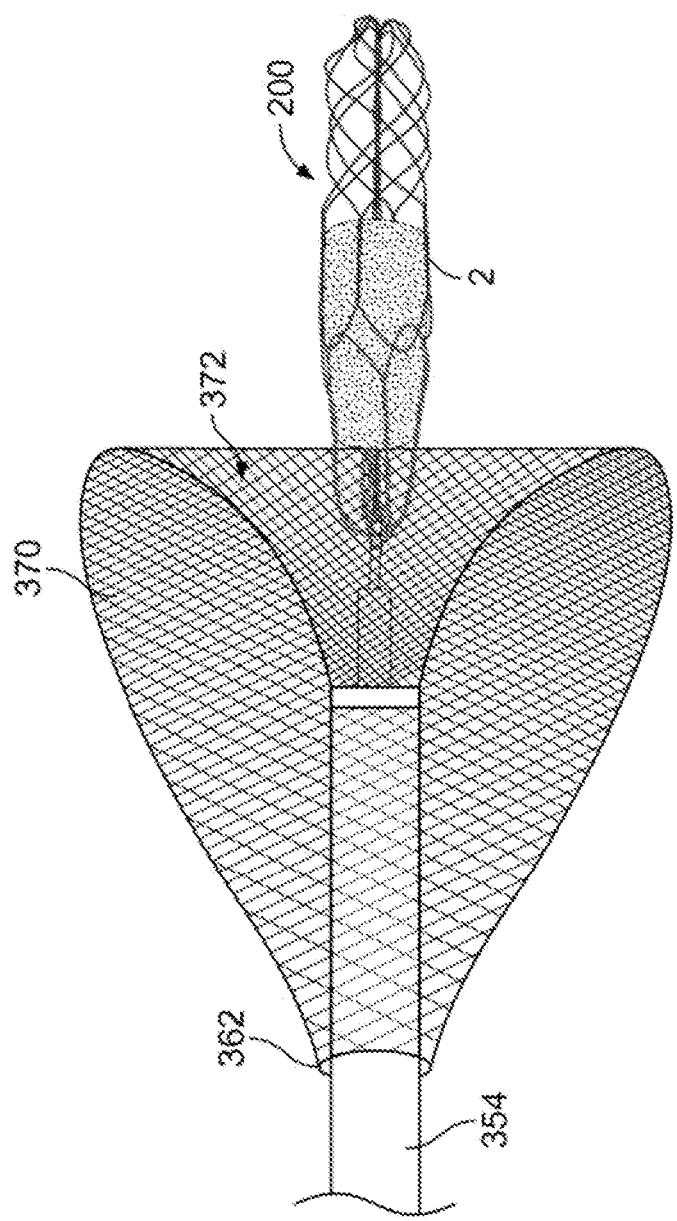
Figure 13F:
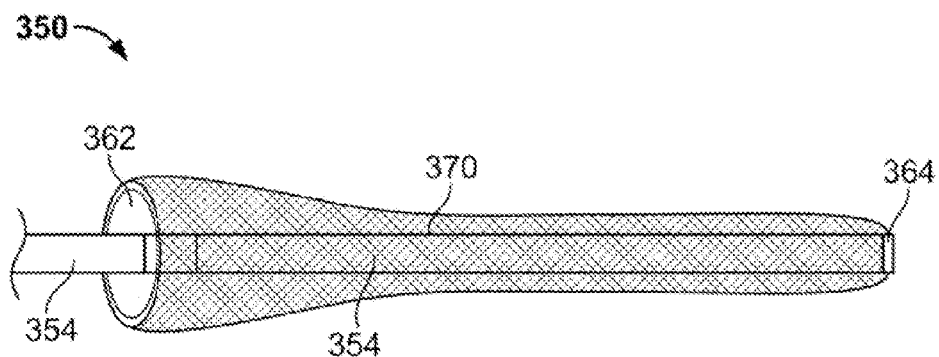

FIGS. 13F to 13G illustrate yet another variation a funnel catheter 350 suited to remove a retrieval device 200 from the body. In this variation, the funnel catheter 350 includes a single shaft 354 having a mesh 370 is fused to a distal location 364. The mesh 370 is free at a proximal side. The mesh is also pre-formed to assume a funnel shape as shown in FIG. 13G. Accordingly, upon delivery the mesh 370 can be constrained (e.g., via a sheath, or other removable restraint). Once the restraint is removed, the mesh 370 expands to form a funnel 372.

Figure 14A:
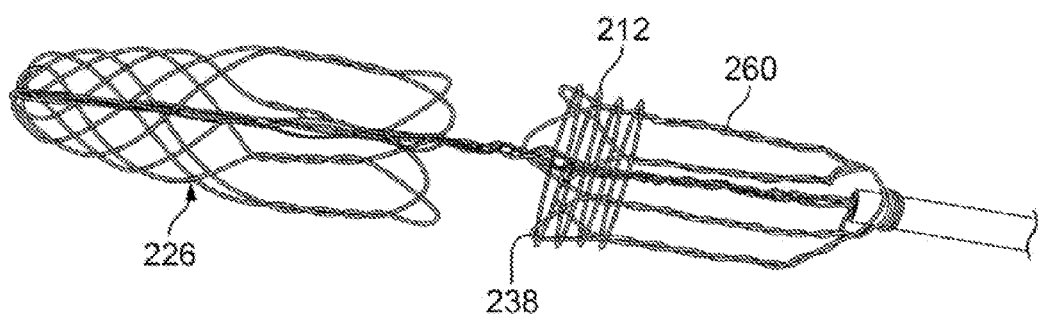

FIGS. 14A to 14D illustrate additional concepts for use with various retrieval devices 200. FIG. 14A illustrates a distal capturing portion 226 and a proximal capturing portion 260 where the proximal capturing portion includes a covering 212 (e.g., a polymeric covering or a wire or fiber wound about the flanges 238). The covering 212 prevents the flanges 238 of the distal capturing portion 226 from flaring outside of the proximal capturing portion 260.

Figure 14B:
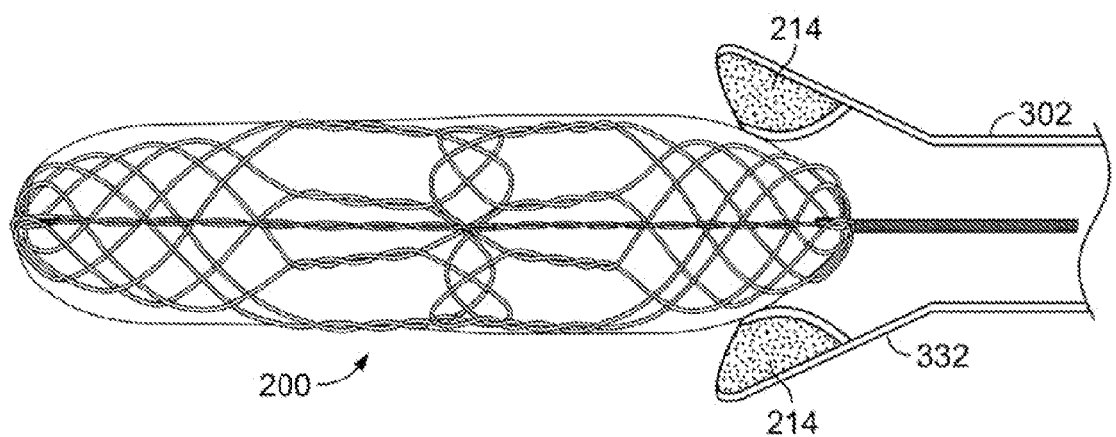

FIG. 14B illustrates a variation of a reentry sleeve where tines 332 of the reentry sleeve 302 include protrusions 214 on an inner surface. The protrusions 214 cause the tines 332 to splay out as the retrieval device 200 is withdrawn within the tines 332. As the reentry sleeve 302 is withdrawn in a guide catheter (as discussed above) the protrusions serve to compress the retrieval device 200 even further.

Figure 14C:
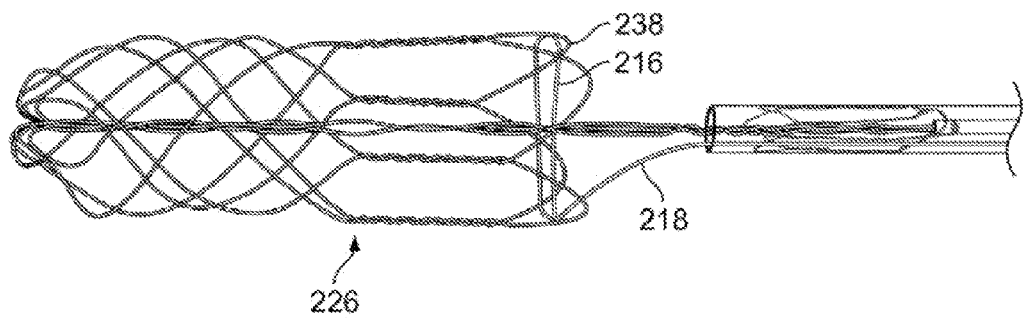
Figure 14D:
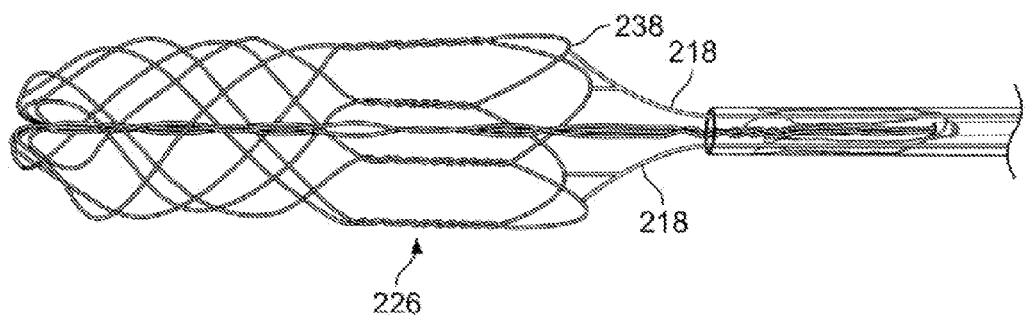

FIGS. 14C and 14D illustrate variations of a wire or fiber 218 affixed to the flanges 238 of a distal capturing portion 226 to assist in compressing the flanges 238 prior to entry within a guide sheath. As shown in FIG. 14C the fiber 218 can be affixed to a suture ring 216. As the fiber 218 is pulled, the suture ring 216 compresses the flanges 238 to prevent outward flaring. In FIG. 14D, one or more fibers 218 are affixed to one or more flanges 238. Once the obstruction is captured, the fibers can be pulled to draw the flanges 238 closed.

FIG. 15 illustrates another variation of a retrieval device 200 including a distal capture portion 226 coupled to one or more leading wires in the form of a main bundle 202. The main bundle extends through a sheath 106 that includes a proximal capture portion 266 is configured to expand when placed within or moved into an obstruction in a blood vessel. For example, the illustrated variation includes a translating portion 234 adjacent to an open distal end 288. Next, the proximal capture portion 266 includes a surface 290 adjacent to the translating portion 234 (or adjacent to the open distal end 288 if no translating portion is used). The surface 290 comprises a higher density than that of the translating portions described above. In some variations, the surface 290 can comprise a low-density surface but the device is otherwise configured to expand within an obstruction. As shown, the proximal surface 292 is fluid permeable to allow blood flow when the proximal capture portion 266 is deployed in a vessel.

The proximal capture portion 266 illustrated can comprise a construction similar to that of a stent-type device, where such a configuration permits the proximal capture portion 266 to be deployed against an obstruction in a manner similar to a stent deployment. As described below, application of the capture portion 266 within an obstruction allows for re-establishing blood flow, in the event the obstruction is a total occlusion. A therapeutic substance can then be delivered to the obstruction to assist in breaking down the obstruction. For example, the substance can be delivered through a microcatheter (not shown), delivery sheath 106 or by any fluid delivery mode described herein.

The configuration of the retrieval device 200 can incorporate the proximal and distal capture portions discussed herein as well as various other configurations discussed in the commonly assigned patent applications noted above. In addition, the relative sizes of the various components shown in FIG. 15 and discussed below are for illustrative purposes only.

An end 292 of the proximal capture portion 266 is affixed to a distal end of a sheath 106. However, as noted above, other variations are within the scope of the disclosure. The main bundle 202 can optionally terminate at a handle 242. As noted above, in certain variations, the main bundle is joined to a stiffer wire or stiffer bundle of wires. This allows the device 200 to have a very flexible distal section with a relatively stiffer proximal section. FIG. 4A above, discusses placement of a joint at a location spaced from the distal section of the device so as to increase a bond strength but not impair the distal section's flexibility. In any case, the device 200 can have a proximal bundle 203 that comprises either the exposed wires or a covering/tube over the wires. In certain variations, the bundle or wire 202, 203 can be encapsulated with a coating.

The proximal end of the sheath 106 includes a sheath handle 244. As discussed herein, axial movement of the bundle 202 or proximal bundle 203 (typically at the handle 242) results in movement 126, or translation of the bundle within the sheath 106. This action moves the distal capture portion 226 (as shown by arrows 126). In certain variations, the device 200 is loaded into a microcatheter (not shown but discussed above) that is delivered to the site of the obstruction and crosses the obstruction.

In some variations, the sheath hub 244 includes one or more locking hubs 246. Where actuation (either axial or rotational) of the locking hub 246 locks the main bundle 202 relative to the sheath handle 244 and sheath 106. It follows that such locking action also locks the distal capture portion 226 relative to the proximal capture portion 266. A variety of methods can be employed to increase a frictional interference between the locking hub 246 and the proximal bundle 203. As a result, when a physician determines a length of an obstruction, the physician can set a spacing between the capturing portions 226 266 by locking the proximal bundle 203 relative to the sheath hub 244. As illustrated, the sheath hub 244 can include additional injection ports to deliver fluid or other substances through the sheath 106.

FIGS. 16A to 16E demonstrate an example of a retrieval device 200 that uses a proximal capture portion 266 that is configured to be deployed against an obstruction 2 within a vessel 6 or other lumen.

Figure 16A:
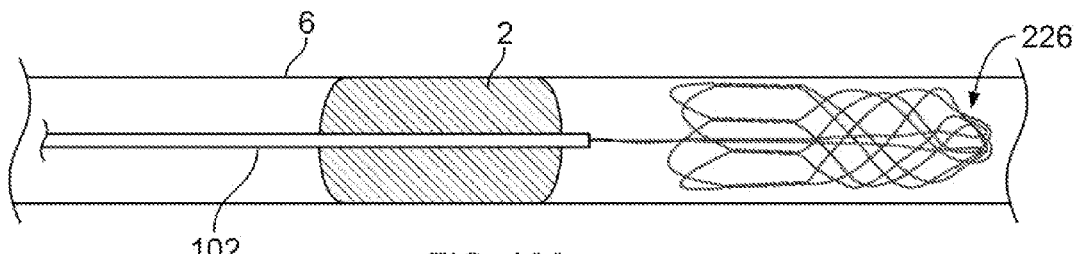

FIG. 16A illustrates a microcatheter 102 positioning a distal capture portion 226 beyond the obstruction 2. As noted above, the distal capture portion 226 can serve as a filter by capturing debris or other particles that break free from the obstruction 2 during the procedure. Moreover, the procedures and techniques described herein can be used to assist with placing the distal capture portion 226 downstream of the obstruction 2.

Figure 16B:
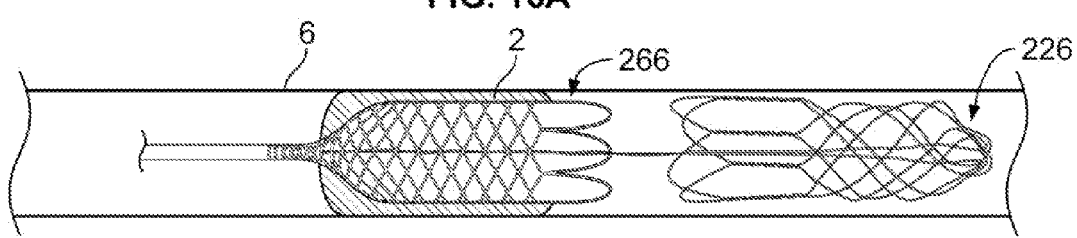

FIG. 16B illustrates the proximal capture portion 266 being deployed against the obstruction 2. In those situations where the obstruction 2 totally or significantly occludes the vessel, deployment of the proximal capture portion 266 can re-establish blood flow upon deployment. Although FIG. 16A illustrates the proximal capture portion 226 being deployed within the obstruction 2, alternative variations include deployment of the proximal capture portion distally to the obstruction 2 and then translated proximally into the obstruction 2.

Figure 16C:
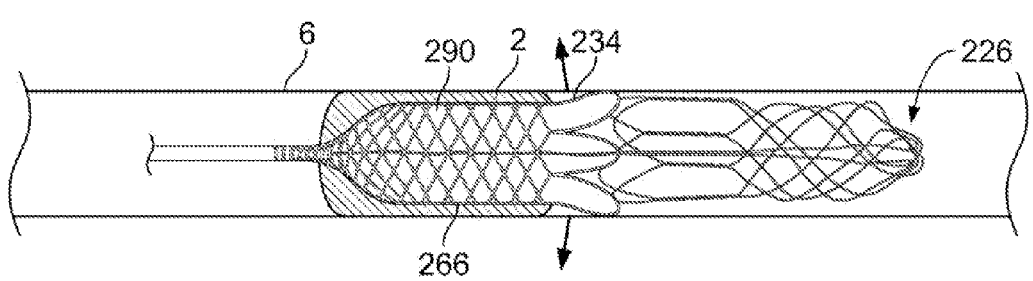

FIG. 16C illustrates an optional procedure where the distal capture portion 226 can be withdrawn against the proximal capture portion 266. The action of the distal capture portion 226 applies an axial force against the proximal capture portion 266 causing the proximal capture portion 266 to further expand against the obstruction 2. The motion can be cycled to work the proximal capture portion 266 against the obstruction 2. In some variations, the proximal capture portion 266 includes a translating portion 234 that facilitates entry of the distal capture portion 226 therein to assist in expanding the proximal capture portion 266 and more particularly the high density surface 290.

At this point a physician can apply a substance (as described herein) that dissolves the obstruction 2. In some cases, the residual obstruction 2 can be removed from the vessel 6 simply by removing the proximal capture portion 266 when the residual obstruction 2 adheres to or within the high density surface 290. As noted herein, the distal capture portion 226 can simply function as a distal filter by trapping debris generated by the removal process. In some variations, the proximal capture portion 266 is only partially deployed when engaging the obstruction 2. In such a case, a proximal segment of the proximal capture portion 266 can remain within the microcatheter. In addition, the microcatheter can recapture the proximal capture portion 266 and then withdraw it to the proximal side of the obstruction 2.

Figure 16D:
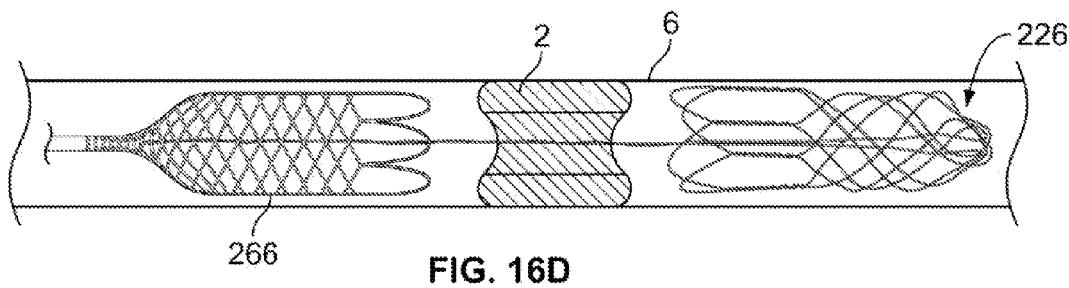
Figure 16E:
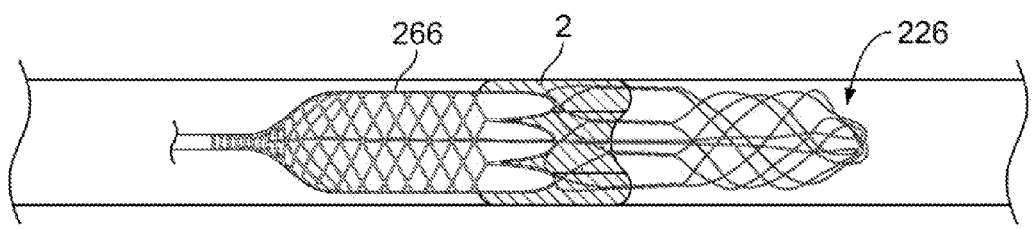

FIG. 16D illustrates a condition where the residual obstruction 2 does not remain affixed to the proximal capture portion 266. As shown, the proximal capture portion 266 is withdrawn proximally of the residual obstruction 2. The physician can then use the proximal and distal capture portions 266 and 226 to surround and capture the obstruction 2 as described above. FIG. 16E illustrates such a condition as the distal capture portion 226 is withdrawn over the obstruction and the proximal capture portion 266 is advanced to the obstruction 2 to surround, capture, and ultimately remove the obstruction 2. As noted above, variations of the procedure include deploying only a section of the proximal capture portion 266 to capture the obstruction 2. In such variations, the section of the proximal capture portion 266 that extends from the microcatheter will resemble the proximal capture portions disclosed above (e.g., FIG. 10).

FIGS. 17A to 17C illustrate another variation of a working portion of an obstruction removal device 200. In this variation, the obstruction removal device 200 includes a distal capturing portion 226 affixed to a proximal section 294 comprising one or more high density sections 296 interconnected with one or more low density sections 298. The high density sections 296 can comprise stent-like structures such as laser cut tubes, braided, or woven filaments, wires, DFT, etc. The proximal section 294 can be coupled to a catheter, push wire, or other member 299. The structure can be a continuous structure that is fabricated via any known manufacturing process.

FIG. 17B illustrates one use of the device of FIG. 17A. As shown, the proximal section 294 is deployed against an obstruction 2 within a vessel 6 to re-establish or increase blood flow distal to the obstruction 2. The high density sections 296 are configured to apply a radial expansive force against the obstruction 2 and, in some variations, embed the high density section 296 within the obstruction 2. The distal capture portion 226 serves as a distal filter by capturing debris and other material that breaks free from the obstruction 2. As illustrated, part of the obstruction 2 will enter the low density section 298 of the proximal section 294.

FIG. 17C illustrate the device of FIG. 17B being moved in a distal or reciprocating motion (as shown by the arrows). The reciprocating motion can shear portions of the obstruction 2 that are either embedded within the high density section 296 or are at the transition between the high density section 296 and the low density section 298. A physician can deploy and re-deploy the device to ultimately remove the obstruction. In some variations, the obstruction adheres to the high density section 296 allowing for removal. In other variations, the obstruction 2 becomes entrapped within the distal capture portion 226 upon withdrawal of the device. It should also be noted that additional elements such as wires or filaments can be located on the inside of the body 294 to enhance the ability for the clot to stay entwined within the cavity 294.

FIGS. 18A to 18H illustrate a variation of the capture portions or sections for use with the systems and methods described herein. In these variations, the capture portions are configured to deliver a substance (such as a therapeutic or obstruction dissolving substance) at a perimeter of the device so that the substance can be deployed closely to the obstruction.

Figure 18A:
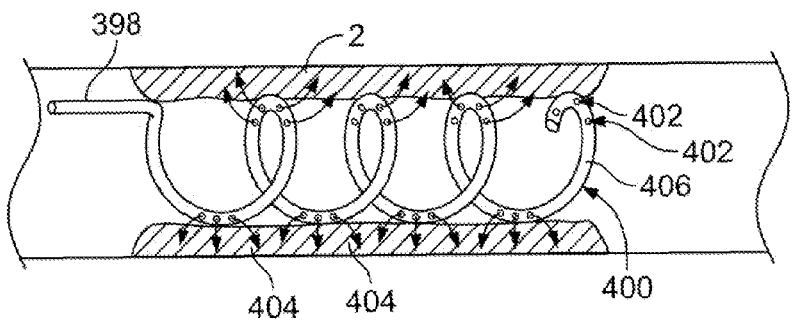

FIG. 18A illustrates a simply coil stent structure 400 fabricated from a hollow structure 406 such as a super-elastic material. In one variation, the hollow structure 406 includes a number of fluid delivery ports 402 on an outer surface of the structure 400. This placement allows for delivery of the substance directly into the obstruction 2 as the fluid flows 404 from a perimeter of the coil structure 400. The fluid ports 402 can be drilled into the hollow structure 406 using techniques known by those skilled in the art of fabricating such medical devices, such as mechanical drilling or laser drilling. In those variations using a coil stent structure 400, pulling back into the microcatheter or other delivery catheter 398 can deploy the stent structure 400. Alternatively, a push wire can be used to elongate or straighten the stent structure 400 for deployment and withdrawal from the obstruction 2.

Figure 18B:
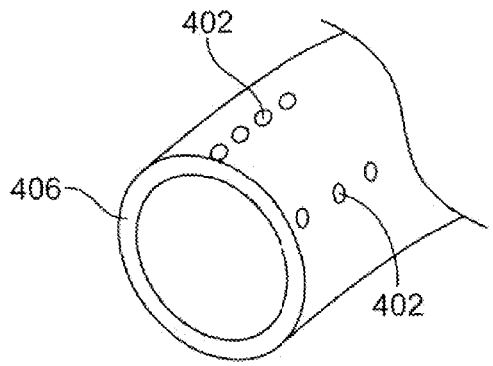

FIG. 18B illustrates an example of a cross sectional view of the hollow structure 406 of FIG. 18A. Although the structure 406 shows a cylindrical shape, any shape can be used. Moreover, any biocompatible material can be used for the structure 406, including but not limited to a shape memory alloy such as Nitinol.

Figure 18C:
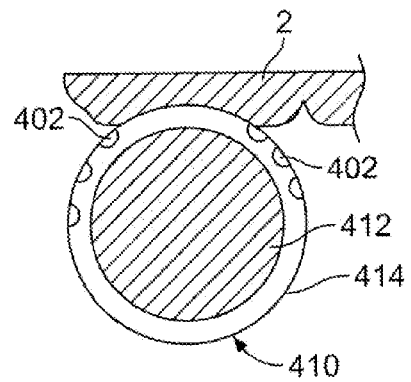

FIG. 18C illustrates another variation of a structure 410 having fluid delivery ports 402. In this variation a polymer layer 414 covers an inner core material 412 (e.g., Nitinol). The fluid ports 402 are located in a surface of the polymer layer 414. Moreover, the polymer layer or the core material will have one or more fluid passages to allow for delivery of the fluid through the ports from a proximal end of the device.

Figure 18D:
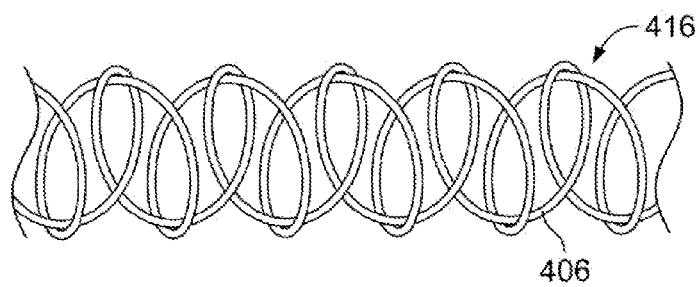
Figure 18E:
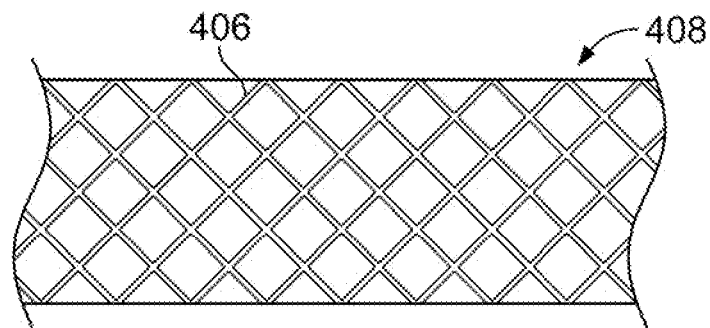

FIGS. 18D and 18E illustrate additional structures for use as stent or capturing structures as described herein. In FIG. 18D, the structure 416 comprises a double coil or double helix with one or more wires. FIG. 18E illustrates a braided structure 418 with one or more wires. Fluid ports can be positioned in one or more of the wires. Moreover, the stent structures described herein can be actuated using a straightening rod for deployment and withdrawal. Alternatively, the structures can be self-expanding and deployed when released from a catheter or other sheath.

Figure 18F:
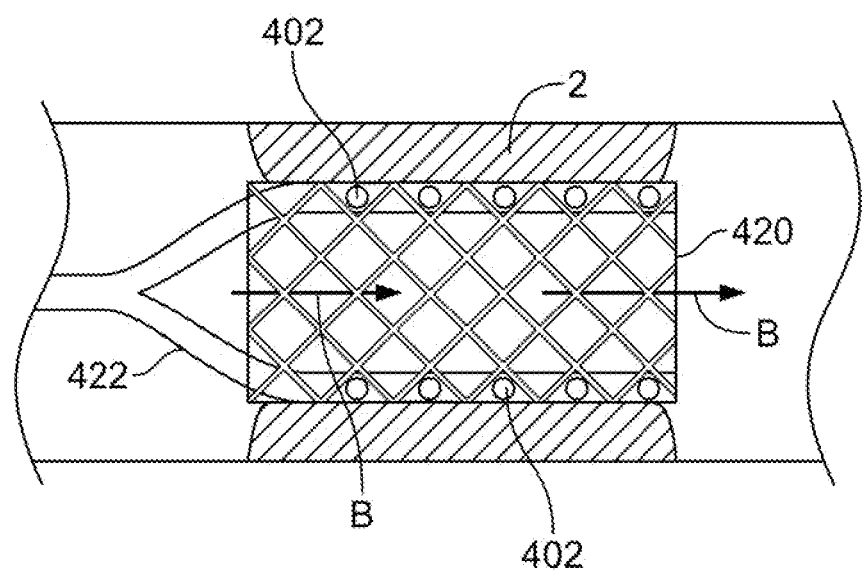
Figure 18G:
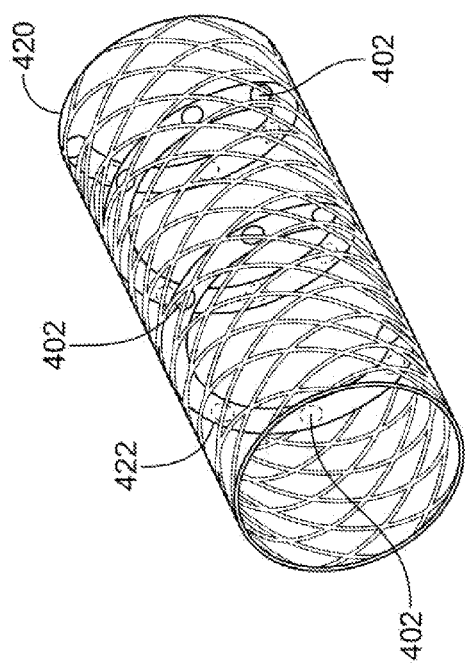

FIGS. 18F and 18G illustrate an additional variation of a structure 420 incorporating fluid delivery ports 402. However, in these variations, the fluid ports 420 are located in a fluid delivery tube 422 affixed to the structure 420. In both variations, blood flow 13 is maintained as the fluid delivery tube 422 is affixed to a perimeter of the structure 420. FIG. 18F illustrates a branching tube 422 having at least two branch tubes affixed to the perimeter of the structure 420. FIG. 18G illustrates a fluid delivery tube 422 interwoven in a stent structure 420 so that fluid delivery ports 402 are situated at or near a perimeter of the structure 420.

Figure 18H:
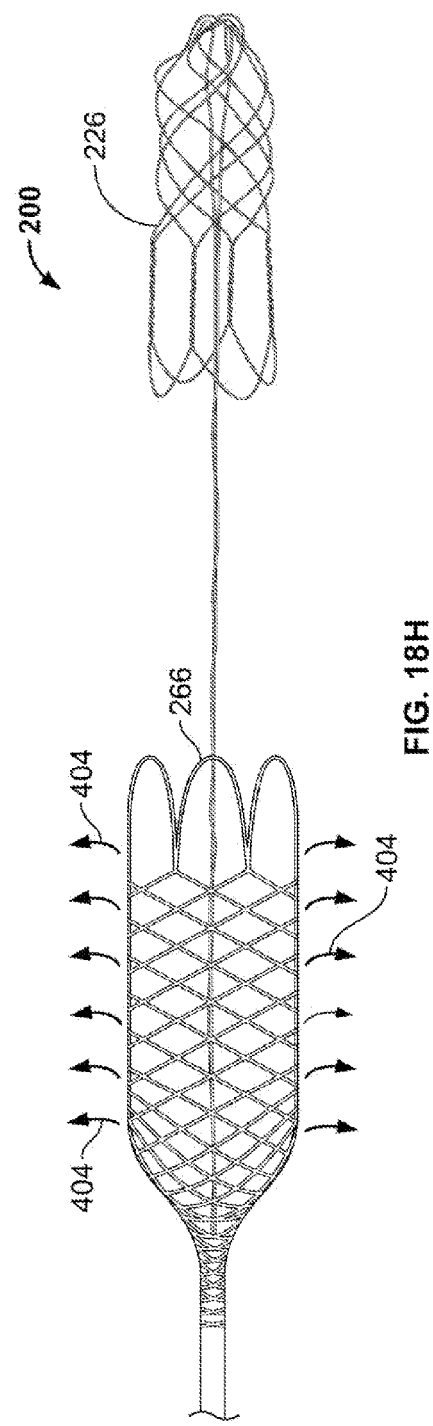

FIG. 18H illustrates another variation of a device 200 incorporating fluid delivery ports. This variation is similar to that shown in FIG. 15 where fluid delivery ports are fabricated in the proximal capture portion 266. As shown, fluid flow 404 takes place at the perimeter of the capture portion 266 in direct contact or closely to any obstruction.

In addition to fluid delivery ports, any of the devices described herein can be coated with therapeutic or other substances as described herein. Alternate variations include such substances placed in reservoirs within the capture portions so that such substances need not be conveyed along a length of the system from a proximal end of the system to the capture portions.

Various changes may be made to the invention described and equivalents (whether recited herein or not included for the sake of some brevity) may be substituted without departing from the true spirit and scope of the invention. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item, includes the possibility that there are plural of the same items present. More specifically, as used herein and in the appended claims, the singular forms "a," "and," "said," and "the" include plural references unless the context clearly dictates otherwise.

It is important to note that where possible, aspects of the various described embodiments, or the embodiments themselves can be combined. Where such combinations are intended to be within the scope of this disclosure.

The invention claimed is:

1. A method of recanalizing a blood vessel having an obstruction, the method comprising:
    inserting an expandable structure within the obstruction, where the expandable structure comprises at least one fluid delivery port on an exterior surface of the expandable structure;
    expanding the expandable structure within the obstruction; and
    delivering a substance through the fluid delivery port such that the substance begins to dissolve the obstruction.

2. A method of recanalizing a blood vessel having an obstruction, the method comprising:
    advancing a microcathter distal to the obstruction;
    deploying a distal capturing portion distally of the obstruction;
    positioning a proximal capturing portion within the obstruction, such that the proximal capturing portion extends beyond a first end and a second end of the obstruction and where the proximal capturing portion expands to compress a portion of the obstruction against the vessel;
    withdrawing the proximal capturing portion proximally to the obstruction;
    securing the obstruction by moving the distal capturing portion and the proximal capturing portion together; and
    removing the obstruction from the blood vessel.

3. The method of claim 2, where withdrawing the proximal capturing portion comprises resheathing at least a section of the proximal capturing portion within a microcatheter during withdrawal of the proximal capturing portion.

4. The method of claim 3, further comprising partially deploying a segment of the proximal capturing portion from the microcatheter proximal to the obstruction such that the partially deployed segment functions as a proximal basket.

5. The method of claim 2, where the proximal capturing portion structure comprises a stent portion having a fluid permeable proximal end.

6. The method of claim 2, further comprising delivering a substance to the obstruction where the substance is configured to dissolve the obstruction.

7. The method of claim 6, where delivering the substance to the obstruction comprises delivering the substance through the microcatheter.

8. The method of claim 6, where delivering the substance to the obstruction comprises delivering the substance through a surface of the proximal capturing portion.

9. The method of claim 2, further comprising withdrawing the distal capturing portion against the proximal capturing portion while the proximal capturing portion is located in the obstruction to cause the proximal capturing portion to increase a radial force to the obstruction.

10. The method of claim 2, where positioning the proximal portion within the obstruction comprises positioning the proximal capturing portion distally to the obstruction and then withdrawing the proximal capturing portion into the obstruction.

11. The method of claim 10, where withdrawing the second capturing portion comprises resheathing at least a section of the second capturing portion within a microcatheter during withdrawal of the second capturing portion.

12. The method of claim 11, further comprising partially deploying a segment of the second capturing portion from the microcatheter proximal to the obstruction such that the partially deployed segment functions as a proximal basket.

13. The method of claim 10, where pulling on the leading wire to apply the force to the capturing portion comprises applying the force to the permeable distal end.

14. The method of claim 10, where pulling on the leading wire to apply the force to the capturing portion comprises applying the force to the capture surface.

15. The method of claim 10, where the proximal end of the second capturing portion is permeable and permits flow during removal of the obstruction.

16. The method of claim 10, further comprising continuing to move the first capturing portion towards the second capturing portion such that the open proximal end and the open distal end can removably engage each other.

17. The method of claim 10, further comprising compressing the second capturing portion about the obstruction to further secure the obstruction.

18. A method of recanalizing a blood vessel having an obstruction, the method comprising:
    advancing a catheter distal to the obstruction;
    deploying a first capturing portion distally of the obstruction, where the first capturing portion comprises a permeable distal end, an open proximal end, a capture surface extending therebetween, and at least one leading wire extending through the capturing portion and through the catheter;
    positioning a second capturing portion within the obstruction, the second capturing portion having an open distal end, a fluid permeable proximal end, and a medial surface extending therebetween, such that the second capturing portion compresses a portion of the obstruction against the blood vessel;
    withdrawing the second capturing portion proximal to the obstruction;
    capturing the obstruction between the first and second capturing portions by moving the first capturing portion and the second capturing portion together towards the obstruction by pulling on the leading wire to apply a force to the capturing portion at a location distal to the open proximal end of the first capturing portion; and
    removing the obstruction from the blood vessel.

* * * * *